(12) United States Patent
Takamochi et al.

(10) Patent No.: US 10,787,711 B2
(45) Date of Patent: Sep. 29, 2020

(54) METHOD FOR DIFFERENTIATING BETWEEN LUNG SQUAMOUS CELL CARCINOMA AND LUNG ADENOCARCINOMA

(71) Applicants: JUNTENDO EDUCATIONAL FOUNDATION, Bunkyo-ku (JP); RIKEN, Wako-shi (JP)

(72) Inventors: Kazuya Takamochi, Bunkyo-ku (JP); Kenji Suzuki, Bunkyo-ku (JP); Tsuyoshi Saito, Bunkyo-ku (JP); Kieko Hara, Bunkyo-ku (JP); Keiko Mitani, Bunkyo-ku (JP); Kaoru Mogushi, Bunkyo-ku (JP); Yoshihide Hayashizaki, Wako (JP); Masayoshi Ito, Wako (JP); Hideya Kawaji, Wako (JP); Hiroko Oomiya, Wako (JP); Yasunari Yamanaka, Wako (JP)

(73) Assignees: JUNTENDO EDUCATIONAL FOUNDATION, Bunkyo-ku (JP); RIKEN, Wako-shi (JP)

( * ) Notice: Subject to any disclaimer, the term of this patent is extended or adjusted under 35 U.S.C. 154(b) by 67 days.

(21) Appl. No.: 15/125,366

(22) PCT Filed: Mar. 11, 2015

(86) PCT No.: PCT/JP2015/057176
§ 371 (c)(1),
(2) Date: Sep. 12, 2016

(87) PCT Pub. No.: WO2015/137406
PCT Pub. Date: Sep. 17, 2015

(65) Prior Publication Data
US 2017/0073766 A1 Mar. 16, 2017

(30) Foreign Application Priority Data

Mar. 12, 2014 (JP) .................................. 2014-049186
Sep. 9, 2014 (JP) .................................. 2014-183418

(51) Int. Cl.
*G01N 33/574* (2006.01)
*C12Q 1/6886* (2018.01)

(52) U.S. Cl.
CPC ..... *C12Q 1/6886* (2013.01); *G01N 33/57423* (2013.01); *C12Q 2600/112* (2013.01); *C12Q 2600/158* (2013.01)

(58) Field of Classification Search
CPC ............ C12Q 1/6886; C12Q 2600/112; C12Q 2600/158; G01N 33/57423
See application file for complete search history.

(56) References Cited

U.S. PATENT DOCUMENTS

2009/0297536 A1* 12/2009 Chin .................... C12Q 1/6886
424/172.1

OTHER PUBLICATIONS

Cappuzzo, F. et al. Lancet Oncology 11:521 (May 2010).*
Wang, N. et al. The Anatomical Record 295:748 (online Mar. 15, 2012). (Year: 2012).*
Carrascal, M. et al. Molecular Oncology 8:753 (online Mar. 6, 2014). (Year: 2014).*
Carvalho, R. et al. Epigenetics & Chromosome 5:9 (Jun. 22, 2012). (Year: 2012).*
International Search Report dated Jun. 16, 2015 in PCT/JP2015/057176 filed Mar. 11, 2015.
Zhong Wang, et al., "RNA-Seq: a revolutionary tool for transcriptomics", Nature Reviews Genetics, vol. 10, No. 1, Jan. 2009, pp. 57-63.
Mutsumi Kanamori-Katayama, et al., "Unamplified cap analysis of gene expression on a single-molecule sequencer", Genome Research, vol. 21, No. 7, May 19, 2011, 11 pages.
Anna Lopez-Ferrer, et al., "Differences in the O-Glycosylation Patterns Between Lung Squamous Cell Carcinoma and Adenocarcinoma", American Journal of Clinical Pathology, vol. 118, No. 5, Nov. 2002, pp. 749-755.
Sayumi Shirakawa, et al., "Association between Sialyl Tn (sTn) Antigen Synthase (ST6GalNAc I) and sTn Antigen", Abstracts of XXIXth Japanese Carbohydrate Symposium, p. 144, Sep. 9-10, 2009, 4 pages (with English abstract and partial English translation).
Alan F. Brown, et al., "Tissue-Preserving Antibody Cocktails to Differentiate Primary Squamous Cell Carcinoma, Adenocarcinoma, and Small Cell Carcinoma of Lung", Archives of Pathology & Laboratory Medicine, Vo. 137, No. 9, 2013, pp. 1274-1281.
Suyan Tian, et al., "Hierarchical-TGDR, Combining biological hierarchy with a regularization method for multi-class classification of lung cancer samples via high-throughput gene-expression data", Systems Biomedicine, vol. 1, No. 4, Sep. 20, 2013, 11 pages.
Bogumil Kaczkowski, et al., "Pan Cancer Biomarkers and Disruption of Gene Regulatory Networks in Cancer Inferred from CAGE Data of FANTOM5 Project", The 36th Annual Meeting of the Molecular Biology Society of Japan Program Yoshishu, 2P-0044, Nov. 20, 2013, 2 pages (with English translation).

(Continued)

*Primary Examiner* — Diana B Johannsen
(74) *Attorney, Agent, or Firm* — Oblon, McClelland, Maier & Neustadt, L.L.P.

(57) ABSTRACT

Provided is an approach for differentially determining the histological type of a lung cancer lesion objectively and rapidly with high accuracy. A method for differentially assessing a lesion in a lung cancer patient as squamous cell carcinoma or adenocarcinoma, comprising a step of measuring an expression level of an expression product of at least one DNA comprising a transcription start site in a biological sample collected from the lesion, wherein the DNA comprises a base at an arbitrary position in the transcription start site and at least one or more bases located immediately downstream thereof in any of nucleotide sequences represented by SEQ ID NOs: 1 to 213, and the transcription start site is a region wherein both ends thereof are defined by the first base and the 101st base counted from the 3' end in any of the nucleotide sequences represented by SEQ ID NOs: 1 to 213.

9 Claims, No Drawings
Specification includes a Sequence Listing.

(56) References Cited

OTHER PUBLICATIONS

Kazuya Takamochi, et al., "1172P—Novel Biomarkers to Discriminate Between Primary Lung Squamous Cell Carcinoma and Adenocarcinoma Identified by The Cap Analysis of Gene Expression", Annals of Oncology, vol. 25, Supplement 4, 2014, 2 pages.

Kazuya Takamochi, et al., "CAGE-ho ni yoru Hai Genpatsu Henpei Johigan to Sengan no Shinki Kanbetsu Marker no Dotei", Japanese Journal of Lung Cancer, vol. 54, No. 5, PD-31, Oct. 5, 2014, 5 pages (with partial English translation).

* cited by examiner

METHOD FOR DIFFERENTIATING BETWEEN LUNG SQUAMOUS CELL CARCINOMA AND LUNG ADENOCARCINOMA

FIELD OF THE INVENTION

Related Application and Incorporation by Reference

The present application claims the priority of Japanese Patent Application No. 2014-049186 filed on Mar. 12, 2014 and Japanese Patent Application No. 2014-183418 filed on Sep. 9, 2014, the whole contents of which are incorporated herein by reference.

All literatures cited herein are incorporated herein by reference in their entirety for every purpose. The citation of any literature is not to be construed as an admission that it is prior art with respect to the present invention.

The present invention relates to a novel marker which allows the histological type of lung cancer to be differentially determined easily even in a microscopic tissue specimen such as a biopsy specimen. More specifically, the present invention relates to an approach for differentially assessing a lung cancer lesion as squamous cell carcinoma or adenocarcinoma at a molecular level.

BACKGROUND OF THE INVENTION

Lung cancer, which kills 70,000 people a year in Japan, is broadly classified into small-cell cancer and non-small cell lung cancer. The non-small cell lung cancer is further classified into adenocarcinoma, squamous cell carcinoma, large-cell cancer, and other rare histological types.

In recent years, an anticancer agent (pemetrexed) and a molecular targeting therapeutic drug (bevacizumab), which have therapeutic effects and adverse reactions largely different between squamous cell carcinoma and the other non-small cell lung cancers (non-squamous cell carcinomas), have emerged. Thus, the accurate differentiation therebetween is essential for determining therapeutic strategies. Nonetheless, the differentiation therebetween may be histopathologically difficult for microscopic specimens such as biopsy specimens. At present, histopathological diagnosis is comprehensively conducted by use of not only cell or tissue morphology but immunohistological staining using markers specific for squamous cell carcinoma or adenocarcinoma. Still, the differentiation is difficult for many cases using microscopic specimens and is particularly difficult for cancer having a low degree of differentiation.

The histological basis for the diagnosis of lung squamous cell carcinoma is the presence of intercellular bridge or keratinization in a cancer tissue. The degree of differentiation of lung squamous cell carcinoma is determined depending on the amount of intercellular bridge or keratinization. Squamous cell carcinoma having a low degree of differentiation (poorly differentiated squamous cell carcinoma) manifests intercellular bridge and keratinization remaining only in a small region in the whole cancer tissue. On the other hand, the lung adenocarcinoma is broadly classified into one containing or not containing a bronchioloalveolar type (BAC) component. Morphological diagnosis of adenocarcinoma containing a BAC component is easy, whereas adenocarcinoma free of a BAC component may be difficult to differentiate from poorly differentiated squamous cell carcinoma. Heretofore, P40, CK5, CK6, DSG3, TTF-1, and napsin A have been used as immunohistological staining markers for the differentiation between squamous cell carcinoma and adenocarcinoma, but are not always sufficient in terms of accuracy, etc. Thus, there is a demand for a more highly accurate marker at the present circumstance.

In addition, differential diagnosis may depend largely on the subjectivity of pathologists. Thus, an objective and universal determination method is required.

Meanwhile, in recent years, an approach for gene expression analysis has been developed which involves comprehensively analyzing genes expressed in cells in a certain state by the comparison of the expression statuses of the genes, and comparing their types or expression levels among the cells. For example, RNA-seq (Non Patent Literature 1) and CAGE (cap analysis gene expression; Non Patent Literature 2) are known to comprehensively analyze the expression statuses of genes at transcription start sites as sequence information. Of these methods, CAGE is characterized in that this method is capable of comprehensively quantifying the activity of transcription start points by selecting long capped RNAs such as mRNA and sequencing their 5' ends at random and at a large scale.

However, none of the previous reports mention the relation of the expression level of a transcription start site in the human genome to a particular disease.

CITATION LIST

Non Patent Literature

Non Patent Literature 1: Nature Reviews Genetics 10 (1): 57-63

Non Patent Literature 2: Genome Res. 2011 July; 21 (7): 1150-9

SUMMARY OF THE INVENTION

Problems to be Solved by the Invention

The present invention relates to provide an approach for differentially assessing a lung cancer lesion as lung squamous cell carcinoma or lung adenocarcinoma objectively and rapidly with high accuracy.

Means for Solving the Problems

The present inventors have extracted RNA from lesions of lung squamous cell carcinoma patients and lung adenocarcinoma patients, and comprehensively analyzed their expression statuses near transcription start sites (TSSs) as sequence information by the CAGE analysis method. As a result, the present inventors have found that the expression level of DNA containing a particular transcription start site significantly differs between squamous cell carcinoma and adenocarcinoma, and this difference can be used as an index to discriminate between the squamous cell carcinoma and the adenocarcinoma.

Specifically, the present invention relates to the following 1) to 4):

1) A method for differentially assessing a lesion in a lung cancer patient as squamous cell carcinoma or adenocarcinoma, comprising a step of measuring an expression level of an expression product of at least one DNA comprising a transcription start site in a biological sample collected from the lesion, wherein the DNA comprises a base at an arbitrary position in the transcription start site and one or more bases located immediately downstream thereof in any of nucleotide sequences represented by SEQ ID NOs: 1 to 213, and the transcription start site is a region wherein both ends thereof are defined by the first base and the 101st base counted from the 3' end in any of the nucleotide sequences represented by SEQ ID NOs: 1 to 213.

2) A testing kit for differentially assessing a lesion in a lung cancer patient as squamous cell carcinoma or adenocarcinoma for use in the method according to 1), the testing kit comprising an oligonucleotide specifically hybridizing to a transcription product of the DNA, or an antibody recognizing a translation product of the DNA.

3) Use of an expression product of at least one DNA comprising a transcription start site, as a marker for differentially assessing a lesion in a lung cancer patient as squamous cell carcinoma or adenocarcinoma, wherein the DNA comprises a base at an arbitrary position in the transcription start site and one or more bases located immediately downstream thereof in any of nucleotide sequences represented by SEQ ID NOs: 1 to 213, and the transcription start site is a region wherein both ends thereof are defined by the first base and the 101st base counted from the 3' end in any of the nucleotide sequences represented by SEQ ID NOs: 1 to 213.

4) A method for differentially assessing a lesion in a lung cancer patient as squamous cell carcinoma or adenocarcinoma, comprising a step of measuring an expression level of ST6GALNAC1 and/or SPATS2 protein in a biological sample collected from the lesion.

Effects of the Invention

According to the present invention, the differentiation between squamous cell carcinoma and adenocarcinoma, further the differentiation between poorly differentiated squamous cell carcinoma and adenocarcinoma, and further the differentiation between poorly differentiated squamous cell carcinoma and adenocarcinoma free of a BAC component can be achieved for a cancer lesion in a lung cancer patient. This permits rapid diagnosis. Also, use of the present invention allows the differentiation between squamous cell carcinoma and adenocarcinoma to be objectively carried out at a level equivalent to or higher than the subjectivity of specialists such as well-trained pathologists or clinical laboratory technicians. The present invention can also be suitably used in point of care testing (POCT) from the collection of specimens from patients to the analysis thereof.

Modes for Carrying Out the Invention

In the present invention, the "squamous cell carcinoma (lung squamous cell carcinoma)" means a cancer which develops in the squamous epithelium (squamous metaplasia cells) of the bronchus.

Also, the adenocarcinoma (lung adenocarcinoma) means a cancer which develops in the glandular cells (the ciliated columnar epithelium of the bronchus, the alveolar epithelium, the exocrine gland of the bronchus, etc.) of the lung, and is broadly classified into one containing or not containing a bronchioloalveolar type (BAC) component.

In the present invention, the assessment means that a cancer lesion derived from a lung cancer patient is differentially evaluated or assayed to be squamous cell carcinoma or adenocarcinoma.

Examples of the biological sample used in the present invention include a biopsy specimen and a resected specimen collected from a lesion in a lung cancer patient to be assessed. In the case of assaying the biological sample at a nucleic acid level, RNA extracts are prepared, and in the case of assaying the sample at a protein level, protein extracts are prepared.

Any method known in the art can be used as a method for extracting RNA from the biological sample. Specific examples thereof can include Ambion RiboPure kit (manufactured by Life Technologies Corp.), miRNeasy (manufactured by Qiagen N.V.), and RNeasy (manufactured by Qiagen N.V.). Of them, miRNeasy kit manufactured by Qiagen N.V. is preferably used.

In the present specification, the term "nucleic acid" or "polynucleotide" means DNA or RNA. The "DNA" encompasses not only double-stranded DNA but each single-stranded DNA as a sense strand and an antisense strand constituting the double-stranded DNA. Thus, the DNA encompasses, for example, double-stranded genomic DNA, single-stranded cDNA, and single-stranded DNA having a sequence complementary to the DNA. The "RNA" includes all of total RNA, mRNA, rRNA, and synthetic RNA.

In the present invention, transcription products of DNAs consisting of nucleotide sequences represented by SEQ ID NOs: 1 to 213 (human genomic DNAs each consisting of a transcription start site and 100 bases located immediately downstream thereof) have been confirmed, as shown in Examples, to significantly differ in their expression levels (transcriptional activity) between squamous cell carcinoma and adenocarcinoma as a result of comprehensively analyzing the expression statuses of DNAs each comprising a transcription start site and 100 or more downstream bases on the genome by use of the CAGE (cap analysis gene expression) analysis method on squamous cell carcinoma (poorly differentiated lung squamous cell carcinoma) specimens and adenocarcinoma (lung adenocarcinoma free of a BAC component) specimens. Specifically, these transcription products were extracted by differential analysis on the transcriptional activity of RNA between a profile group derived from clinical specimens obtained from subjects "squamous cell carcinoma" and a profile group derived from clinical specimens obtained from subjects "adenocarcinoma" using R/Bioconductor edgeR package (Bioinformatics. 2010 Jan. 1; 26 (1): 139-40) with a threshold set to FDR (false discovery rate) of 1%.

Thus, an expression product of (or encoded by) DNA comprising a base at an arbitrary position (transcription start point) in the transcription start site and one or more bases located immediately downstream thereof in any of the nucleotide sequences represented by SEQ ID NOs: 1 to 213 (hereinafter, this DNA is referred to as "DNA containing a transcription start point in SEQ ID NOs: 1 to 213") (hereinafter, this expression product is referred to as the "expression product of the present invention") can serve as a biomarker for differentially assessing a lesion as lung squamous cell carcinoma or lung adenocarcinoma, specifically, differentially assessing lung cancer as squamous cell carcinoma or adenocarcinoma, further as poorly differentiated squamous cell carcinoma or adenocarcinoma, and further as poorly differentiated squamous cell carcinoma or adenocarcinoma free of a BAC component. The expression product of the DNA containing a transcription start point in SEQ ID NOs: 1 to 5 is a marker whose expression level is increased in lung adenocarcinoma. The expression product of the DNA containing a transcription start point in SEQ ID NOs: 6 to 213 is a marker whose expression level is decreased in lung adenocarcinoma.

In the present invention, the "transcription start site" refers to a region containing transcription start points. The transcription start points from a particular promoter are not limited to single bases and may be bases located at a plurality of positions downstream of the promoter on the genome. In the present specification, the region containing these plurality of transcription start points is referred to as a transcription start site. More specifically, the transcription start site is a region between a transcription start point positioned closest to the 5' end and a transcription start point positioned closest to the 3' end, among the plurality of transcription start points. In each of the nucleotide sequences represented by SEQ ID NOs: 1 to 213, the transcription start site is a 5'-terminal base region which corresponds to a region wherein both ends thereof are defined by a base at position 1 (5' end) and the 101st base counted from the 3' end. In other words, each of the nucleotide sequences represented by SEQ ID NOs: 1 to 213 is indicated by the transcription start site and 100 bases following the transcription start point positioned closest to the 3' end in the transcription start site. In the present specification, such a transcription start site is also referred to as a "transcription start site shown in SEQ ID NOs: 1 to 213".

The position of the transcription start site shown in SEQ ID NOs: 1 to 213 on the genome, and gene information related thereto, etc., are as shown later in Tables 1-1 to 1-9.

In the present invention, the DNA to be assayed for the expression level of the expression product comprises a base at an arbitrary position (transcription start point) in the transcription start site and a nucleotide sequence of one or more bases located immediately downstream thereof in any of nucleotide sequences represented by SEQ ID NOs: 1 to 213.

In this context, the number of bases in the nucleotide sequence immediately downstream thereof can be any number which allows the expression product to be identified. Examples of the number of these bases include 1 or more bases, 5 or more bases, 10 or more bases, 15 or more bases, 20 or more bases, 25 or more bases, 30 or more bases, 40 or more bases, and 50 or more bases. Also, examples of the number of the bases include 10 or less bases, 15 or less bases, 20 or less bases, 25 or less bases, 30 or less bases, 40 or less bases, 50 or less bases, and 100 or less bases.

The downstream bases can be any downstream moiety up to approximately 100 bases for securing the accuracy of assay based on hybridization or PCR, though this is not particularly required for CAGE assay. A length of at least 20 or more bases in the DNA consisting of the transcription start site and 100 bases downstream thereof can be identified with high probability even in an experimental system targeting the whole genome.

The DNA also encompasses DNA having a nucleotide sequence substantially identical to the nucleotide sequence of the DNA as long as its expression product can serve as a biomarker for discriminating between lung squamous cell carcinoma and lung adenocarcinoma. In this context, the substantially identical nucleotide sequence means that the nucleotide sequence has 90% or higher, preferably 95% or higher, more preferably 98% or higher identity with any of the nucleotide sequences represented by SEQ ID NOs: 1 to 213 when searched using, for example, a homology calculation algorithm NCBI BLAST under conditions involving expected value=10, gap accepted, filtering=ON, match score=1, and mismatch score=−3.

The expression product of the present invention is capable of discriminating between lung squamous cell carcinoma and lung adenocarcinoma by determining the expression level of this expression product alone or combined with the other expression product(s) of the present invention. Among others, the expression products of DNAs containing transcription start points in SEQ ID NO: 2, SEQ ID NO: 3, SEQ ID NO: 5, and SEQ ID NO: 7 permit classification with 100% specificity and 100% sensitivity when the thresholds shown in Table 2 are established. Specifically, the expression level of even only one of these expression products achieves reliable discrimination.

In the case of confirming the expression levels of a plurality of expression products in combination, the number thereof and the contents regarding the combination can be appropriately selected. The expression products of any two or more of the DNAs containing a transcription start point in SEQ ID NOs: 1 to 213 may be combined with each other. Alternatively, the expression product of at least one DNA containing a transcription start point in SEQ ID NOs: 1 to 213 may be combined with an expression product of DNA consisting of any of the other nucleotide sequences as long as this combination can contribute to the assessment of the present invention.

Examples of the expression product of the present invention include a transcription product and a translation product expressed from the DNA. Specific examples of the transcription product include RNA transcribed from the DNA, preferably mRNA. Specific examples of the translation product include a protein encoded by the RNA. Among the expression products of DNAs containing a transcription start point in SEQ ID NO: 2, SEQ ID NO: 3, SEQ ID NO: 5, and SEQ ID NO: 7, by which the expression level of even only one of these expression products achieves reliable discrimination as described above, for example, a protein expressed from DNA containing a transcription start point in SEQ ID NO: 3 has been identified as "ST6GALNAC1" (alpha-N-acetyl-neuraminyl-2,3-beta-galactosyl-1,3)-N-acetylgalactosaminide alpha-2,6-sialyltransferase 1; UniProtKB/Swiss-Prot: SIA7A_HUMAN, Q9NSC7), and a protein expressed from DNA containing a transcription start point in SEQ ID NO: 7 has been identified as "SPATS2" (spermatogenesis associated, serine-rich 2; UniProtKB/Swiss-Prot: SPAS2_HUMAN, Q86XZ4).

As shown in Table 1-1 mentioned later, the transcription product of the DNA consisting of the nucleotide sequence represented by SEQ ID NO: 3 is specifically expressed in adenocarcinoma, and the transcription product of the DNA consisting of the nucleotide sequence represented by SEQ ID NO: 7 is specifically expressed in squamous cell carcinoma. Therefore, ST6GALNAC1 serves as an adenocarcinoma marker, and SPATS2 serves as a squamous cell carcinoma marker. The combination of these markers is very useful for the differentiation between adenocarcinoma and squamous cell carcinoma. Furthermore, these markers can also be appropriately combined with a protein marker, such as P40, CK5, CK6, DSG3 (desmoglein-3), TTF-1 (thyroid transcription factor-1), or napsin A, which has heretofore been used in the differentiation of squamous cell carcinoma or adenocarcinoma, to thereby further improve the differentiation accuracy thereof. Preferred examples of the combination include combinations of two markers: TTF-1/ST6GALNAC1, CK5/ST6GALNAC1, DSG3/ST6GALNAC1, CK5/SPATS2, DSG3/SPATS2, p40/ST6GALNAC1, ST6GALNAC1/SPATS2, napsin A/ST6GALNAC1, and p40/SPATS2, more preferably a combination of two markers: TTF-1/ST6GALNAC1, even more preferably combinations of three markers: ST6GALNAC1/TTF-1/CK5, ST6GALNAC1/TTF-1/DSG3, ST6GALNAC1/TTF-1/p40, ST6GALNAC1/SPATS2/DSG3, ST6GALNAC1/SPATS2/CK5, and ST6GALNAC1/SPATS2/p40.

The target in the assay or detection of the expression product also encompasses, for example, cDNA artificially synthesized from the RNA, DNA encoding the RNA, a protein encoded by the RNA, a molecule interacting with the protein, a molecule interacting with the RNA, or a molecule interacting with the DNA. In this context, examples of the molecule interacting with the RNA, the DNA, or the protein include DNA, RNA, proteins, polysaccharides, oligosaccharides, monosaccharides, lipids, fatty acids, and phosphorylation products, alkylation products, or glycosylation products thereof, and complexes of any of these molecules.

The expression level collectively means the expression amount and activity of the expression product.

The method for measuring the expression level of RNA, cDNA, or DNA to be assayed can be selected from nucleic acid amplification methods typified by PCR using DNA primers hybridizing thereto, real-time RT-PCR, SmartAmp, and LAMP, hybridization methods (DNA chips, DNA microarrays, dot blot hybridization, slot blot hybridization, Northern blot hybridization, etc.) using nucleic acid probes hybridizing thereto, sequencing methods, and combinations of these methods.

In this context, the probe or the primer for use in the assay corresponds to a primer for specifically recognizing and amplifying the expression product of the present invention (transcription product) or a nucleic acid derived therefrom, or a probe for specifically detecting the RNA or a nucleic acid derived therefrom. These can be designed on the basis of the nucleotide sequences represented by SEQ ID NOs: 1 to 213. In this context, the phrase "specifically recognizing" means that substantially only the expression product of the present invention (transcription product) or a nucleic acid derived therefrom can be detected, for example, in Northern blot, and substantially the detected matter or the product can be determined as the transcription product or a nucleic acid derived therefrom, for example, in RT-PCR, in such a way that substantially only the nucleic acid is formed.

Specifically, an oligonucleotide comprising a given number of nucleotides complementary to the DNA comprising any of the nucleotide sequences represented by SEQ ID NOs: 1 to 213 or a complementary strand thereof can be used. In this context, the "complementary strand" refers to another strand against one strand of double-stranded DNA composed of A:T (U for RNA) and G:C base pairs. The term "complementary" is not limited by a completely complementary sequence in a region with the given number of consecutive nucleotides and may only have preferably 80% or higher, more preferably 90% or higher, even more preferably 95% or higher nucleotide sequence identity. The nucleotide sequence identity can be determined by an algorithm such as BLAST described above.

For use as a primer, such an oligonucleotide is not particularly limited as long as the oligonucleotide is capable of specific annealing and strand elongation. Examples thereof include oligonucleotides usually having a chain length of, for example, 10 or more bases, preferably 15 or more bases, more preferably 20 or more bases, and, for example, 100 or less bases, preferably 50 or less bases, more preferably 35 or less bases. For use as a probe, the oligonucleotide is not particularly limited as long as the oligonucleotide is capable of specific hybridization. An oligonucleotide having at least a portion or the whole sequence of the DNA comprising any of the nucleotide sequences represented by SEQ ID NOs: 1 to 213 (or a complementary strand thereof) and having a chain length of, for example, 10 or more bases, preferably 15 or more bases, and, for example, 100 or less bases, preferably 50 or less bases, more preferably 25 or less bases is used.

In this context, the "oligonucleotide" can be DNA or RNA and may be synthetic or natural. The probe for use in hybridization is usually labeled and then used.

For example, in the case of utilizing Northern blot hybridization, first, probe DNA is labeled with a radioisotope, a fluorescent material, or the like, and the obtained labeled DNA is subsequently hybridized with biological sample-derived RNA transferred to a nylon membrane or the like according to a routine method. Then, the formed double strand of the labeled DNA and the RNA can be used to detect and measure a signal derived from the label.

In the case of utilizing RT-PCR, first, cDNA is prepared from biological sample-derived RNA according to a routine method. This cDNA is used as a template and hybridized with a pair of primers (a forward strand binding to the cDNA (− strand) and a reverse strand binding to the + strand) prepared so as to be capable of amplifying the target expression product of the present invention (in this case, a transcription product). Then, PCR is performed according to a routine method, and the obtained amplified double-stranded DNA is detected. The detection of the amplified double-stranded DNA can employ, for example, a method which involves detecting labeled double-stranded DNA produced by PCR described above using primers labeled in advance with RI, a fluorescent material, or the like.

In the case of measuring the expression level of mRNA in a specimen using a DNA microarray, an array in which at least one nucleic acid (cDNA or DNA) derived from the expression product of the present invention (in this case, a transcription product) is immobilized on a support is used. Labeled cDNA or cRNA prepared from the mRNA is allowed to bind onto the microarray. The mRNA expression level can be measured by detecting the label on the microarray.

The nucleic acid to be immobilized on the array can be a nucleic acid capable of specific hybridization (i.e., hybridization substantially only to the nucleic acid of interest) under stringent conditions and may be, for example, a nucleic acid having the whole sequence of the expression product of the present invention (transcription product) or may be a nucleic acid consisting of a partial sequence thereof. In this context, examples of the "partial sequence" include a nucleic acid consisting of at least 15 to 25 bases.

In this context, examples of the stringent conditions can typically include washing conditions on the order of "1×SSC, 0.1% SDS, 37° C." and can include more stringent hybridization conditions on the order of "0.5×SSC, 0.1% SDS, 42° C." and even more stringent hybridization conditions on the order of "0.1×SSC, 0.1% SDS, 65° C.". The hybridization conditions are described in, for example, J. Sambrook et al., Molecular Cloning: A Laboratory Manual, Third Edition, Cold Spring Harbor Laboratory Press (2001).

Examples of the sequencing method include CAGE, TSS-seq, RNA-seq, DGE, and SAGE. CAGE is preferred.

In the case of measuring the expression level by use of CAGE, this measurement can be carried out according to a method described later in Examples.

In the case of assaying the protein (translation product) encoded by the DNA containing a transcription start point in SEQ ID NOs: 1 to 213, the molecule interacting with the protein, the molecule interacting with the RNA, or the molecule interacting with the DNA, a method such as protein chip analysis, immunoassay (e.g., an immunohistochemical analysis method (immunohistological staining method), and ELISA), one-hybrid method (PNAS 100, 12271-12276 (2003)), or two-hybrid method (Biol. Reprod. 58, 302-311 (1998)) can be used and can be appropriately selected according to the target.

In the case of assaying, for example, the protein used as a target, this assay is carried out by contacting an antibody against the expression product of the present invention (in this case, a translation product) with the biological sample, detecting the antibody-bound polypeptide in the sample, and measuring the level thereof. According to, for example, Western blot, the antibody described above is used as a primary antibody. Then, for example, radioisotope-, fluorescent material- or enzyme-labeled antibody binding to the primary antibody is used as a secondary antibody to label the primary antibody. A signal derived from such a labeling material is measured using a radiation counter, a fluorescence detector, or the like.

The antibody against the translation product may be a polyclonal antibody or may be a monoclonal antibody. These antibodies can be produced according to methods known in the art. Specifically, the polyclonal antibody can be obtained according to a routine method from the serum of an immunized animal obtained by immunizing a nonhuman animal (e.g., a rabbit) with a protein expressed in *E. coli* or the like and purified according to a routine method or with a partial polypeptide of the protein synthesized according to a routine method.

On the other hand, the monoclonal antibody can be obtained from hybridoma cells prepared by immunizing a nonhuman animal (e.g., a mouse) with a protein expressed in *E. coli* or the like and purified according to a routine method or with a partial polypeptide of the protein and fusing the obtained spleen cells with myeloma cells.

In the case of conducting an immunohistochemical analysis method, the biological sample isolated from a patient is fixed in formalin by a routine method, then embedded in paraffin, and sliced into a tissue section, which is attached to slide glass. The resultant is preferably used as a section sample. An antibody labeled with an enzyme such as alkaline phosphatase or peroxidase can be used as the secondary antibody. Highly sensitive detection is preferably performed using, for example, Vector ABC, DAKO EnVision detection system or the like.

In this way, the expression level of the expression product of the present invention in the biological sample collected from a cancer lesion in a lung cancer patient is measured. The lesion is differentially assessed as squamous cell carcinoma or adenocarcinoma on the basis of the expression level. Specifically, the detected expression level of the expression product of the present invention is compared with a control level for the assessment.

In this context, examples of the "control level" include the expression level of the expression product in a lesion tissue isolated from an adenocarcinoma patient or in a normal tissue isolated from a lung cancer patient, and the expression level of the expression product in a healthy individual group having no lung cancer.

For example, when the expression level of the expression product in the lesion of the subject patient is close to the expression level in an lesion tissue isolated from an adenocarcinoma patient, a normal tissue, or a tissue derived from a healthy individual, when the expression level of the expression product in the lesion of the subject patient belongs to within the range of this expression level, or when the expression level of the expression product in the lesion of the subject patient is significantly higher (or lower) than this expression level, the lung cancer lesion of the patient can be assessed as having a low possibility of being squamous cell carcinoma.

The assessment of lung cancer lesion according to the present invention can also be conducted on the basis of increase or decrease in the expression level of the expression product of the present invention. In this case, a reference value (threshold level) is established on the basis of the control level, for example, the expression level of the expression product derived from a normal tissue, a lesion tissue isolated from an adenocarcinoma patient, or a tissue of a healthy individual. The assessment can be conducted by comparing the expression level of the expression product in the patient-derived biological sample with the reference value (e.g., a range of ±2S.D. is used as a tolerance). For example, when the expression level of the expression product in the patient-derived biological sample is higher or lower than the threshold level, the lesion of the patient can be assessed as having a low possibility of being squamous cell carcinoma.

According to the method of the present invention, the histological type of lung cancer is easily assessed even for a microscopic specimen such as a biopsy specimen. When the lesion is confirmed to have a possibility of being non-squamous cell carcinoma, the administration of a low toxic anticancer agent (pemetrexed) or the administration of a molecular targeting therapeutic drug (bevacizumab) or the like found to confer extra therapeutic effects by combined use with an anticancer agent can be performed as treatment of the first-line choice. When the lesion is diagnosed as squamous cell carcinoma, treatment with an anticancer agent other than pemetrexed and bevacizumab is performed, or the patient become a subject of clinical trials of antibody therapy or molecular targeting therapy targeting squamous cell carcinoma.

The testing kit for assessing lesion of lung cancer according to the present invention comprises a testing reagent for measuring the expression level of the expression product of the present invention in the biological sample isolated from a patient. Specific examples thereof include a reagent for nucleic acid amplification or hybridization comprising an oligonucleotide specifically binding (hybridizing) to the expression product of the present invention (transcription product) or the like, and a reagent for immunoassay comprising an antibody recognizing the expression product of the present invention (translation product). The oligonucleotide, the antibody, or the like included in the kit can be obtained by a method known in the art as mentioned above.

The testing kit can further comprise a labeling reagent, a buffer solution, a chromogenic substrate, a secondary antibody, a blocking agent, and equipment or a control necessary for the test, in addition to the antibody or the nucleic acid.

EXAMPLES

Example 1 Extraction and Validation of Transcription Start Site which Permits Differentiation Between Adenocarcinoma and Squamous Cell Carcinoma (1) Acquisition of Test Sample Specimens (samples) were acquired by surgical resection, needle biopsy, and the like from lung cancer lesions. The samples used were 15 specimens (3 adenocarcinoma (adenocarcinoma free of a BAC component) specimens and 12 poorly differentiated squamous cell carcinoma) as samples for transcription start site extraction and 20 specimens (10 adenocarcinoma (adenocarcinoma free of a BAC component) specimens and 10 poorly differentiated squamous cell carcinoma specimens) as samples for validation.

(2) Preservation and Preparation of Sample

Each harvested tissue section was appropriately frozen and preserved at −80° C. The preserved tissue section was placed in a 2 mL microtube such that the amount of the tissue section was 50 mg or less. QIAzol (manufactured by Qiagen N.V.) was added to the microtube, and one zirconia bead was placed therein. After hermetically sealing of the tube, the tissue section was lysed by penetration treatment using TissueLyser (manufactured by Qiagen N.V.).

(3) Preparation of RNA

Each sample thus treated by lysis and extraction was subjected to RNA preparation using miRNeasy mini kit (manufactured by Qiagen N.V.) according to the protocol included in the kit. The RNA thus prepared was assayed for ultraviolet absorption (230, 260, and 280 nm) using a spectrophotometer, and 260/230 and 260/280 ratios were calculated to test the quality of the RNA. Furthermore, the RNA was electrophoresed using BioAnalyzer RNA nano chip (manufactured by Agilent Technologies Inc.), and RIN values indicating the degree of RNA degradation were calculated to test the degree of degradation of the RNA.

(4) Preparation of CAGE Library

5 μg of each purified RNA was used to prepare a CAGE library by no-amplification non-tagging CAGE (see "Cell Technology, suppl. Purpose-specific advanced methods of next-generation sequencers", edited by Sumio Sugano and Yutaka Suzuki, Gakken Medical Shujunsha Co., Ltd., issued on Sep. 19, 2012), Part 3-3, "Comprehensive promoter analysis (no-amplification CAGE using Illumina sequencer)"). Specifically, the purified RNA was subjected to reverse transcription reaction. After purification, diol in the ribose was oxidized with sodium periodate for conversion to aldehyde. The aldehyde group was biotinylated by the addition of biotin hydrazide. After digestion of the single-stranded RNA moiety with RNase I and purification, only the biotinylated RNA/cDNA double strand was allowed to bind to the surface of avidin magnetic beads, and cDNA was released by RNase H digestion and heat treatment and recovered. Both ends of the recovered cDNA were linked to adaptors necessary for sequencing, followed by sequencing using HiSeq 2500 (manufactured by Illumina, Inc.). The standard conditions of AMPure XP (manufactured by Beckman Coulter, Inc.) used in purification, buffer solution replacement, and the like in this step are conditions under which, in the case of double strand, nucleic acids of 100 or more bases long are recovered. The CAGE library produced by this step which adopted the conditions consisted of double-stranded DNAs each having a chain length of 100 or more bases.

(5) RNA Expression Analysis i) Preparation of Reference Transcription Start Site The reference transcription start sites were set to approximately 180,000 transcription start sites defined on the human reference genome hg19 among the transcription start sites identified in the profiling project "FANTOM5" (paper submitted) assaying in a genome-wide manner the activity of transcription start points as to human samples as many as approximately 1,000 samples in total including human primary cultured cells, cell lines, and tissues, etc.

ii) Quantification of Transcriptional Activity

Reads obtained by sequencing were aligned against the human reference genome (hg19) using bwa (Bioinformatics. 2009 Jul. 15; 25 (14): 1754-60). Alignments were selected such that the mapping quality was 20 or more and the alignment starting position was located within the reference transcription start sites. The number of reads of each transcription start site was counted. Counts per million were calculated using the total number of reads in each library and a library size predicted by RLE (Genome Biol. 2010; 11 (10): R106).

(6) Results (A) Extraction of Transcription Start Sites Differing in Activity

Differential analysis was conducted on the thus-quantified transcriptional activity of each sample for transcription start site extraction between a profile group derived from clinical specimens obtained from subjects "adenocarcinoma (adenocarcinoma free of a BAC component)" and a profile group derived from clinical specimens obtained from subjects "poorly differentiated squamous cell carcinoma" using R/Bioconductor edgeR package (Bioinformatics. 2010 Jan. 1; 26 (1): 139-40). In short, this analysis is to statistically test whether an average expression level differs between two groups (equality of the average expression level is defined as null hypothesis, and assuming that this null hypothesis is true, the probability of producing assay results accidentally is calculated). The threshold was set to FDR (false discovery rate) of 1%. As a result, 213 DNAs containing transcription start sites having values smaller than this threshold were identified (Tables 1-1 to 1-9). This criterion is based on the statistical presumption that 99% of candidates extracted by the corresponding threshold have significant expression difference, and is stricter than the P value (probability of occurring accidentally provided that there is no expression difference) of 5% usually used widely.

TABLE 1-1

| SEQ ID NO | Chr. No. | Start position | Termination position | Strand | Gene name | Expression [Adenocarcinoma/ squamous cell carcinoma] | Average expression of all groups |
|---|---|---|---|---|---|---|---|
| 1 | chr5 | 58883433 | 58883475 | − | | 117.4456124 | 57.53260484 |
| 2 | chr9 | 136130661 | 136130725 | − | | 86.19474286 | 2.17782974 |
| 3 | chr17 | 74639730 | 74639811 | − | ST6GALNAC1 | 40.54692632 | 25.20981831 |
| 4 | chr1 | 223853355 | 223853378 | − | CAPN8 | 27.2525015 | 23.55940925 |
| 5 | chr13 | 32519986 | 32520015 | + | | 11.50999634 | 16.16428466 |
| 6 | chr6 | 62529219 | 52529236 | + | RP1-152L7.5 | 0.20312783 | 6.013946212 |
| 7 | chr12 | 49761147 | 49761166 | + | SPATS2 | 0.183840921 | 4.614891149 |
| 8 | chr8 | 49833978 | 49833996 | − | SNAI2 | 0.18030751 | 25.81533177 |
| 9 | chr14 | 52535757 | 52535831 | − | NID2 | 0.177747311 | 15.91094231 |
| 10 | chr3 | 194406603 | 194406619 | + | FAM43A | 0.173665251 | 12.4294564 |
| 11 | chr19 | 55919144 | 55919163 | − | UBE2S | 0.171752891 | 149.8412682 |
| 12 | chr15 | 92396920 | 92396987 | + | SLCO3A1 | 0.168147878 | 15.68697966 |

TABLE 1-1-continued

| | | | | | | | |
|---|---|---|---|---|---|---|---|
| 13 | chr6 | 46293378 | 46293415 | − | RCAN2 | 0.161953809 | 5.977935719 |
| 14 | chr4 | 109090075 | 109090095 | − | LEF1 | 0.154844698 | 3.598793037 |
| 15 | chr22 | 22764110 | 22764121 | + | IGLV1-40 | 0.153315437 | 230.9741701 |
| 16 | chr4 | 159091792 | 159091884 | − | FAM198B | 0.153048999 | 7.241616206 |
| 17 | chr7 | 47576906 | 47576950 | − | | 0.151309467 | 4.69804584 |
| 18 | chr5 | 1008910 | 1008924 | + | NKD2 | 0.147086399 | 13.43860406 |
| 19 | chr2 | 152214098 | 152214115 | + | TNFAIP6 | 0.145777736 | 24.54414747 |
| 20 | chr2 | 89156823 | 89156840 | − | IGKC | 0.145549098 | 30.09656175 |
| 21 | chr8 | 91997427 | 91997504 | − | RP11-122A3.2 | 0.140796978 | 5.485439033 |
| 22 | chr3 | 45267760 | 45267826 | − | TMEM158 | 0.139328756 | 7.200919978 |
| 23 | chr19 | 531713 | 531748 | + | CDC34 | 0.138357923 | 10.71283356 |
| 24 | chr3 | 170136642 | 170136663 | + | CLDN11 | 0.12953024 | 2.434330802 |
| 25 | chr14 | 52118694 | 52118708 | + | FRMD6 | 0.126865016 | 0.681628217 |

| SEQ ID NO | Ave. expression level of adenocarcinoma group | Ave. expression level of squamous cell carcinoma group | Pvalue | FDR |
|---|---|---|---|---|
| 1 | 71.76299811 | 0.61103175 | 3.68E−05 | 0.008164349 |
| 2 | 2.714414263 | 0.031491645 | 3.13E−05 | 0.007057936 |
| 3 | 31.31916843 | 0.77241782 | 8.80E−06 | 0.002523928 |
| 4 | 29.18156536 | 1.070784836 | 9.03E−06 | 0.002557071 |
| 5 | 19.77582006 | 1.718143036 | 3.81E−05 | 0.008406514 |
| 6 | 3.369909561 | 16.59009282 | 1.75E−05 | 0.004466275 |
| 7 | 2.444461199 | 13.29661095 | 2.63E−05 | 0.006124957 |
| 8 | 13.52142966 | 74.99094017 | 2.69E−05 | 0.006202132 |
| 9 | 8.264596694 | 46.49632476 | 3.59E−06 | 0.001237687 |
| 10 | 6.368721129 | 36.67239748 | 2.07E−05 | 0.005035605 |
| 11 | 76.27591767 | 444.1026705 | 7.80E−06 | 0.002294397 |
| 12 | 7.885165992 | 46.89423435 | 7.58E−06 | 0.002242786 |
| 13 | 2.937676013 | 18.13897454 | 2.76E−05 | 0.006285548 |
| 14 | 1.720579593 | 11.11164681 | 1.47E−05 | 0.003850812 |
| 15 | 109.7525121 | 715.8608021 | 2.06E−05 | 0.005035605 |
| 16 | 3.437305741 | 22.45885806 | 1.14E−05 | 0.003108766 |
| 17 | 2.214185278 | 14.63348809 | 2.03E−05 | 0.005012873 |
| 18 | 6.222310459 | 42.30377847 | 7.89E−06 | 0.002304873 |
| 19 | 11.30050381 | 77.5187221 | 4.18E−05 | 0.009145817 |
| 20 | 13.84318482 | 95.11006949 | 3.45E−05 | 0.007693988 |
| 21 | 2.470378749 | 17.54568017 | 2.79E−06 | 0.001073502 |
| 22 | 3.221234013 | 23.11966384 | 1.08E−05 | 0.002956243 |
| 23 | 4.770745333 | 34.48118646 | 1.90E−05 | 0.004758972 |
| 24 | 1.038518871 | 8.017578527 | 2.29E−05 | 0.00542093 |
| 25 | 0.286822772 | 2.260849996 | 2.17E−05 | 0.005226548 |

TABLE 1-2

| SEQ ID NO | Chr. No. | Transcription start site (TSS) | | | | Expression [Adenocarcinoma/ squamous cell carcinoma] | Average expression of all groups |
|---|---|---|---|---|---|---|---|
| | | Start position | Termination position | Strand | Gene name | | |
| 26 | chr16 | 76005170 | 76005197 | − | CSPG4 | 0.125369565 | 8.364983684 |
| 27 | chr19 | 531750 | 531767 | + | CDC34 | 0.122560386 | 4.710057695 |
| 28 | chr5 | 38258654 | 38258667 | − | EGFLAM | 0.120610361 | 2.432073251 |
| 29 | chr8 | 49833948 | 49833973 | − | SNAI2 | 0.119983496 | 4.293574167 |
| 30 | chr11 | 19366758 | 19366812 | + | | 0.118441115 | 2.738476802 |
| 31 | chr1 | 8483878 | 8483907 | − | RERE | 0.118153839 | 6.830907904 |
| 32 | chr2 | 89157015 | 89157033 | − | IGKC | 0.117729832 | 26.55036588 |
| 33 | chr22 | 38713428 | 38713446 | − | CSNKIE | 0.117156827 | 3.815319033 |
| 34 | chr5 | 168727941 | 168727995 | − | SLIT3 | 0.117017264 | 1.593123081 |
| 35 | chr10 | 116164244 | 116164268 | − | AFAP1L2 | 0.114054544 | 17.90924887 |
| 36 | chr14 | 106967526 | 106967551 | − | IGHV1-46 | 0.112938698 | 407.9318873 |
| 37 | chr18 | 10454594 | 10454645 | + | APCDD1 | 0.112573616 | 23.1192467 |
| 38 | chr17 | 39780819 | 39780835 | − | KRT17 | 0.111211511 | 77.95071184 |
| 39 | chr11 | 2292226 | 2292270 | − | ASCL2 | 0.109408341 | 2.506071313 |
| 40 | chr5 | 42756913 | 42756963 | + | CCDC152 | 0.106615796 | 2.087536303 |
| 41 | chr19 | 10121144 | 10121155 | − | COL5A3 | 0.105429771 | 1.014058651 |
| 42 | chr3 | 101498269 | 101498341 | + | NXPE3 | 0.104047065 | 1.803070531 |
| 43 | chr5 | 86180719 | 86180730 | − | CTD-2161E19.1 | 0.102994276 | 3.828847736 |
| 44 | chr17 | 30813576 | 30813637 | + | CDK5R1 | 0.102192165 | 1.284094573 |
| 45 | chr5 | 158527346 | 158527362 | − | RBF1 | 0.099825184 | 1.177890362 |
| 46 | chr1 | 151032860 | 151032918 | + | | 0.096522138 | 9.51171703 |
| 47 | chr2 | 101618965 | 101619066 | + | RPL31 | 0.095678554 | 1.960657036 |
| 48 | chr3 | 154797428 | 154797450 | + | MME | 0.094537076 | 1.017365163 |
| 49 | chr14 | 106110903 | 106110942 | − | IGHG2 | 0.093442046 | 9.804535328 |

TABLE 1-2-continued

| | | | | | | | |
|---|---|---|---|---|---|---|---|
| 50 | chr22 | 23054857 | 23054874 | + | IGLV3-21 | 0.09281564 | 1730.814494 |
| 51 | chr1 | 6773527 | 6777357 | + | IL12RB2 | 0.88821332 | 2.910680342 |

| SEQ ID NO | Ave. expression level of adenocarcinoma group | Ave. expression level of squamous cell carcinoma group | Pvalue | FDR |
|---|---|---|---|---|
| 27 | 1.936821893 | 15.8030009 | 2.26E-05 | 0.005369345 |
| 28 | 0.989358583 | 8.202931922 | 9.68E-06 | 0.002708794 |
| 29 | 1.740476411 | 14.50596519 | 1.45E-06 | 0.000639836 |
| 30 | 1.10040734 | 9.290754647 | 9.61E-06 | 0.002704007 |
| 31 | 2.740355759 | 23.19311649 | 3.38E-06 | 0.001192707 |
| 32 | 10.62519855 | 90.25103519 | 1.24E-05 | 0.003322381 |
| 33 | 1.521797497 | 12.98940518 | 1.74E-05 | 0.004466275 |
| 34 | 0.634925526 | 5.425913299 | 4.58E-05 | 0.009957508 |
| 35 | 7.013479305 | 61.49232711 | 5.04E-07 | 0.000260903 |
| 36 | 158.6745109 | 1404.961393 | 8.78E-07 | 0.000417664 |
| 37 | 8.972719927 | 79.70535378 | 2.56E-05 | 0.006008152 |
| 38 | 29.99979305 | 269.754387 | 2.99E-06 | 0.001123754 |
| 39 | 0.953598851 | 8.715961158 | 4.89E-06 | 0.001600963 |
| 40 | 0.780126493 | 7.317175543 | 1.46E-06 | 0.000639836 |
| 41 | 0.375995414 | 3.566311698 | 2.84E-05 | 0.006437771 |
| 42 | 0.662356134 | 6.365928117 | 5.04E-06 | 0.001638554 |
| 43 | 1.396444033 | 13.55846255 | 1.29E-06 | 0.000578018 |
| 44 | 0.465741495 | 4.557506887 | 8.71E-06 | 0.002512083 |
| 45 | 0.420149577 | 4.208853501 | 2.27E-06 | 0.00091831 |
| 46 | 3.311805945 | 34.31136137 | 2.70E-06 | 0.001048738 |
| 47 | 0.67834997 | 7.089885301 | 2.02E-06 | 0.000840353 |
| 48 | 0.348941864 | 3.691058358 | 3.46E-06 | 0.001211401 |
| 49 | 3.334463031 | 35.68482452 | 1.73E-06 | 0.000747836 |
| 50 | 585.7618355 | 6311.02513 | 1.79E-06 | 0.000758421 |
| 51 | 0.95378626 | 10.73825667 | 3.57E-07 | 0.000195936 |

TABLE 1-3

| SEQ ID NO | Transcription start site (TSS) | | | | Expression [Adenocarcinoma/ squamous cell carcinoma] | Average expression of all groups |
|---|---|---|---|---|---|---|
| | Chr. No. | Start position | Termination position | Strand | Gene name | | |
| 52 | chr17 | 63556428 | 63556442 | − | AXIN2 | 0.08789334 | 10.42261175 |
| 53 | chr16 | 88449385 | 88449440 | + | | 0.087642495 | 1.631021592 |
| 54 | chr10 | 114154517 | 114164559 | + | | 0.087186583 | 8.155129508 |
| 55 | chr2 | 89156977 | 89156984 | − | IGKC | 0.084163379 | 2.330903976 |
| 56 | chr20 | 49308048 | 49308084 | − | FAM65C | 0.083759351 | 0.755958839 |
| 57 | chr16 | 88449358 | 88449372 | + | | 0.083512551 | 1.150307337 |
| 58 | chr10 | 116164538 | 116164562 | − | AFAP1L2 | 0.082646743 | 0.916524273 |
| 59 | chr7 | 103630096 | 103630116 | − | RELN | 0.08256297 | 1.55994825 |
| 60 | chr3 | 87040003 | 87040018 | − | VGLL3 | 0.081892001 | 2.029704034 |
| 61 | chr14 | 106573756 | 106573760 | − | IGHV3-11 | 0.080280409 | 19.15498618 |
| 62 | chr2 | 207308275 | 207308295 | + | ADAM23 | 0.079958479 | 0.799493189 |
| 63 | chr18 | 7117813 | 7117843 | − | LAMA1 | 0.079820368 | 1.87555629 |
| 64 | chr22 | 23055620 | 23055631 | + | | 0.07981464 | 11.5326354 |
| 65 | chr1 | 53793705 | 53793719 | − | LRP8 | 0.078463875 | 3.576930969 |
| 66 | chr1 | 148928291 | 148928331 | + | RP11-14N7.2 | 0.077063738 | 21.07308887 |
| 67 | chr14 | 107170409 | 107170434 | − | IGHV1-69 | 0.076710918 | 2932.856991 |
| 68 | chr4 | 109090054 | 109090073 | − | LEF1 | 0.076667347 | 0.870358396 |
| 69 | chr3 | 154798096 | 154798115 | + | MME | 0.076124034 | 4.955030786 |
| 70 | chr4 | 109089965 | 109089977 | − | LEF1 | 0.075977223 | 0.694578889 |
| 71 | chr10 | 116164270 | 116164290 | − | AFAP1L2 | 0.073701321 | 4.412075993 |
| 72 | chr3 | 189507432 | 189507459 | + | TP63 | 0.073564988 | 5.762954168 |
| 73 | chr10 | 28966443 | 28966461 | − | BAMBI | 0.071989849 | 31.07096362 |
| 74 | chr4 | 109089995 | 109090012 | − | LEF1 | 0.071562822 | 1.555274279 |
| 75 | chr16 | 86600426 | 86600441 | + | FOXC2 | 0.071258884 | 1.766569708 |
| 76 | chr2 | 70995307 | 70995339 | − | ADD2 | 0.070232109 | 2.92281932 |
| 77 | chr17 | 71161140 | 71161174 | + | SSTR2 | 0.069347419 | 1.759393573 |

| SEQ ID NO | Ave. expression level of adenocarcinoma group | Ave. expression level of squamous cell carcinoma group | Pvalue | FDR |
|---|---|---|---|---|
| 52 | 3.388932437 | 38.55732899 | 5.29E-06 | |
| 53 | 0.529209165 | 6.0882713 | 3.28E-06 | 0.001163907 |
| 54 | 2.635847302 | 30.23225833 | 2.17E-05 | 0.005226548 |

TABLE 1-3-continued

| | | | | |
|---|---|---|---|---|
| 55 | 0.733835477 | 8.71917797 | 1.04E−05 | 0.002896072 |
| 56 | 0.237141751 | 2.831227189 | 2.25E−05 | 0.005369345 |
| 57 | 0.360050543 | 4.311334515 | 1.56E−05 | 0.004037656 |
| 58 | 0.284640341 | 3.444060001 | 3.57E−06 | 0.001237687 |
| 59 | 0.484096143 | 5.863356677 | 2.72E−05 | 0.006218432 |
| 60 | 0.626018871 | 7.64444469 | 2.43E−06 | 0.000975133 |
| 61 | 5.819941466 | 72.49516505 | 1.98E−07 | 0.000121752 |
| 62 | 0.242175392 | 3.028764379 | 1.22E−05 | 0.003296083 |
| 63 | 0.567383068 | 7.108249175 | 4.12E−05 | 0.009063941 |
| 64 | 3.488600232 | 43.70877606 | 5.23E−06 | 0.001666531 |
| 65 | 1.068077362 | 13.61234539 | 2.46E−05 | 0.005805863 |
| 66 | 6.206630404 | 80.53892273 | 3.84E−06 | 0.001314289 |
| 67 | 860.7844899 | 11221.147 | 7.66E−07 | 0.000372125 |
| 68 | 0.255336467 | 3.330446114 | 3.98E−06 | 0.001338574 |
| 69 | 1.445757181 | 18.9921251 | 1.05E−05 | 0.002910678 |
| 70 | 0.202361436 | 2.663448697 | 1.87E−05 | 0.004713437 |
| 71 | 1.255693931 | 17.03760424 | 8.10E−08 | 5.76E−05 |
| 72 | 1.637814921 | 22.26351116 | 5.21E−06 | 0.001666531 |
| 73 | 8.683480224 | 120.6208972 | 4.59E−07 | 0.00024346 |
| 74 | 0.432651914 | 6.045763735 | 4.16E−07 | 0.000223263 |
| 75 | 0.489806631 | 6.873622019 | 2.19E−06 | 0.000893101 |
| 76 | 0.801277255 | 11.40898758 | 1.27E−06 | 0.000574498 |
| 77 | 0.477573155 | 6.886675244 | 4.57E−08 | 3.52E−05 |

TABLE 1-4

| SEQ ID NO | Chr. No. | Start position | Termination position | Strand | Gene name | Expression [Adenocarcinoma/ squamous cell carcinoma] | Average expression of all groups |
|---|---|---|---|---|---|---|---|
| 78 | chr9 | 38424443 | 38424458 | − | IGFBPL1 | 0.068605286 | 3.733725472 |
| 79 | chr2 | 70995350 | 70995375 | − | ADD2 | 0.068418119 | 1.625876946 |
| 80 | chr19 | 4304585 | 4304627 | + | FSD1 | 0.06834565 | 0.570594158 |
| 81 | chr14 | 106733624 | 106733650 | − | IGHV1-24 | 0.068056168 | 447.0714092 |
| 82 | chr11 | 8932828 | 8932841 | + | AKIP1 | 0.067015744 | 1.026254009 |
| 83 | chr5 | 174151553 | 174151610 | + | MSX2 | 0.062483344 | 5.214864767 |
| 84 | chr5 | 150970816 | 150970899 | − | | 0.062409217 | 4.50401539 |
| 85 | chr4 | 109089901 | 109089930 | − | LEF1 | 0.062164305 | 3.832428637 |
| 86 | chr3 | 128712906 | 128712928 | − | KIAA1257 | 0.060145901 | 0.989340264 |
| 87 | chr14 | 107211459 | 107211478 | − | IGHV3-73 | 0.059710662 | 313.8304148 |
| 88 | chr6 | 123100853 | 123100874 | + | FABP7 | 0.058590232 | 0.971503444 |
| 89 | chr3 | 139258521 | 139258589 | − | RBP1 | 0.058208289 | 31.34819473 |
| 90 | chr4 | 183065793 | 183065864 | + | TENM3 | 0.057429732 | 2.892418765 |
| 91 | chr6 | 54711471 | 54711486 | + | FAM83B | 0.056091849 | 0.441946036 |
| 92 | chr9 | 23821808 | 23821827 | − | ELAVL2 | 0.05463255 | 0.798431489 |
| 93 | chr9 | 139964983 | 139964996 | − | SAPCD2 | 0.053900282 | 4.374907424 |
| 94 | chr7 | 96654133 | 96654150 | − | DLX5 | 0.052981944 | 0.974446891 |
| 95 | chr14 | 22918770 | 22918847 | + | TRDJ1 | 0.051583758 | 3.464015094 |
| 96 | chr1 | 2461692 | 2461710 | − | HES5 | 0.051086818 | 1.380304695 |
| 97 | chr15 | 83378614 | 83378634 | − | AP3B2 | 0.050242839 | 0.582896397 |
| 98 | chr14 | 106092169 | 106092199 | − | IGHG4 | 0.047564004 | 2.492537788 |
| 99 | chrX | 24665144 | 24665178 | − | PCYT1B | 0.047224957 | 0.329490476 |
| 100 | chr2 | 122660056 | 122660078 | + | | 0.047121934 | 0.749217673 |
| 101 | chr7 | 19157248 | 19157268 | − | TWIST1 | 0.047108441 | 6.850490686 |
| 102 | chrX | 153151586 | 153151644 | − | L1CAM | 0.046715283 | 2.023621466 |
| 103 | chr17 | 79860107 | 79860120 | + | NPB | 0.045910156 | 4.07515518 |

| SEQ ID NO | Ave. expression level of adenocarcinoma group | Ave. expression level of squamous cell carcinoma group | Pvalue | FDR |
|---|---|---|---|---|
| 78 | 1.004979022 | 14.64871127 | 2.61E−06 | 0.001030727 |
| 79 | 0.436687785 | 6.382633592 | 1.83E−06 | 0.000766785 |
| 80 | 0.153126125 | 2.240466287 | 3.02E−06 | 0.001124453 |
| 81 | 119.5778051 | 1757.045826 | 1.72E−08 | 1.50E−05 |
| 82 | 0.27118202 | 4.046541963 | 5.32E−06 | 0.001672132 |
| 83 | 1.303438223 | 20.86057094 | 1.06E−08 | 9.60E−06 |
| 84 | 1.124695026 | 18.02129685 | 1.97E−05 | 0.004913813 |
| 85 | 0.953985845 | 15.3461998 | 6.69E−10 | 1.10E−06 |
| 86 | 0.239825681 | 3.987398594 | 2.71E−05 | 0.006218432 |
| 87 | 75.63116168 | 1266.627427 | 7.78E−08 | 5.61E−05 |
| 88 | 0.230567132 | 3.935248693 | 2.90E−06 | 0.001105647 |
| 89 | 7.400534183 | 127.1388369 | 5.99E−12 | 1.84E−08 |
| 90 | 0.675401631 | 11.7604873 | 3.79E−09 | 4.37E−06 |

TABLE 1-4-continued

| | | | | |
|---|---|---|---|---|
| 91 | 0.101234199 | 1.804793387 | 4.59E−05 | 0.009957508 |
| 92 | 0.178987554 | 3.276207228 | 6.44E−06 | 0.001947713 |
| 93 | 0.969926473 | 17.99483123 | 4.12E−07 | 0.000223263 |
| 94 | 0.212999865 | 4.020234997 | 4.00E−06 | 0.001338574 |
| 95 | 0.740618949 | 14.35759968 | 7.60E−07 | 0.000372125 |
| 96 | 0.292753498 | 5.730509486 | 1.76E−06 | 0.000752412 |
| 97 | 0.121927845 | 2.426770605 | 1.30E−05 | 0.003457474 |
| 98 | 0.498023434 | 10.47059521 | 1.25E−07 | 7.98E−05 |
| 99 | 0.065439381 | 1.385694859 | 1.57E−05 | 0.004042101 |
| 100 | 0.148527347 | 3.151978976 | 4.31E−06 | 0.001430757 |
| 101 | 1.357736305 | 28.82150821 | 5.51E−08 | 4.11E−05 |
| 102 | 0.398252362 | 8.525097883 | 4.11E−08 | 3.22E−05 |
| 103 | 0.790320161 | 17.21449525 | 9.14E−08 | 6.12E−05 |

TABLE 1-5

| SEQ ID NO | Transcription start site (TSS) | | | | Expression ratio [Adenocarcinoma/ squamous cell carcinoma] |
|---|---|---|---|---|---|
| | Chr. No. | Start position | Termination position | Strand | Gene name |
| 104 | chr3 | 87040233 | 87040256 | − | VGLL3 | 0.045560173 |
| 105 | chr1 | 151032782 | 151032801 | + | | 0.043769778 |
| 106 | chr3 | 139258443 | 139258485 | − | RBP1 | 0.043028313 |
| 107 | chr2 | 89156940 | 89156955 | − | IGKC | 0.042518612 |
| 108 | chr8 | 107460147 | 107460207 | + | OXR1 | 0.042439886 |
| 109 | chr18 | 10454647 | 10454682 | + | APCDD1 | 0.041955516 |
| 110 | chr11 | 61276214 | 61276227 | + | LRRC10B | 0.041889345 |
| 111 | chr2 | 239148671 | 239148686 | − | HES6 | 0.040248345 |
| 112 | chr8 | 37351344 | 37351394 | − | RP11-150012.1 | 0.039989683 |
| 113 | chr22 | 43739340 | 43739385 | − | SCUBE1 | 0.039236076 |
| 114 | chr19 | 46580361 | 46580396 | − | IGFL4 | 0.039122736 |
| 115 | chr11 | 94439606 | 94439641 | + | AMOTL1 | 0.037199241 |
| 116 | chr14 | 106091272 | 106091292 | − | | 0.036776534 |
| 117 | chr4 | 4861385 | 4861398 | + | MSX1 | 0.03652176 |
| 118 | chr4 | 71384280 | 71384295 | + | AMTN | 0.036204608 |
| 119 | chr17 | 39742770 | 39742785 | + | | 0.03616918 |
| 120 | chr20 | 62669277 | 62669301 | + | LINC00176 | 0.035661368 |
| 121 | chr3 | 154798129 | 154798155 | + | MME | 0.035018429 |
| 122 | chr5 | 174151612 | 174151633 | + | MSX2 | 0.034820813 |
| 123 | chr2 | 237076069 | 237076110 | + | AC079135.1 | 0.034519305 |
| 124 | chr3 | 12045814 | 12045834 | + | SYN2 | 0.033221577 |
| 125 | chr8 | 17611447 | 17611490 | − | | 0.032590197 |
| 126 | chr12 | 52914170 | 52914185 | − | KRT5 | 0.032293886 |
| 127 | chr13 | 100634130 | 100634143 | + | ZIC2 | 0.030967646 |
| 128 | chr10 | 5567551 | 5567579 | + | CALML3 | 0.02971377 |
| 129 | chr1 | 11751748 | 11751798 | + | DRAXIN | 0.029545481 |

| SEQ ID NO | Average expression of all groups | Ave. expression level of adenorcinoma group | Ave. expression level of squamous cell carcinoma group | Pvalue | FDR |
|---|---|---|---|---|---|
| 104 | 2.497224 | 0.481179332 | 10.56140267 | 5.02E−09 | 5.00E−06 |
| 105 | 1.115783464 | 0.207805558 | 4.747695086 | 7.81E−07 | 0.000375688 |
| 106 | 57.97864917 | 10.64198991 | 247.3252862 | 9.88E−12 | 2.53E−08 |
| 107 | 15.29799393 | 2.779521741 | 65.37188268 | 4.85E−09 | 4.97E−06 |
| 108 | 0.887131085 | 0.160929408 | 3.791937793 | 8.18E−06 | 0.002374534 |
| 109 | 36.08307216 | 6.481654813 | 154.4887416 | 4.87E−07 | 0.00025548 |
| 110 | 1.575713329 | 0.282665534 | 6.747905312 | 2.98E−06 | 0.001123754 |
| 111 | 16.41692735 | 2.845641353 | 70.70207134 | 5.79E−11 | 1.34E−07 |
| 112 | 1.68490653 | 0.290436533 | 7.262786519 | 1.57E−06 | 0.00068423 |
| 113 | 4.67831493 | 0.793291091 | 20.21841028 | 8.71E−08 | 6.09E−05 |
| 114 | 0.403178392 | 0.068195297 | 1.743110893 | 8.96E−06 | 0.002553906 |
| 115 | 0.4662192 | 0.075483313 | 2.029162747 | 1.12E−05 | 0.003046167 |
| 116 | 1.304251738 | 0.209073323 | 5.684965397 | 1.70E−07 | 0.00010622 |
| 117 | 6.507791975 | 1.03690213 | 28.39135136 | 9.14E−08 | 6.12E−05 |
| 118 | 0.735157305 | 0.116245867 | 3.210803056 | 5.94E−06 | 0.00182919 |
| 119 | 0.629198317 | 0.099406175 | 2.748366884 | 2.14E−07 | 0.000126509 |
| 120 | 0.828351684 | 0.129262116 | 3.624709959 | 2.08E−06 | 0.000855896 |
| 121 | 3.424857018 | 0.52598841 | 15.02033145 | 3.61E−09 | 4.37E−06 |
| 122 | 5.322497713 | 0.813378484 | 23.35897463 | 3.59E−10 | 6.63E−07 |
| 123 | 1.813934213 | 0.275094462 | 7.969293219 | 5.25E−08 | 3.97E−05 |

TABLE 1-5-continued

| | | | | | |
|---|---|---|---|---|---|
| 124 | 0.37043989 | 0.054315236 | 1.634938505 | 6.35E−06 | 0.001940697 |
| 125 | 0.333723081 | 0.04810898 | 1.476179483 | 1.45E−05 | 0.003814186 |
| 126 | 2.011687196 | 0.287666505 | 8.907769961 | 5.09E−09 | 5.00E−06 |
| 127 | 0.654962152 | 0.090235639 | 2.913868203 | 5.66E−06 | 0.001754541 |
| 128 | 0.330655058 | 0.043906528 | 1.477649177 | 7.19E−06 | 0.002140181 |
| 129 | 1.571254161 | 0.207584656 | 7.025932581 | 1.60E−10 | 3.52E−07 |

TABLE 1-6

| SEQ ID NO | Transcription start site (TSS) | | | | Expression ratio [Adenocarcinoma/ squamous cell carcinoma] |
|---|---|---|---|---|---|
| | Chr. No. | Start position | Termination position | Strand | Gene name | |

| SEQ ID NO | Chr. No. | Start position | Termination position | Strand | Gene name | Expression ratio |
|---|---|---|---|---|---|---|
| 130 | chr12 | 79439461 | 79439490 | + | SYT1 | 0.029241688 |
| 131 | chr2 | 233352531 | 233352550 | − | ECEL1 | 0.028581804 |
| 132 | chr2 | 78769157 | 78769171 | − | | 0.028577635 |
| 133 | chr12 | 85306494 | 85306558 | − | SLC6A15 | 0.028516481 |
| 134 | chr12 | 131200810 | 131200859 | − | RIMBP2 | 0.028417282 |
| 135 | chr2 | 173600565 | 173600592 | + | RAPGEF4 | 0.027735565 |
| 136 | chr13 | 100622559 | 100622611 | − | | 0.027174915 |
| 137 | chr1 | 4714656 | 4714675 | + | AJAP1 | 0.027120366 |
| 138 | chr6 | 56507679 | 56507695 | − | DST | 0.026730625 |
| 139 | chr1 | 207070775 | 207070797 | + | IL24 | 0.026053235 |
| 140 | chr3 | 147111198 | 147111225 | + | ZIC1 | 0.024094167 |
| 141 | chr1 | 152140653 | 152140680 | + | FLG-AS1 | 0.023960553 |
| 142 | chr6 | 26225354 | 26225378 | + | HIST1H3E | 0.023490556 |
| 143 | chr17 | 27370022 | 27370051 | + | PIPOX | 0.022577856 |
| 144 | chr2 | 207308220 | 207308267 | + | ADAM23 | 0.022160773 |
| 145 | chrX | 30233668 | 30233698 | + | MAGEB2 | 0.021093495 |
| 146 | chrX | 99665262 | 99665280 | − | PCDH19 | 0.02048068 |
| 147 | chr12 | 52912779 | 52912805 | − | KRT5 | 0.020254728 |
| 148 | chr8 | 57359192 | 57359208 | − | PENK | 0.020125777 |
| 149 | chr12 | 28125659 | 28125672 | − | PTHLH | 0.017975332 |
| 150 | chr7 | 96634850 | 96634874 | + | DLX6 | 0.017763231 |
| 151 | chr17 | 74864476 | 74864592 | + | MGAT5B | 0.017579449 |
| 152 | chrX | 148793714 | 148793733 | + | MAGEA11 | 0.016099771 |
| 153 | chr6 | 43423785 | 43423800 | − | DLK2 | 0.016097893 |
| 154 | chr1 | 152140624 | 152140650 | + | FLG-AS1 | 0.015536642 |
| 155 | chr3 | 147127142 | 147127168 | + | ZIC1 | 0.015526007 |

| SEQ ID NO | Average expression of all groups | Ave. expression level of adenorcinoma group | Ave. expression level of squamous cell carcinoma group | Pvalue | FDR |
|---|---|---|---|---|---|
| 130 | 1.257522681 | 0.164606895 | 5.629185825 | 4.34E−06 | 0.001430811 |
| 131 | 3.6260617 | 0.465031202 | 16.27018369 | 1.06E−06 | 0.000490731 |
| 132 | 0.346962993 | 0.044491107 | 1.556850537 | 2.45E−06 | 0.000976179 |
| 133 | 0.27405613 | 0.035074749 | 1.229981656 | 1.55E−05 | 0.004037656 |
| 134 | 1.421852684 | 0.181405717 | 6.383640553 | 2.02E−07 | 0.000122366 |
| 135 | 1.404078263 | 0.175269703 | 6.319312504 | 2.97E−07 | 0.000168028 |
| 136 | 0.374070016 | 0.045843438 | 1.686976328 | 2.64E−05 | 0.006126006 |
| 137 | 2.052719199 | 0.251111529 | 9.259149877 | 6.03E−10 | 1.07E−06 |
| 138 | 6.00941248 | 0.725594399 | 27.1446848 | 4.11E−09 | 4.58E−06 |
| 139 | 1.053184143 | 0.124246208 | 4.768935882 | 2.04E−07 | 0.000122366 |
| 140 | 1.498541185 | 0.164661025 | 6.834061827 | 1.06E−06 | 0.000490731 |
| 141 | 0.813589918 | 0.08894558 | 3.71216727 | 3.14E−06 | 0.001148945 |
| 142 | 1.006703931 | 0.108084331 | 4.601182328 | 2.44E−09 | 3.31E−06 |
| 143 | 0.210545002 | 0.021799527 | 0.965526902 | 1.30E−05 | 0.003457474 |
| 144 | 0.703021995 | 0.071554722 | 3.228891085 | 6.11E−09 | 5.76E−06 |
| 145 | 4.931500774 | 0.479643508 | 22.73892984 | 5.55E−06 | 0.001732476 |
| 146 | 3.680973799 | 0.348402184 | 17.01126026 | 9.83E−12 | 2.53E−08 |
| 147 | 0.488485176 | 0.045763002 | 2.259373872 | 1.59E−07 | 0.000100765 |
| 148 | 28.10595539 | 2.617550056 | 130.0595767 | 5.09E−07 | 0.000260903 |
| 149 | 0.920040008 | 0.07714341 | 4.291626399 | 1.57E−09 | 2.34E−06 |
| 150 | 0.698975198 | 0.057961926 | 3.263028285 | 1.10E−07 | 6.63E−05 |
| 151 | 1.435684251 | 0.117902075 | 6.706812957 | 1.32E−09 | 2.03E−06 |
| 152 | 0.318313756 | 0.024073577 | 1.495274473 | 5.20E−06 | 0.001666531 |
| 153 | 0.215982372 | 0.016332622 | 1.014581373 | 6.46E−06 | 0.001947713 |
| 154 | 0.95292039 | 0.069694633 | 4.485823418 | 9.02E−08 | 6.12E−05 |
| 155 | 0.366493163 | 0.026787279 | 1.725316699 | 3.24E−06 | 0.001160397 |

TABLE 1-7

| SEQ ID NO. | Transcription start site (TSS) | | | | Expression ratio [Adenocarcinoma/ squamous cell carcinoma] |
|---|---|---|---|---|---|
| | Chr. No. | Start position | Termination position | Strand | Gene name |
| 156 | chr11 | 20049037 | 20049050 | + | NAV2 | 0.01533676 |
| 157 | chr2 | 240196457 | 240196486 | − | | 0.014861061 |
| 158 | chr14 | 51955831 | 51955864 | + | FRMD6 | 0.01362291 |
| 159 | chr13 | 100632825 | 100632879 | − | | 0.013567139 |
| 160 | chrX | 151903207 | 151903234 | + | CSAG1 | 0.013369208 |
| 161 | chr3 | 189507460 | 189507471 | + | TP63 | 0.01309368 |
| 162 | chr10 | 5566916 | 5566932 | + | CALML3 | 0.012709747 |
| 163 | chr7 | 139227335 | 139227349 | + | | 0.012035041 |
| 164 | chr7 | 96634878 | 96634900 | + | DLX6 | 0.011236326 |
| 165 | chr11 | 46366799 | 46366832 | + | DGKZ | 0.011157181 |
| 166 | chr7 | 27208886 | 27208937 | + | HOXA-AS4 | 0.010922825 |
| 167 | chr3 | 139258382 | 139258393 | − | RBP1 | 0.010605667 |
| 168 | chr6 | 43423308 | 43423355 | − | DLK2 | 0.010525117 |
| 169 | chrX | 151081351 | 151081390 | + | MAGEA4 | 0.01044828 |
| 170 | chr14 | 51955771 | 51955826 | + | FRMD6 | 0.010368515 |
| 171 | chr9 | 93405073 | 93405123 | − | DIRAS2 | 0.010289968 |
| 172 | chr17 | 39777431 | 39777463 | − | | 0.009895791 |
| 173 | chr3 | 139258420 | 139258434 | − | RBP1 | 0.009840673 |
| 174 | chr6 | 31080343 | 31080359 | − | C6orf15 | 0.009154419 |
| 175 | chr3 | 120627034 | 120627102 | + | STXBP5L | 0.009098657 |
| 176 | chr5 | 167247265 | 167247320 | + | | 0.00906425 |
| 177 | chr11 | 68451973 | 68451986 | + | GAL | 0.00898837 |
| 178 | chr7 | 96634908 | 96634923 | + | DLX6 | 0.008957312 |
| 179 | chr8 | 73449214 | 73449261 | + | KCNB2 | 0.007785853 |
| 180 | chr17 | 39743139 | 39743155 | − | KRT14 | 0.007775847 |
| 181 | chr7 | 26415877 | 26415903 | − | AC004540.4 | 0.005514714 |

| SEQ ID NO. | Average expression of all groups | Ave. expression level of adenorcinoma group | Ave. expression level of squamous cell carcinoma group | Pvalue | FDR |
|---|---|---|---|---|---|
| 156 | 0.241247086 | 0.017430437 | 1.136513681 | 3.22E−06 | 0.001160397 |
| 157 | 2.703806559 | 0.189634487 | 12.76049485 | 2.90E−09 | 3.72E−06 |
| 158 | 0.717073449 | 0.04631913 | 3.400090726 | 2.07E−08 | 1.77E−05 |
| 159 | 0.428463105 | 0.027568964 | 2.032039668 | 6.67E−07 | 0.000331155 |
| 160 | 2.419727989 | 0.153538478 | 11.48448603 | 3.14E−08 | 2.59E−05 |
| 161 | 0.180413703 | 0.011236342 | 0.857123147 | 1.81E−05 | 0.004602826 |
| 162 | 8.643925313 | 0.522735182 | 41.12868584 | 8.04E−09 | 7.43E−06 |
| 163 | 0.602791243 | 0.034607096 | 2.875527832 | 6.01E−07 | 0.0003016 |
| 164 | 0.926612686 | 0.049819459 | 4.433785595 | 1.36E−08 | 1.21E−05 |
| 165 | 0.330401647 | 0.017644312 | 1.581430988 | 2.98E−08 | 0.000168028 |
| 166 | 0.312120992 | 0.016332622 | 1.495274473 | 1.11E−06 | 0.000507317 |
| 167 | 5.138592231 | 0.261401628 | 24.64735464 | 2.45E−14 | 1.41E−10 |
| 168 | 0.352720862 | 0.017812238 | 1.692355369 | 3.07E−08 | 2.58E−05 |
| 169 | 1.440219037 | 0.07222073 | 6.912212264 | 4.17E−09 | 4.58E−06 |
| 170 | 0.892098301 | 0.044406938 | 4.282863752 | 3.97E−08 | 3.16E−05 |
| 171 | 4.349685565 | 0.214943576 | 20.88865352 | 2.97E−11 | 7.21E−08 |
| 172 | 0.187605723 | 0.008929093 | 0.902312244 | 6.55E−06 | 0.001964163 |
| 173 | 51.23366919 | 2.424925354 | 246.4186446 | 1.07E−21 | 4.96E−17 |
| 174 | 0.606661509 | 0.026787279 | 2.926158428 | 4.67E−09 | 4.90E−06 |
| 175 | 4.383173967 | 0.192402572 | 21.14625955 | 2.03E−10 | 4.18E−07 |
| 176 | 0.373440599 | 0.016332622 | 1.801872504 | 2.23E−07 | 0.000130564 |
| 177 | 0.601528569 | 0.026095579 | 2.903260532 | 3.69E−09 | 4.37E−06 |
| 178 | 0.413026408 | 0.017858186 | 1.993699297 | 2.60E−07 | 0.000150237 |
| 179 | 0.29762391 | 0.011236342 | 1.443174181 | 7.53E−08 | 5.53E−05 |
| 180 | 31.53811824 | 1.18919011 | 152.9338308 | 2.52E−13 | 1.06E−09 |
| 181 | 14.9665712 | 0.403774971 | 73.21775609 | 9.88E−17 | 1.14E−12 |

TABLE 1-8

| SEQ ID NO | Transcription start site (TSS) | | | | Expression ratio [Adenocarcinoma/ squamous cell carcinoma] |
|---|---|---|---|---|---|
| | Chr. No. | Start position | Termination position | Strand | Gene name |
| 182 | chr11 | 68452002 | 68452019 | + | GAL | 0.005042784 |
| 183 | chr7 | 139227292 | 139227325 | + | | 0.004498147 |

TABLE 1-8-continued

| | | | | | | |
|---|---|---|---|---|---|---|
| 184 | chr8 | 24814118 | 24814133 | − | NEFL | 0.004122832 |
| 185 | chr9 | 137764479 | 137764484 | − | | 0.003709904 |
| 186 | chr17 | 76533685 | 76533690 | − | | 0.003525122 |
| 187 | chr3 | 147111231 | 147111281 | + | ZIC1 | 0.003262052 |
| 188 | chr13 | 100623375 | 100623425 | − | ZIC5 | 0.002873217 |
| 189 | chr7 | 27213893 | 27213954 | − | HOXA10 | 0.002791674 |
| 190 | chr13 | 100633445 | 100633468 | + | ZIC2 | 0.00271809 |
| 191 | chr3 | 139258363 | 139258374 | − | RBP1 | 0.002220398 |
| 192 | chr7 | 12971296 | 12971310 | + | | 0.00150773 |
| 193 | chr12 | 52913553 | 52913601 | + | | 0 |
| 194 | chr17 | 39742793 | 39742826 | − | KRT14 | 0 |
| 195 | chr19 | 35981358 | 35981374 | − | KRTDAP | 0 |
| 196 | chr3 | 109128858 | 109128884 | + | RP11-702L6.4 | 0 |
| 197 | chr11 | 66673490 | 66673527 | − | | 0 |
| 198 | chr12 | 52908759 | 52908818 | − | | 0 |
| 199 | chr12 | 89241151 | 89241168 | − | | 0 |
| 200 | chr12 | 52913675 | 52913704 | + | | 0 |
| 201 | chr13 | 99330012 | 99330023 | + | | 0 |
| 202 | chr13 | 100634031 | 100634045 | + | ZIC2 | 0 |
| 203 | chr3 | 95928689 | 95928701 | − | | 0 |
| 204 | chr7 | 107968952 | 107968990 | − | NRCAM | 0 |
| 205 | chr9 | 138591319 | 138591340 | − | SOHLH1 | 0 |
| 206 | chrX | 151307020 | 151307055 | − | MAGEA10 | 0 |
| 207 | chrX | 151080929 | 151080974 | + | MAGEA4 | 0 |

| SEQ ID NO | Average expression of all groups | Ave. expression level of adeno-carcinoma group | Ave. expression level of squamous cell carcinoma group | Pvalue | FDR |
|---|---|---|---|---|---|
| 182 | 16.63229422 | 0.411073552 | 81.51717687 | 1.43E−18 | 2.19E−14 |
| 183 | 2.349618855 | 0.51910644 | 11.5404517 | 2.08E−10 | 4.18E−07 |
| 184 | 2.259428714 | 0.045820579 | 11.11386125 | 4.75E−14 | 2.44E−10 |
| 185 | 1.981595555 | 0.03622015 | 9.763097177 | 3.69E−12 | 1.22E−08 |
| 186 | 0.646490053 | 0.011236342 | 3.18504895 | 3.71E−09 | 4.37E−06 |
| 187 | 2.183934049 | 0.035161734 | 10.77902331 | 6.32E−15 | 5.83E−11 |
| 188 | 0.791132644 | 0.011236342 | 3.910717851 | 2.00E−09 | 2.80E−06 |
| 189 | 1.403488244 | 0.019374063 | 6.939944965 | 1.07E−13 | 4.95E−10 |
| 190 | 0.835771344 | 0.011236342 | 4.133911352 | 6.66E−10 | 1.10E−06 |
| 191 | 29.9298817 | 0.329355987 | 148.3319846 | 9.27E−19 | 2.14E−14 |
| 192 | 3.679730527 | 0.027573906 | 18.28835701 | 2.00E−14 | 1.32E−10 |
| 193 | 0.103277583 | 0 | 0.516387916 | 2.05E−05 | 0.005035605 |
| 194 | 0.271143374 | 0 | 1.35571687 | 5.56E−09 | 5.34E−06 |
| 195 | 0.100920877 | 0 | 0.504604386 | 3.23E−05 | 0.007238234 |
| 196 | 0.425887097 | 0 | 2.129435486 | 4.50E−09 | 4.48E−06 |
| 197 | 0.117479158 | 0 | 0.587395792 | 2.03E−05 | 0.005012873 |
| 198 | 0.194428852 | 0 | 0.97214426 | 5.27E−07 | 0.000267397 |
| 199 | 0.188962365 | 0 | 0.944811826 | 1.04E−06 | 0.000490489 |
| 200 | 0.152529642 | 0 | 0.762648211 | 3.96E−06 | 0.001338574 |
| 201 | 0.700484269 | 0 | 3.502421347 | 2.61E−10 | 5.02E−07 |
| 202 | 1.173215355 | 0 | 5.866076777 | 6.38E−12 | 1.84E−08 |
| 203 | 0.667122457 | 0 | 3.335612286 | 8.78E−10 | 1.40E−06 |
| 204 | 1.541282918 | 0 | 7.706414589 | 5.31E−13 | 2.04E−09 |
| 205 | 0.355727362 | 0 | 1.778636811 | 1.93E−09 | 2.79E−06 |
| 206 | 0.268382598 | 0 | 1.341912988 | 3.03E−07 | 0.000168266 |
| 207 | 0.176365707 | 0 | 0.881828535 | 3.22E−06 | 0.001160397 |

TABLE 1-9

| SEQ ID NO | Transcription start site (TSS) | | | | Expression ratio [Adenocarcinoma/ squamous cell carcinoma] | Average expression of all groups |
|---|---|---|---|---|---|---|
| | Chr. No. | Start position | Termination position | Strand | Gene name | | |

| SEQ ID NO | Chr. No. | Start position | Termination position | Strand | Gene name | Expression ratio [Adenocarcinoma/ squamous cell carcinoma] | Average expression of all groups |
|---|---|---|---|---|---|---|---|
| 208 | chrX | 151081334 | 151081343 | + | MAGEA4 | 0 | 0.351361669 |
| 209 | chr1 | 195691504 | 195691510 | − | | 0 | 0.176353213 |
| 210 | chr12 | 28299014 | 28299023 | + | CCDC91 | 0 | 2.393365038 |
| 212 | chr13 | 99330043 | 99330058 | + | | 0 | 1.297455784 |
| 212 | chr5 | 167181917 | 167181979 | + | TENM2 | 0 | 0.585744601 |
| 213 | chr7 | 137570475 | 13570486 | − | | 0 | 0.321214781 |

TABLE 1-9-continued

| SEQ ID NO | Ave. expression level of adenocarcinoma group | Ave. expression level of squamous cell carcinoma group | Pvalue | FDR |
|---|---|---|---|---|
| 209 | 0 | 0.881766067 | 3.05E−06 | 0.001127751 |
| 210 | 0 | 11.96682519 | 1.78E−14 | 1.32E−10 |
| 212 | 0 | 6.487278918 | 3.16E−12 | 1.12E−08 |
| 212 | 0 | 2.928723007 | 2.58E−09 | 3.41E−06 |
| 213 | 0 | 1.606073907 | 1.15E−07 | 7.45E−05 |

(B) Selection of Transcription Start Site for Highly Accurate Prediction

The transcription start sites identified in the preceding step (A) were examined for whether to be able to classify adenocarcinoma (adenocarcinoma free of a BAC component) or squamous cell carcinoma (poorly differentiated lung squamous cell carcinoma) using only one expression level. It was confirmed that both of the samples for transcription start site extraction and the samples for validation can be classified with 100% specificity and 100% sensitivity by setting some threshold for each transcription start site. Examples of the threshold are shown in Table 2 (when the largest value for a certain group is smaller than the smallest value for the other groups, an average thereof is shown in Table 2).

TABLE 2

| SEQ ID NO | Threshold (threshold_cpm) |
|---|---|
| No. 2 | 0.50 |
| No. 3 | 2.00 |
| No. 5 | 5.00 |
| No. 7 | 9.00 |

Example 2 Differentiation Between Adenocarcinoma and Squamous Cell Carcinoma with Protein Expression as Index (1) Specimen The lung adenocarcinoma specimens used were 45 surgical specimens involving 7 bronchioloalveolar carcinoma (BAC) specimens, 22 adenocarcinoma specimens with BAC, and 16 adenocarcinoma specimens without BAC. On the other hand, the lung squamous cell carcinoma specimens used were 29 surgical specimens involving 18 well and moderately differentiated squamous cell carcinoma (SCC) specimens and 11 poorly differentiated SCC specimens.

(2) Detection of Protein by Immunostaining

A total of 79 specimens of lung adenocarcinoma and lung squamous cell carcinoma were evaluated for the expression of each protein by immunostaining using antibodies against adenocarcinoma markers ST6GALNAC1, napsin, and TTF-1 and squamous cell carcinoma markers CK5, CK6, desmoglein 3 (DSG3), p40, and SPATS2.

i) Antibody
1) Anti-TTF-1 antibody (DAKO)
2) Anti-napsin A antibody (Leica Biosystems Nussloch GmbH, "NCL-L-napsin A")
3) Anti-p40 antibody (EMD Millipore, "PC373")
4) Anti-CK5 antibody (Leica Biosystems Nussloch GmbH, "NCL-CK5")
5) Anti-CK6 antibody (GeneTex Inc., "GTX73556")
6) Anti-desmoglein 3 antibody (BIOCARE Medical Inc., "ACR419A, C")
7) Anti-ST6GALNAC1 antibody (SIGMA Life Science, "HPA014975"
8) Anti-SPATS2 antibody (SIGMA Life Science, "HPA038643"

ii) Immunostaining Method

The biological sample isolated from each patient was fixed in formalin by a routine method, then embedded in paraffin, and sliced into a tissue section, which was attached to slide glass. The resultant was used as a section sample. Subsequently, the section sample was heat-treated under conditions given below for antigen retrieval. Subsequently, an antibody against each marker protein (primary antibody) was added under conditions given below and reacted therewith. After thorough washing with a buffer solution, Envision was used as a secondary antibody and reacted therewith under conditions given below. After thorough washing with a buffer solution, color was developed using DAB. The positivity or negativity of the preparation was observed under an optical microscope.

TABLE 3

| Detection marker | Heat treatment buffer solution | Temperature/ time | Primary antibody dilution ratio | Primary antibody reaction conditions | Secondary antibody reaction time |
|---|---|---|---|---|---|
| TTF-1 | pH9 TE buffer solution | 110° C./15 min | X75 | 4° C. O/N | Envision 50 min |
| NapsinA | Not treated |  | X300 | 4° C. O/N | Envision 45 min |
| p40 | pH6 citrate buffer solution | 120° C./10 min | X2500 | 4° C. O/N | Envision 45 min |
| CK5 | pH6 citrate buffer solution | 120° C./10 min | X200 | 4° C. O/N | Envision 45 min |
| CK6 | pH9 TE buffer solution | 100° C./30 min | X100 | RT 2 hr | Envision 45 min |
| Desmoglein 3 | pH9 TE buffer solution | 105° C./30 min | X50 | After RT 1H, 4° C. O/N | Envision 75 min |
| ST6GALNAC-1 | pH6 citrate buffer solution | 120° C./10 min | X4000 | RT 90 min | Envision 45 min |
| SPATS-2 | pH9 TE buffer solution | 105° C./30 min | X50 | RT 120 min | Envision 50 min | iii) Determination

Each sample was found positive when the nuclei or cytoplasms of cancer cells were stained with moderate or stronger staining intensity. Score 0 was given when no cancer cell exhibited positivity in the typical section of each case; Score 1 was given when less than 50% of the cancer cells exhibited positive images; and Score 2 was given when 50% or more of the cancer cells exhibited positive images. Scores 0 and 1 were determined as negativity, and Score 2 was determined as positivity. This assessment was conducted by two pathologists.

(3) Assessment of Usefulness as Adenocarcinoma and Squamous Cell Carcinoma Markers (a) Each marker was assessed for its usefulness as an adenocarcinoma or squamous cell carcinoma marker. Specifically, sensitivity and specificity for an adenocarcinoma marker were determined for the differential diagnosis of adenocarcinoma. Likewise, sensitivity and specificity for a squamous cell carcinoma marker were assessed in terms of the ability to differentially diagnose squamous cell carcinoma. p values were calculated by the Fisher's exact test.

TABLE 4

| Adenocarcinoma marker | | Squamous cell carcinoma marker | |
|---|---|---|---|
| ST6GALNAC1(+) | ST6GALNAC1(−) | CK5(+) | CK5(−) |
| Ad 43 | 2 | Ad 0 | 45 |
| Sq 1 | 28 | Sq 25 | 4 |
| $p = 6.13 \times 10^{-17}$/Sensitivity = 0.956/ Specificity = 0.966 | | $p = 6.77 \times 10^{-16}$/Sensitivity = 0.862/Specificity = 1.000 | |
| Napsin A(+) | Napsin A(−) | DSG3(+) | DSG3(−) |
| Ad 35 | 10 | Ad 0 | 45 |
| Sq 0 | 29 | Sq 24 | 5 |
| $p = 2.88 \times 10^{-12}$/Sensitivity = 0.778/ Specificity = 1.000 | | $p = 6.77 \times 10^{-15}$/Sensitivity = 0.828/Specificity = 1.000 | |
| TTF-1(+) | TTF-1(−) | p40(+) | p40(−) |
| Ad 33 | 12 | Ad 1 | 44 |
| Sq 0 | 29 | Sq 25 | 4 |
| $p = 2.82 \times 10^{-11}$/Sensitivity = 0.733/ Specificity = 1.000 | | $p = 1.62 \times 10^{-14}$/Sensitivity = 0.862/Specificity = 0.978 | |
| | | SPATS2(+) | SPATS2(−) |
| | | Ad 3 | 42 |
| | | Sq 20 | 9 |
| | | $p = 1.78 \times 10^{-8}$/Sensitivity = 0.690/Specificity = 0.933 | |
| | | CK6(+) | CK6(−) |
| | | Ad 20 | 25 |
| | | Sq 23 | 6 |
| | | $p = 3.80 \times 10^{-3}$/Sensitivity = 0.793/Specificity = 0.556 | |

Ad: adenocarcinoma, Sq: squamous cell carcinoma

As a result, it was found as to the adenocarcinoma markers that ST6GALNAC1 has both high sensitivity and high specificity while napsin A and TTF-1 have low sensitivity but may exhibit positivity in ST6GALNAC1(−) specimens. On the other hand, as for the squamous cell carcinoma markers, CK5, DSG3, and p40 had both high sensitivity and high specificity, but tended to exhibit negativity in common in some squamous cell carcinoma cases due to their similar behaviors. It was also found that SPATS2 does not have much high sensitivity and may exhibit positivity in CK5/DSG3/p40-negative squamous cell carcinoma. CK6 may also exhibit positivity in CK5/DSG3/p40-negative squamous cell carcinoma, but is more likely to exhibit positivity in adenocarcinoma, and a tendency of low specificity was observed. These results suggested that more highly accurate differentiation may be achieved by using complementary pieces of information brought about by a plurality of markers in combination, rather than each marker alone.

(4) Assessment of Two Markers in Combination 24 combinations of any two selected from the 3 adenocarcinoma markers and the 5 squamous cell carcinoma markers were studied for the ability to differentiate between adenocarcinoma and squamous cell carcinoma. The results are shown in Table 5.

TABLE 5

| | Ad | | | | Sq | | | | |
|---|---|---|---|---|---|---|---|---|---|
| Combination | (+)/(+) | (+)/(−) | (−)/(+) | (−)/(−) | (+)/(+) | (+)/(−) | (−)/(+) | (−)/(−) | p-value |
| TTF-1/ST6GALNAC1 | 31 | 2 | 12 | 0 | 0 | 0 | 1 | 28 | 4.80E−20 |
| CK5/ST6GALNAC1 | 0 | 0 | 43 | 2 | 1 | 24 | 0 | 4 | 6.71E−20 |
| DSG3/ST6GALNAC1 | 0 | 0 | 43 | 2 | 1 | 23 | 0 | 5 | 8.95E−20 |
| CK5/SPATS2 | 0 | 0 | 3 | 42 | 16 | 9 | 4 | 0 | 1.12E−19 |
| DSG3/SPATS2 | 0 | 0 | 3 | 42 | 15 | 9 | 5 | 0 | 1.79E−19 |
| p40/ST6GALNAC1 | 1 | 0 | 42 | 2 | 1 | 24 | 0 | 4 | 2.56E−19 |
| ST6GALNAC1/SPATS2 | 3 | 40 | 0 | 2 | 1 | 0 | 19 | 9 | 7.99E−19 |
| Napsin A/ST6GALNAC1 | 34 | 1 | 9 | 1 | 0 | 0 | 1 | 28 | 1.02E−18 |
| p40/SPATS2 | 0 | 1 | 3 | 41 | 16 | 9 | 4 | 0 | 1.90E−18 |
| Napsin/CK5 | 0 | 35 | 0 | 10 | 0 | 0 | 25 | 4 | 3.20E−18 |

TABLE 5-continued

| Combination | Ad (+)/(+) | (+)/(−) | (−)/(+) | (−)/(−) | Sq (+)/(+) | (+)/(−) | (−)/(+) | (−)/(−) | p-value |
|---|---|---|---|---|---|---|---|---|---|
| Napsin/p40 | 1 | 34 | 0 | 10 | 0 | 0 | 25 | 4 | 4.36E−18 |
| TTF-1/CK5 | 0 | 33 | 0 | 12 | 0 | 0 | 25 | 4 | 5.82E−18 |
| TTF-1/p40 | 1 | 32 | 0 | 12 | 0 | 0 | 25 | 4 | 7.61E−18 |
| Napsin A/DSG3 | 0 | 35 | 0 | 10 | 0 | 0 | 24 | 5 | 9.60E−18 |
| TTF-1/DSG3 | 0 | 33 | 0 | 12 | 0 | 0 | 24 | 5 | 1.98E−17 |
| TTF-1/Napsin A | 27 | 6 | 8 | 4 | 0 | 0 | 0 | 29 | 4.96E−16 |
| CK5/DSG3 | 0 | 0 | 0 | 45 | 24 | 1 | 0 | 4 | 6.77E−16 |
| CK5/p40 | 0 | 0 | 1 | 44 | 25 | 0 | 0 | 4 | 6.77E−16 |
| CK5/CK6 | 0 | 0 | 20 | 25 | 22 | 3 | 1 | 3 | 1.17E−15 |
| DSG3/p40 | 0 | 0 | 1 | 44 | 24 | 0 | 1 | 4 | 1.30E−15 |
| CK6/p40 | 0 | 20 | 1 | 24 | 22 | 1 | 3 | 3 | 6.49E−15 |
| CK6/DSG3 | 0 | 20 | 0 | 25 | 21 | 2 | 3 | 3 | 2.33E−14 |
| Napsin A/CK6 | 13 | 22 | 7 | 3 | 0 | 0 | 23 | 6 | 1.60E−11 |
| TTF-1/CK6 | 14 | 19 | 6 | 6 | 0 | 0 | 23 | 6 | 6.46E−11 |

In the table, TTF-1/p40 is a marker combination which is often used in pathological diagnostic settings. When the p values obtained by the Fisher's exact test were compared, the combination of TTF-1 and p40 comes in the 13th place. On the other hand, the combinations with either ST6GALNAC1 or SPATS2 occupied the 1st to 9th places, indicating that these two proteins are essential for highly accurate differentiation which is not achievable by the conventional marker combinations. Particularly, TTF-1 and ST6GALNAC1 achieved correct differentiation in all of the 45 adenocarcinoma cases and 28 out of the 29 squamous cell carcinoma cases.

(5) Assessment of Three Markers in Combination

There exist a total of 56 combinations as combinations of any three selected from the 3 adenocarcinoma markers and the 5 squamous cell carcinoma markers. Among them, the following 6 combinations were able to completely differentiate between adenocarcinoma and squamous cell carcinoma.

1) ST6GALNAC1/TTF-1/CK5
2) ST6GALNAC1/TTF-1/DSG3
3) ST6GALNAC1/TTF-1/p40
4) ST6GALNAC1/SPATS2/DSG3
5) ST6GALNAC1/SPATS2/CK5
6) ST6GALNAC1/SPATS2/p40

These results suggest that ST6GALNAC1 is useful for complete differentiation.

INDUSTRIAL APPLICABILITY

According to the present invention, the differential diagnosis of adenocarcinoma, which is difficult to discriminate pathologically and histologically, particularly, the differentiation between squamous cell carcinoma and adenocarcinoma, further the differentiation between poorly differentiated squamous cell carcinoma and adenocarcinoma, and further the differentiation between poorly differentiated squamous cell carcinoma and adenocarcinoma free of a BAC component can be performed objectively and rapidly for the histopathological type of lung cancer in a patient without depending on the subjectivity of specialists such as well-trained pathologists or clinical laboratory technicians. In other words, the present invention can be suitably used in point of care testing (POCT) from the collection of specimens from patients to the analysis thereof.

The invention claimed is:

1. A method for detecting a squamous cell carcinoma or adenocarcinoma in a lung cancer patient lesion, comprising:
   measuring an expression level of ST6GALNAC1 and SPATS2 proteins in cells collected from the lesion by contacting the cells with an anti-ST6GALNAC1 antibody and an anti-SPATS2 antibody, and
   detecting increased ST6GALNAC1 protein in the cells collected from the lesion relative to a non-cancerous control cell thereby detecting adenocarcinoma; or
detecting increased SPATS2 protein in the cells collected from the lesion relative to a non-cancerous control cell thereby detecting squamous cell carcinoma.

2. The method of claim 1, further comprising:
   measuring an expression level of at least one additional protein selected from the group consisting of P40, CK5, CK6, DSG3, TTF-1, and napsin A.

3. The method of claim 2, wherein the method comprises measuring expression levels of three proteins selected from the group consisting of:
   1) ST6GALNAC1/SPATS2/DSG3,
   2) ST6GALNAC1/SPATS2/CK5, and
   3) ST6GALNAC I/SPATS2/p40.

4. The method of claim 1, wherein the measuring of the expression level of each protein is performed by an immunohistochemical analysis method.

5. The method of claim 2, wherein the method further comprises measuring expression levels of CK5.

6. The method of claim 2, wherein the method comprises measuring expression levels of CK5, ST6GALNAC1, and SPATS2.

7. A method for treating lung cancer in a subject, the method comprising:
   contacting cells from a lesion collected from the subject with an anti-ST6GALNAC1 antibody and an anti-SPATS2 antibody and detecting specific antibody binding;
   detecting increased ST6GALNAC1 protein in the cells relative to non-cancerous control cells thereby detecting adenocarcinoma; and/or detecting increased SPATS2 protein in the cells relative to non-cancerous control cells thereby detecting squamous cell carcinoma; and
   treating the subject with a cancer therapy for adenocarcinoma and/or treating the subject with a cancer therapy for squamous cell carcinoma based on the detecting of adenocarcinoma and/or squamous cell carcinoma.

8. The method of claim 1, wherein the detecting comprises detecting the increased ST6GALNAC1 protein or SPATS2 protein in at least 50% of the cells collected from the lesion.

9. The method of claim 7, wherein the detecting comprises detecting the increased ST6GALNAC1 protein or SPATS2 protein in at least 50% of the cells collected from the lesion.

* * * * *

SEQUENCE LISTING

<160> NUMBER OF SEQ ID NOS: 213

<210> SEQ ID NO 1
<211> LENGTH: 142
<212> TYPE: DNA
<213> ORGANISM: Homo sapiens
<220> FEATURE:
<221> NAME/KEY: Transcript Start Site
<222> LOCATION: (1)..(42)

<400> SEQUENCE: 1
ctgcagctga gccaggctgc tgcagagtta atgtacagta ccacggagcc tgcaagtgtc     60
ctgagctgat cagagctggg gcggcacagc ccagggcaga caaggcggct gcgaggattc    120
caaaggttct gctggaaatt cg                                             142

<210> SEQ ID NO 2
<211> LENGTH: 164
<212> TYPE: DNA
<213> ORGANISM: Homo sapiens
<220> FEATURE:
<221> NAME/KEY: Transcript Start Site

<222> LOCATION: (1)..(64)

<400> SEQUENCE: 2
ttacatacac agacacgcaa tcgcagatac gcccttccgg ccacagaaac acaccattac 60
acacacatac acagaaagac acacacagac acacaatcac acgcagcccc tccccgccac 120
agagacacac cattacatac acagacacac acagaaagac acac 164

<210> SEQ ID NO 3
<211> LENGTH: 181
<212> TYPE: DNA
<213> ORGANISM: Homo sapiens
<220> FEATURE:
<221> NAME/KEY: Transcript Start Site
<222> LOCATION: (1)..(81)

<400> SEQUENCE: 3
ggccaggaaa cctgagcggt gagactccca gctgcctaca tcaaggcccc aggacatgca 60
gaaccttcct ctagaacccg acccaccacc atgaggtcct gcctgtggag atgcaggcac 120
ctgagccaag gcgtccagtg gtccttgctt ctggctgtcc tggtcttctt tctcttcgcc 180
t 181

<210> SEQ ID NO 4
<211> LENGTH: 123
<212> TYPE: DNA
<213> ORGANISM: Homo sapiens
<220> FEATURE:
<221> NAME/KEY: Transcript Start Site
<222> LOCATION: (1)..(23)

<400> SEQUENCE: 4
cttctgtcca ccctacagag cccacggcca tggcagccca ggcagctggt gtatctaggc 60
agcgggcagc cactcaaggt cttggctcca accaaaacgc tttgaagtac ttgggccagg 120
att 123

<210> SEQ ID NO 5
<211> LENGTH: 129
<212> TYPE: DNA
<213> ORGANISM: Homo sapiens
<220> FEATURE:
<221> NAME/KEY: Transcript Start Site
<222> LOCATION: (1)..(29)

<400> SEQUENCE: 5
gcagggtaaa gcatgagaac atcagagtct ggggcggcgg cggtggctgc aacggtggct 60
gtgacggtgg ctgccgctgg gtttggcttt ctggattttt gttcagagtc gctaatgtat 120
cccccacaa 129

<210> SEQ ID NO 6
<211> LENGTH: 117
<212> TYPE: DNA
<213> ORGANISM: Homo sapiens
<220> FEATURE:
<221> NAME/KEY: Transcript Start Site
<222> LOCATION: (1)..(17)

<400> SEQUENCE: 6
ccacaaagcc gggctgtccc aggctgaggc ggttgctccc ctgccgggtg tgttagaagc 60
aagttagagg aagaaggtct tggggactac gggcgccacc gagaacccat acgaggc 117

```
<210> SEQ ID NO 7
<211> LENGTH: 119
<212> TYPE: DNA
<213> ORGANISM: Homo sapiens
<220> FEATURE:
<221> NAME/KEY: Transcript Start Site
<222> LOCATION: (1)..(19)

<400> SEQUENCE: 7
cggcagcatc ctgcagtccg gcccaggaga gaagtgggga ggcggcggtg ggggcggggc    60
ggcgtccggc tctgagagag ctggggggagg agcgcggcgg cgacggcggc ggtggctct   119

<210> SEQ ID NO 8
<211> LENGTH: 118
<212> TYPE: DNA
<213> ORGANISM: Homo sapiens
<220> FEATURE:
<221> NAME/KEY: Transcript Start Site
<222> LOCATION: (1)..(18)

<400> SEQUENCE: 8
cgggctcagt tcgtaaagga gccgggtgac ttcagaggcg ccggcccgtc cgtctgccgc    60
acctgagcac ggcccctgcc cgagcctggc ccgccgcgat gctgtaggga ccgccgtg    118

<210> SEQ ID NO 9
<211> LENGTH: 174
<212> TYPE: DNA
<213> ORGANISM: Homo sapiens
<220> FEATURE:
<221> NAME/KEY: Transcript Start Site
<222> LOCATION: (1)..(74)

<400> SEQUENCE: 9
tcccgccccg cccaggcgcc cgcggagatc caggttcgag gctggcgcgg cgcggagagt    60
gggctggagg ccggggcggg acgcgttgtg cagcgggtaa gcgcacggcc gagcgagcat   120 ggaggggggac cgggtggccg ggcggccggt gctgtcgtcg ttaccagtgc tact         174

<210> SEQ ID NO 10
<211> LENGTH: 116
<212> TYPE: DNA
<213> ORGANISM: Homo sapiens
<220> FEATURE:
<221> NAME/KEY: Transcript Start Site
<222> LOCATION: (1)..(16)

<400> SEQUENCE: 10
ccggacggca aggatgtgag gcaggcgagc cggacgccgc tcgcagcacc ggagagggcg    60
cactgcaaag gcgggcagca gaccgtggag agcccgggag cggagctgga caccgc      116

<210> SEQ ID NO 11
<211> LENGTH: 119
<212> TYPE: DNA
<213> ORGANISM: Homo sapiens
<220> FEATURE:
<221> NAME/KEY: Transcript Start Site
<222> LOCATION: (1)..(19)

<400> SEQUENCE: 11
gcggccggct cagtgctgcc gggcaccggg gcggcgggtt ggtctacgct gtgcgcggcg    60
gacgtcggag gcagcgggga gcggagcggg gccgccgggg cctctccagg gccgcagcg   119

<210> SEQ ID NO 12
<211> LENGTH: 167
```

```
<212> TYPE: DNA
<213> ORGANISM: Homo sapiens
<220> FEATURE:
<221> NAME/KEY: Transcript Start Site
<222> LOCATION: (1)..(67)

<400> SEQUENCE: 12
gaggaggagg aggaagggc gatcgcggcg gcggcggcgg cggcgaggag ctgtgccttc    60
cacctctcca gccccggcag gacggggcg gccgccgcga acccggggcg gggacagcac  120
gcagcctcga ggcgcgcacc cccgcccggc agcggccccg acacccg                167

<210> SEQ ID NO 13
<211> LENGTH: 137
<212> TYPE: DNA
<213> ORGANISM: Homo sapiens
<220> FEATURE:
<221> NAME/KEY: Transcript Start Site
<222> LOCATION: (1)..(37)

<400> SEQUENCE: 13
cgttcgttac tctgctgtgc tgcctcagac gcggagggct gcgtgcagtg ggagcgggct    60
ccaggagccc gagcctccag ccgtccccag agcaaggcag caccgaggcc tggccacagc  120
aatatccatc tggaagc                                                  137

<210> SEQ ID NO 14
<211> LENGTH: 120
<212> TYPE: DNA
<213> ORGANISM: Homo sapiens
<220> FEATURE:
<221> NAME/KEY: Transcript Start Site
<222> LOCATION: (1)..(20)

<400> SEQUENCE: 14
gaggaggaga agcagtgggg aggcgcagcc gctcacctgc ggggcagggc gcggaggagg    60
gacccgggct gcgcgctctc gggccgagga accaggacgc gcccggagcc tcgcacgcgg  120

<210> SEQ ID NO 15
<211> LENGTH: 111
<212> TYPE: DNA
<213> ORGANISM: Homo sapiens
<220> FEATURE:
<221> NAME/KEY: Transcript Start Site
<222> LOCATION: (1)..(11)

<400> SEQUENCE: 15
ctgtgggcac aagaggcagc actcaggaca atctccagca tggcctggtc tcctctcctc    60
ctcactctcc tcgctcactg cacaggtgac tggatacagg tccaggggag g            111

<210> SEQ ID NO 16
<211> LENGTH: 192
<212> TYPE: DNA
<213> ORGANISM: Homo sapiens
<220> FEATURE:
<221> NAME/KEY: Transcript Start Site
<222> LOCATION: (1)..(92)

<400> SEQUENCE: 16
gctgagcaaa gatgacatcc gaagaatgcg actcttggcg gacagcgcag tggcagggct    60
ccggcctgtg tcctctagga gcggagcccg tttgctggtg ctggaggggg gcgcacctgg  120
cgctgtgctc cgctgtggcc ctagcccctg tgggcttctc aagcagccct tggacatgag  180
tgaggtgttt gc                                                       192
```

```
<210> SEQ ID NO 17
<211> LENGTH: 144
<212> TYPE: DNA
<213> ORGANISM: Homo sapiens
<220> FEATURE:
<221> NAME/KEY: Transcript Start Site
<222> LOCATION: (1)..(44)

<400> SEQUENCE: 17
ctggcttttg ttcccggcgt ctgacttctg acgggcagga gtggccgtgg aggctgcggc    60
gcgcggctgg gacctgggcc ggcggccacg gagagcccct tggcccctcc cgtgttggcca  120 tttcctggga cttgtgtccg cagg                                          144

<210> SEQ ID NO 18
<211> LENGTH: 114
<212> TYPE: DNA
<213> ORGANISM: Homo sapiens
<220> FEATURE:
<221> NAME/KEY: Transcript Start Site
<222> LOCATION: (1)..(14)

<400> SEQUENCE: 18
cgcgctcaga gggagccggg ccgccgtcgc tgccgccgct gtccccgcgc cctgcgcccg    60
gtggcccccc acctccgccc cgcggccgta cctggcgccc cctggctccc ccgg         114

<210> SEQ ID NO 19
<211> LENGTH: 117
<212> TYPE: DNA
<213> ORGANISM: Homo sapiens
<220> FEATURE:
<221> NAME/KEY: Transcript Start Site
<222> LOCATION: (1)..(17)

<400> SEQUENCE: 19
gatgtttcag tcacatttca gccactgctc tgagaatttg tgagcagccc ctaacaggct    60
gttacttcac tacaactgac gatatgatca tcttaattta cttatttctc ttgctat      117

<210> SEQ ID NO 20
<211> LENGTH: 117
<212> TYPE: DNA
<213> ORGANISM: Homo sapiens
<220> FEATURE:
<221> NAME/KEY: Transcript Start Site
<222> LOCATION: (1)..(17)

<400> SEQUENCE: 20
gcctgacccc ctcccatcct ttggcctctg acccttttc cacagggac ctaccctat      60 tgcggtcctc cagctcatct ttcacctcac cccctcctc ctccttggct ttaatta       117

<210> SEQ ID NO 21
<211> LENGTH: 177
<212> TYPE: DNA
<213> ORGANISM: Homo sapiens
<220> FEATURE:
<221> NAME/KEY: Transcript Start Site
<222> LOCATION: (1)..(77)

<400> SEQUENCE: 21 gccctcgcc cccgcccct cgcccccgc cgccgccacc gcggtcagcc agcggaccag       60
cggcaggagc cgttccccga cgggcagcag ggcgctcggc ctccgcgtgt gggctgagcg   120
cggcgacgct gctgccccga aatccccgtg gattttgagt cggtaagtgg ctaggga      177
```

<210> SEQ ID NO 22
<211> LENGTH: 166
<212> TYPE: DNA
<213> ORGANISM: Homo sapiens
<220> FEATURE:
<221> NAME/KEY: Transcript Start Site
<222> LOCATION: (1)..(66)

<400> SEQUENCE: 22
ggagccgagc cggggaatcc tgctctggga tagcacccgg ccccgcagag cagcgcggca      60
gcccaagggc cccggcgccg ggggcggcgg ggaaccccaa acgcaaccgg gtctggaggg     120
atccccgcgc cgagccagcc gccgtcaccg cctccgcgcc gcccct                    166

<210> SEQ ID NO 23
<211> LENGTH: 135
<212> TYPE: DNA
<213> ORGANISM: Homo sapiens
<220> FEATURE:
<221> NAME/KEY: Transcript Start Site
<222> LOCATION: (1)..(35)

<400> SEQUENCE: 23
gggcgcgcgg gcccggccaa ggcaagcgcc ggtggggcgg cggcgccaga gctgctggag      60
cgctcggggt ccccgggcgg cggcggcggc gcagaggagg aggcaggcgg cggccccggt     120
ggctcccccc cggac                                                      135

<210> SEQ ID NO 24
<211> LENGTH: 121
<212> TYPE: DNA
<213> ORGANISM: Homo sapiens
<220> FEATURE:
<221> NAME/KEY: Transcript Start Site
<222> LOCATION: (1)..(21)

<400> SEQUENCE: 24
gcgcgctgcc cagcagcgct gctgtccccg ccgtgcgccc ttcgccgctg agctcgcagc      60
ctccggcgcc cacctccacc tccagtgtcc cgcctcgggc cgtcgccctc cagcggctcg     120
c                                                                     121

<210> SEQ ID NO 25
<211> LENGTH: 114
<212> TYPE: DNA
<213> ORGANISM: Homo sapiens
<220> FEATURE:
<221> NAME/KEY: Transcript Start Site
<222> LOCATION: (1)..(14)

<400> SEQUENCE: 25
gtgctcaaga ctttctccga ggtatgaaca agaaccaggc gtctgggccc tttccgctcg      60
ccccatcgct cagccgccgc gccccggacg cccgctgtgc ccctgccgg cggg            114

<210> SEQ ID NO 26
<211> LENGTH: 127
<212> TYPE: DNA
<213> ORGANISM: Homo sapiens
<220> FEATURE:
<221> NAME/KEY: Transcript Start Site
<222> LOCATION: (1)..(27)

<400> SEQUENCE: 26
ccggcccgcg cccaggagca gagccgcgct cgctccactc agctcccagc tcccaggact      60
ccgctggctc ctcgcaagtc ctgccgccca gcccgccggg atgcagtccg ggccgcggcc    120
cccactt                                                              127

<210> SEQ ID NO 27
<211> LENGTH: 117
<212> TYPE: DNA
<213> ORGANISM: Homo sapiens
<220> FEATURE:
<221> NAME/KEY: Transcript Start Site
<222> LOCATION: (1)..(17)

<400> SEQUENCE: 27
cggcggcgcc agagctgctg gagcgctcgg ggtccccggg cggcggcggc ggcgcagagg    60
aggaggcagg cggcggcccc ggtggctccc ccccggacgg tgcgcggccc ggcccgt      117

<210> SEQ ID NO 28
<211> LENGTH: 113
<212> TYPE: DNA
<213> ORGANISM: Homo sapiens
<220> FEATURE:
<221> NAME/KEY: Transcript Start Site
<222> LOCATION: (1)..(13)

<400> SEQUENCE: 28
cggcttcact cgcgcacgcc gacctcccgg ctgcagtcct acctcttgga actaccgtg    60 tttccgggcc cagccctcgc agcccccac ctcctcgccc cggcccgggg atc           113

<210> SEQ ID NO 29
<211> LENGTH: 125
<212> TYPE: DNA
<213> ORGANISM: Homo sapiens
<220> FEATURE:
<221> NAME/KEY: Transcript Start Site
<222> LOCATION: (1)..(25)

<400> SEQUENCE: 29
gggtgacttc agaggcgccg gcccgtccgt ctgccgcacc tgagcacggc ccctgcccga    60
gcctggcccg ccgcgatgct gtagggaccg ccgtgtcctc ccgccggacc gttatccgcg    120
ccggg                                                                125

<210> SEQ ID NO 30
<211> LENGTH: 154
<212> TYPE: DNA
<213> ORGANISM: Homo sapiens
<220> FEATURE:
<221> NAME/KEY: Transcript Start Site
<222> LOCATION: (1)..(54)

<400> SEQUENCE: 30
gagcggctgc agcggcagcg gccgcggctg agaagcgcgg gccggagtgc agtgcgagac    60
cggctggagg aggcggctcc gcgaagccgg tgtgggcgca ggtaggaacc ccctatgctg    120
cctcccccag gtcgggtctg gctggactgc ccgg                                154

<210> SEQ ID NO 31
<211> LENGTH: 129
<212> TYPE: DNA
<213> ORGANISM: Homo sapiens
<220> FEATURE:
<221> NAME/KEY: Transcript Start Site
<222> LOCATION: (1)..(29)

<400> SEQUENCE: 31

```
cggcaatcca ggccgccttt tgcagccgcc cgcggccgcg ccgggctctg cgcgccgcgc    60
tcctgcctcc tcccccgtca gcggcggccc cagccccgcg ccccccgggc ccgcgccgcc   120
gcggccccg                                                           129
```

<210> SEQ ID NO 32
<211> LENGTH: 118
<212> TYPE: DNA
<213> ORGANISM: Homo sapiens
<220> FEATURE:
<221> NAME/KEY: Transcript Start Site
<222> LOCATION: (1)..(18)

<400> SEQUENCE: 32

```
gtcacagagc aggacagcaa ggacagcacc tacagcctca gcagcaccct gacgctgagc    60
aaagcagact acgagaaaca caaagtctac gcctgcgaag tcacccatca gggcctga    118
```

<210> SEQ ID NO 33
<211> LENGTH: 118
<212> TYPE: DNA
<213> ORGANISM: Homo sapiens
<220> FEATURE:
<221> NAME/KEY: Transcript Start Site
<222> LOCATION: (1)..(18)

<400> SEQUENCE: 33

```
gcggtgcgag agcgcgcgag ccggcggcgg gggcgggcgg gcgggcagga ggccgggagg    60
agggaggcgg cggcggcggc ggcggcggcg gcgagagccc agagccagag cccggccg    118
```

<210> SEQ ID NO 34
<211> LENGTH: 154
<212> TYPE: DNA
<213> ORGANISM: Homo sapiens
<220> FEATURE:
<221> NAME/KEY: Transcript Start Site
<222> LOCATION: (1)..(54)

<400> SEQUENCE: 34

```
ggccagcggg gccaggggc gctccgcacc tgggcactcc cagcgatgcg cagcggggca     60
gcgccggccc cgccgatgga gctgctgttg ctgccgccgc cgccgcccgg agcgcccgc    120 tccgcccgcg ccccgtgcgc ctgagcaccg agct                               154
```

<210> SEQ ID NO 35
<211> LENGTH: 124
<212> TYPE: DNA
<213> ORGANISM: Homo sapiens
<220> FEATURE:
<221> NAME/KEY: Transcript Start Site
<222> LOCATION: (1)..(24)

<400> SEQUENCE: 35

```
gccgggagag cagcgcagaa gccgagccgc gaggagcgca ctccgtggcc ccgatggagc    60
ggtacaaagg tgagggcgcg ggttcctcgc gcggcgcaca cccactccct ttcgcccagc   120
gacg                                                                124
```

<210> SEQ ID NO 36
<211> LENGTH: 125
<212> TYPE: DNA
<213> ORGANISM: Homo sapiens
<220> FEATURE:
<221> NAME/KEY: Transcript Start Site
<222> LOCATION: (1)..(25)

<400> SEQUENCE: 36
ctgaaagcat catccaacaa ccacatccct tctctacaga agcctctgag aggaaagttc    60
ttcaccatgg actggacctg gagggtcttc tgcttgctgg ctgtagctcc aggtaaaggg   120
ccaac                                                               125

<210> SEQ ID NO 37
<211> LENGTH: 151
<212> TYPE: DNA
<213> ORGANISM: Homo sapiens
<220> FEATURE:
<221> NAME/KEY: Transcript Start Site
<222> LOCATION: (1)..(51)

<400> SEQUENCE: 37
gcggccaggc tgcccggccg gcggcgcgct ggaaatatga agagacgctg cagctgcggt    60
ggcggtggcg gccactgcag ctcagagcgg cgcacgcggc ggccggggcg ggacgcgggg   120
ccgggcgcgg agaagtcggg gcgggcggca g                                  151

<210> SEQ ID NO 38
<211> LENGTH: 116
<212> TYPE: DNA
<213> ORGANISM: Homo sapiens
<220> FEATURE:
<221> NAME/KEY: Transcript Start Site
<222> LOCATION: (1)..(16)

<400> SEQUENCE: 38
cagccctaca caacttgggg ccctctcct ctccagccct tctcctgtgt gcctgcctcc     60
tgccgccgcc accatgacca cctccatccg ccagttcacc tcctccagct ccatca       116

<210> SEQ ID NO 39
<211> LENGTH: 144
<212> TYPE: DNA
<213> ORGANISM: Homo sapiens
<220> FEATURE:
<221> NAME/KEY: Transcript Start Site
<222> LOCATION: (1)..(44)

<400> SEQUENCE: 39
ccggggatct tgcgcgcctc ccgaacagcc gtgttgtcgc cagggccgcg ccttccctcc    60
cacagcgcgc gctgcgcgtg cgaaggtctg gcggctcttg ggactggcgg ggctgcgcgc   120
ggggttaggg tgggggtacg ggaa                                          144

<210> SEQ ID NO 40
<211> LENGTH: 150
<212> TYPE: DNA
<213> ORGANISM: Homo sapiens
<220> FEATURE:
<221> NAME/KEY: Transcript Start Site
<222> LOCATION: (1)..(50)

<400> SEQUENCE: 40
ggacagcatt caggggtgta ccaggcccca gaggcagcgg aaagggagac tgtggggaac    60
taggagcaac agcaggtaca ctccaaattc tattgacggt tcgaaattcc cgctttctcc   120
atagagattc ctttcttcat atttcattac                                    150

<210> SEQ ID NO 41
<211> LENGTH: 111
<212> TYPE: DNA

<213> ORGANISM: Homo sapiens
<220> FEATURE:
<221> NAME/KEY: Transcript Start Site
<222> LOCATION: (1)..(11)

<400> SEQUENCE: 41
ggccgccgcg agtgactgca ccgagcccga gaagtcgccg cgccccgcag ccgccccgac    60
tggttccccg ccttgcccgt gggccccgcc gggatgggga accgccggga c            111

<210> SEQ ID NO 42
<211> LENGTH: 172
<212> TYPE: DNA
<213> ORGANISM: Homo sapiens
<220> FEATURE:
<221> NAME/KEY: Transcript Start Site
<222> LOCATION: (1)..(72)

<400> SEQUENCE: 42
cccctccctc cgcgcgcatc tgctcccgag tccccagccc cgtgctgata ggtgcagccc    60
ctggagtcgt ggctgtgggc ataggtgcca gggaggggag gcccgggtcg aaggcatagg   120
cagaattgga gccctgggtt gccaaagcgt cgcagctaag aagccggagc cc           172

<210> SEQ ID NO 43
<211> LENGTH: 111
<212> TYPE: DNA
<213> ORGANISM: Homo sapiens
<220> FEATURE:
<221> NAME/KEY: Transcript Start Site
<222> LOCATION: (1)..(11)

<400> SEQUENCE: 43
ctcttttccg gttagcgcgg cggcagaagc catgagcagc aaagtctctc gcgacaccca    60
gtgggaggca gtgcggaaag tcctgcacag gaaccagcgc tagcgccaca a             111

<210> SEQ ID NO 44
<211> LENGTH: 161
<212> TYPE: DNA
<213> ORGANISM: Homo sapiens
<220> FEATURE:
<221> NAME/KEY: Transcript Start Site
<222> LOCATION: (1)..(61)

<400> SEQUENCE: 44
ggcgcccgcc ccgcgtcggc agagttgggt tgcgcgggcg ccgaggactc tccggcggcc    60
gggctgctgt tgggcggcgg cgcggagcgg cggcgagct gtgcgggagg ggcggccccg   120
aggggcgggg cgggccgacg ccgcgtgtcc cgccgcagcc g                       161

<210> SEQ ID NO 45
<211> LENGTH: 116
<212> TYPE: DNA
<213> ORGANISM: Homo sapiens
<220> FEATURE:
<221> NAME/KEY: Transcript Start Site
<222> LOCATION: (1)..(16)

<400> SEQUENCE: 45
gggttagtgt gcctgtgttt agctctgggg aaagtcaaac tggattccat agggaaagcc    60
tgcaaatcac ttctatttta gcaaggagaa aacagaatct ccatccagca gggtcc       116

<210> SEQ ID NO 46
<211> LENGTH: 158
<212> TYPE: DNA

<213> ORGANISM: Homo sapiens
<220> FEATURE:
<221> NAME/KEY: Transcript Start Site
<222> LOCATION: (1)..(58)

<400> SEQUENCE: 46 gcaggggag agtgaactga cagactcagt cactgaagag ggaaaaggag tgagaagaca    60
aagccgtcaa agccccaaca gctttgtatt tctccagccc ggcgcagacc ccggagctcc   120
cgaggcactc cctccatctt tggaacacgc cagtaatt                           158

<210> SEQ ID NO 47
<211> LENGTH: 201
<212> TYPE: DNA
<213> ORGANISM: Homo sapiens
<220> FEATURE:
<221> NAME/KEY: Transcript Start Site
<222> LOCATION: (1)..(101)

<400> SEQUENCE: 47
ggagcggcag ggatttccgg gtcggaggca tctgaggggc gcaggggcgc gggtgcgtgg    60
gccactgggt gaccgactta gcctggccag actctcagca cctggaagcg ccccgagagt   120
gacagcgtga ggctgggagg gaggacttgg cttgagcttg ttaaactctg ctctgagcct   180
ccttgtcgcc tgcatttaga t                                             201

<210> SEQ ID NO 48
<211> LENGTH: 122
<212> TYPE: DNA
<213> ORGANISM: Homo sapiens
<220> FEATURE:
<221> NAME/KEY: Transcript Start Site
<222> LOCATION: (1)..(22)

<400> SEQUENCE: 48
tgggccgtga gagcgccgag acgcgcgggg cgcggagatg tgcaagtggc gaagcttgac    60
cgagagcagg ctggagcagc cgcccaactc ctggcgcggg atctgctgag gggtcacggt   120
ga                                                                  122

<210> SEQ ID NO 49
<211> LENGTH: 139
<212> TYPE: DNA
<213> ORGANISM: Homo sapiens

<400> SEQUENCE: 49
tactccctca gcagcgtggt gaccgtgccc tccagcaact tcggcaccca gacctacacc    60
tgcaacgtag atcacaagcc cagcaacacc aaggtggaca agacagttgg tgagaggcca   120
gctcagggag ggagggtgt                                                139

<210> SEQ ID NO 50
<211> LENGTH: 117
<212> TYPE: DNA
<213> ORGANISM: Homo sapiens
<220> FEATURE:
<221> NAME/KEY: Transcript Start Site
<222> LOCATION: (1)..(17)

<400> SEQUENCE: 50
cctgctcagt ctgggcctaa ggaagcagca ctggtggtgc ctcagccatg gcctggaccg    60
ttctcctcct cggcctcctc tctcactgca caggtgatcc ccagggtc tcaccaa        117

```
<210> SEQ ID NO 51
<211> LENGTH: 150
<212> TYPE: DNA
<213> ORGANISM: Homo sapiens
<220> FEATURE:
<221> NAME/KEY: Transcript Start Site
<222> LOCATION: (1)..(50)

<400> SEQUENCE: 51
gctggcaccg ggaacgcccg agcgccggca gagagcgcgg agagcgcgac acgtgcggcc      60
cagagcaccg gggccacccg gtccccgcag gcccgggacc gcgcccgctg gcaggcgaca     120
cgtggtgagt gaccagtgac tcggggtcgg                                      150

<210> SEQ ID NO 52
<211> LENGTH: 114
<212> TYPE: DNA
<213> ORGANISM: Homo sapiens
<220> FEATURE:
<221> NAME/KEY: Transcript Start Site
<222> LOCATION: (1)..(14)

<400> SEQUENCE: 52
aggctcagtc tgcgcgcagg accggcccaa gtccggggcg cccgtgtccc tcgcgtccct      60
cctcccggcc cgggcccctc gcccgtggcc gccccggccc cttttgcgga gagg           114

<210> SEQ ID NO 53
<211> LENGTH: 155
<212> TYPE: DNA
<213> ORGANISM: Homo sapiens
<220> FEATURE:
<221> NAME/KEY: Transcript Start Site
<222> LOCATION: (1)..(55)

<400> SEQUENCE: 53
ccggcgtccg gccttcccag cacccggccc agggctggag ctggctgcag ggctggcccg      60
cggcgacctg gcagggtgg cggctgctcc ctctcctccc accccgcccc gaggcgcagc     120
gcgcggcaga gcggctcggt gcccggcggg cgggc                                155

<210> SEQ ID NO 54
<211> LENGTH: 142
<212> TYPE: DNA
<213> ORGANISM: Homo sapiens
<220> FEATURE:
<221> NAME/KEY: Transcript Start Site
<222> LOCATION: (1)..(42)

<400> SEQUENCE: 54
tctgccacta gagaggtaca actgtgtttg agggtttgaa ggcgtgcgcg cgtgtgtgtg      60
tgtatgtgtg tgtgtgtgtc cttctgaaaa catagagcta ttgagtacaa aaatatggcc    120
atttcctcta aattttcttt cc                                              142

<210> SEQ ID NO 55
<211> LENGTH: 107
<212> TYPE: DNA
<213> ORGANISM: Homo sapiens
<220> FEATURE:
<221> NAME/KEY: Transcript Start Site
<222> LOCATION: (1)..(7)

<400> SEQUENCE: 55
tgacgctgag caaagcagac tacgagaaac acaaagtcta cgcctgcgaa gtcacccatc      60
agggcctgag ctcgcccgtc acaaagagct tcaacagggg agagtgt                   107
```

```
<210> SEQ ID NO 56
<211> LENGTH: 136
<212> TYPE: DNA
<213> ORGANISM: Homo sapiens
<220> FEATURE:
<221> NAME/KEY: Transcript Start Site
<222> LOCATION: (1)..(36)

<400> SEQUENCE: 56
cggcagagct gggagtgaca ctgacaagca atcggccgcg tccagagcag caggcggcat      60
ccggggggag cggggccggc tgggggggccc caggagggct tcctggaacc ccagctccat    120
ggccgcctgc accctg                                                    136

<210> SEQ ID NO 57
<211> LENGTH: 114
<212> TYPE: DNA
<213> ORGANISM: Homo sapiens
<220> FEATURE:
<221> NAME/KEY: Transcript Start Site
<222> LOCATION: (1)..(14)

<400> SEQUENCE: 57 ccgggggggca gaccccgcgg ccgccggccg gcgtccggcc ttcccagcac ccggcccagg     60
gctggagctg gctgcagggc tggcccgcgg cgacctgggc agggtggcgg ctgc           114

<210> SEQ ID NO 58
<211> LENGTH: 124
<212> TYPE: DNA
<213> ORGANISM: Homo sapiens
<220> FEATURE:
<221> NAME/KEY: Transcript Start Site
<222> LOCATION: (1)..(24)

<400> SEQUENCE: 58
cagtctcgtt ccctctcgac gcccccggag tcaagacgtg aagggagtgc caaggcggcc     60
gggggcggcg agcggggccg cgggcgcgca ccgactcaag agccgactgt cagcctcggc    120
gggc                                                                 124

<210> SEQ ID NO 59
<211> LENGTH: 120
<212> TYPE: DNA
<213> ORGANISM: Homo sapiens
<220> FEATURE:
<221> NAME/KEY: Transcript Start Site
<222> LOCATION: (1)..(20)

<400> SEQUENCE: 59
gggcgctttc ccaggcctgg ccgaggggcg tcgcgcagag gcggcggcgg cgcacggagg     60
cggcagacga cgcgctctcg gcgcccgcag ccccggtccc gcgctcccgc ggcccaaagt    120

<210> SEQ ID NO 60
<211> LENGTH: 115
<212> TYPE: DNA
<213> ORGANISM: Homo sapiens
<220> FEATURE:
<221> NAME/KEY: Transcript Start Site
<222> LOCATION: (1)..(15)

<400> SEQUENCE: 60
tcgccgcagt agcagctgga gcagcgacag aggcggcagc tgcggcggcg gcggcgcccg     60
cgcccctcgc gccagcgcgt agagcggcgg cggcagctcg ggggccgcca ctgcc          115
```

<210> SEQ ID NO 61
<211> LENGTH: 104
<212> TYPE: DNA
<213> ORGANISM: Homo sapiens
<220> FEATURE:
<221> NAME/KEY: Transcript Start Site
<222> LOCATION: (1)..(4)

<400> SEQUENCE: 61
gctctgggag aagagcccca gccccagaat tcccaggagt ttccattcgg tgatcagcac    60
tgaacacaga ggactcacca tggagtttgg gctgagctgg gttt                   104

<210> SEQ ID NO 62
<211> LENGTH: 120
<212> TYPE: DNA
<213> ORGANISM: Homo sapiens
<220> FEATURE:
<221> NAME/KEY: Transcript Start Site
<222> LOCATION: (1)..(20)

<400> SEQUENCE: 62
gcccccgcag tcgctgaagc ggccgcgccc gccgggggag ggagtagccg ctggggaggc    60
tccaagttgg cggagcggcg aggacccctg gactcctctg cgtcccgccc cgggagtggc   120

<210> SEQ ID NO 63
<211> LENGTH: 130
<212> TYPE: DNA
<213> ORGANISM: Homo sapiens
<220> FEATURE:
<221> NAME/KEY: Transcript Start Site
<222> LOCATION: (1)..(30)

<400> SEQUENCE: 63
agggaggggc ggcaggactc caggagcggc ggggccaggg cagcgcggac tcgcgtcccg    60
tggagcgttc caggcgggcg cgcggctttc tccccagacc caccgagtgg cggcggaggc   120
gagatgcgcg                                                         130

<210> SEQ ID NO 64
<211> LENGTH: 111
<212> TYPE: DNA
<213> ORGANISM: Homo sapiens
<220> FEATURE:
<221> NAME/KEY: Transcript Start Site
<222> LOCATION: (1)..(11)

<400> SEQUENCE: 64
agggtcgaag ccggggatga ggccgactat tactgtcagg tgtgggatag tagtagtgat    60
catcccacgg tgacacaggc agatgaggaa gtgagacaaa aacaccctcc c            111

<210> SEQ ID NO 65
<211> LENGTH: 114
<212> TYPE: DNA
<213> ORGANISM: Homo sapiens
<220> FEATURE:
<221> NAME/KEY: Transcript Start Site
<222> LOCATION: (1)..(14)

<400> SEQUENCE: 65
gggcggcagc ggcggcggcg gcggcggcg gggcagcggc aacccggcg ccgcggcaag     60 gactcggagg gctgagacgc ggcggcggcg gcgcggggag cgcggggcgc ggcg        114

```
<210> SEQ ID NO 66
<211> LENGTH: 140
<212> TYPE: DNA
<213> ORGANISM: Homo sapiens

<400> SEQUENCE: 66
gcagctccgc cctcgcaaag gcacagcgcg ggcgcaggcg cccagaggcg cacaggagac     60
ctcaggccca gactccactc cccagctgtg aaagggtaag aattgagggt ggctgaggct    120
cggggttgtt cagggcgggg                                                140

<210> SEQ ID NO 67
<211> LENGTH: 125
<212> TYPE: DNA
<213> ORGANISM: Homo sapiens
<220> FEATURE:
<221> NAME/KEY: Transcript Start Site
<222> LOCATION: (1)..(25)

<400> SEQUENCE: 67
ctgagagcat cacataacaa ccacattcct cctctgaaga agccctgggg agcacagctc     60
atcaccatgg actggacctg gaggttcctc tttgtggtgg cagcagctac aggtaagggg    120
cttcc                                                                125

<210> SEQ ID NO 68
<211> LENGTH: 119
<212> TYPE: DNA
<213> ORGANISM: Homo sapiens
<220> FEATURE:
<221> NAME/KEY: Transcript Start Site
<222> LOCATION: (1)..(19)

<400> SEQUENCE: 68
gcgcagccgc tcacctgcgg ggcagggcgc ggaggaggga cccgggctgc gcgctctcgg     60
gccgaggaac caggacgcgc ccggagcctc gcacgcggcc aagctcgggg cgtcccctc    119

<210> SEQ ID NO 69
<211> LENGTH: 119
<212> TYPE: DNA
<213> ORGANISM: Homo sapiens
<220> FEATURE:
<221> NAME/KEY: Transcript Start Site
<222> LOCATION: (1)..(19)

<400> SEQUENCE: 69
aggttcattt ccatagttcc ctgcggcctc tgccttgggg agttatgttt tgttaccgag     60
atccgcgcta ccagattgca ccggggctga tttgggggct gggaatttgc cattctgct    119

<210> SEQ ID NO 70
<211> LENGTH: 111
<212> TYPE: DNA
<213> ORGANISM: Homo sapiens
<220> FEATURE:
<221> NAME/KEY: Transcript Start Site
<222> LOCATION: (1)..(11)

<400> SEQUENCE: 70
ggccaagctc ggggcgtccc ctcccctcgg ccgggcgaac tcaaggggcg cagctctttg     60
ctttgacaga gctggccggc ggaggcgtgc agagcggcga gccggcgagc c             111

<210> SEQ ID NO 71
<211> LENGTH: 120
<212> TYPE: DNA
```

```
<213> ORGANISM: Homo sapiens
<220> FEATURE:
<221> NAME/KEY: Transcript Start Site
<222> LOCATION: (1)..(20)

<400> SEQUENCE: 71
cggcctgggc gctgagccga gcgccgggag agcagcgcag aagccgagcc gcgaggagcg      60
cactccgtgg ccccgatgga gcggtacaaa ggtgagggcg cgggttcctc gcgcggcgca     120

<210> SEQ ID NO 72
<211> LENGTH: 127
<212> TYPE: DNA
<213> ORGANISM: Homo sapiens
<220> FEATURE:
<221> NAME/KEY: Transcript Start Site
<222> LOCATION: (1)..(27)

<400> SEQUENCE: 72
aaccttaaat tatgtacaga gagagaaaga gagagaggga cttgagttct gttatcttct      60
taagtagatt catattgtaa gggtctcggg gtggggggt tggcaaaatc ctggagccag     120
aagaaag                                                              127

<210> SEQ ID NO 73
<211> LENGTH: 118
<212> TYPE: DNA
<213> ORGANISM: Homo sapiens
<220> FEATURE:
<221> NAME/KEY: Transcript Start Site
<222> LOCATION: (1)..(18)

<400> SEQUENCE: 73
gagacctggg ctggcgcggg cgggagctgc ggcggatacc cttgcgtgct gtggagaccc      60
tactctcttc gctgagaacg gccgctagcg gggactgaag gccgggagcc cactcccg      118

<210> SEQ ID NO 74
<211> LENGTH: 116
<212> TYPE: DNA
<213> ORGANISM: Homo sapiens
<220> FEATURE:
<221> NAME/KEY: Transcript Start Site
<222> LOCATION: (1)..(16)

<400> SEQUENCE: 74
ccgaggaacc aggacgcgcc cggagcctcg cacgcggcca agctcggggc gtccctccc       60 ctcggccggg cgaactcaag gggcgcagct ctttgctttg acagagctgg ccggcg         116

<210> SEQ ID NO 75
<211> LENGTH: 115
<212> TYPE: DNA
<213> ORGANISM: Homo sapiens
<220> FEATURE:
<221> NAME/KEY: Transcript Start Site
<222> LOCATION: (1)..(15)

<400> SEQUENCE: 75 aagactttg aaactttcc caatccctaa aagggacttg gcctctttt ctgggctcag          60 cggggcagcc gctcggaccc cggcgcgctg accctcgggg ctgccgattc gctgg          115

<210> SEQ ID NO 76
<211> LENGTH: 132
<212> TYPE: DNA
<213> ORGANISM: Homo sapiens
<220> FEATURE:
```

```
<221> NAME/KEY: Transcript Start Site
<222> LOCATION: (1)..(32)

<400> SEQUENCE: 76
agagctctca tttcctccca gcctcgtgcg ggaaatggct ttaattctga cggcagggct      60
gtgagggact agcgggaacc cgagccttt gtcaaggaac tgcggcgtcg gtggccagtc     120
atccccgccg cc                                                        132

<210> SEQ ID NO 77
<211> LENGTH: 134
<212> TYPE: DNA
<213> ORGANISM: Homo sapiens
<220> FEATURE:
<221> NAME/KEY: Transcript Start Site
<222> LOCATION: (1)..(34)

<400> SEQUENCE: 77
ggctgggcca gtcccagcgg cgcagccacc catgcgcgcg cgctcgcaag accaccagcg     60
cccagagccc cagtctgagg cttggcgccg ggggtctgcg ggcgagggga gctctctacg    120
tgcgaggggc tagc                                                      134

<210> SEQ ID NO 78
<211> LENGTH: 115
<212> TYPE: DNA
<213> ORGANISM: Homo sapiens
<220> FEATURE:
<221> NAME/KEY: Transcript Start Site
<222> LOCATION: (1)..(15)

<400> SEQUENCE: 78
cgaagcagag gcgccgccgc tgtcccggag caagccatgc cgcgcttgtc tctgctcttg     60
ccgctgctgc ttctgctgct gctgccgctg ctgccgccgc tgtccccgag ccttg        115

<210> SEQ ID NO 79
<211> LENGTH: 125
<212> TYPE: DNA
<213> ORGANISM: Homo sapiens
<220> FEATURE:
<221> NAME/KEY: Transcript Start Site
<222> LOCATION: (1)..(25)

<400> SEQUENCE: 79
ccgcgcagcg gccttttgtc agcgcgcagg gccaggagag ctctcatttc ctcccagcct     60
cgtgcgggaa atggctttaa ttctgacggc agggctgtga gggactagcg ggaacccgag    120
cctt                                                                 125

<210> SEQ ID NO 80
<211> LENGTH: 142
<212> TYPE: DNA
<213> ORGANISM: Homo sapiens
<220> FEATURE:
<221> NAME/KEY: Transcript Start Site
<222> LOCATION: (1)..(42)

<400> SEQUENCE: 80
gtgcgcctgc gcaatgcgcg cggtgatgga gcgctaaccg ggggcgcggc ggcggcgagg     60
gctcggcggg ccattggcta ccggccgcgg caaaggcagc ttggggaccc agcgtgcgcg    120
gggcccgcgg gccgggccgg gg                                             142

<210> SEQ ID NO 81
```

```
<211> LENGTH: 126
<212> TYPE: DNA
<213> ORGANISM: Homo sapiens
<220> FEATURE:
<221> NAME/KEY: Transcript Start Site
<222> LOCATION: (1)..(26)

<400> SEQUENCE: 81
ttgcccagag accatcacac aacagccaca tccctcccct acagaagccc ccagagcgca    60
gcacctcacc atggactgca cctggaggat cctcttcttg gtggcagcag ctacaggcaa   120
gagaat                                                              126

<210> SEQ ID NO 82
<211> LENGTH: 113
<212> TYPE: DNA
<213> ORGANISM: Homo sapiens
<220> FEATURE:
<221> NAME/KEY: Transcript Start Site
<222> LOCATION: (1)..(13)

<400> SEQUENCE: 82
ctaggcctag tcctggctgg gctcccgctg gagtgtgcgt tgggggcgga ccaggagcgg    60
tggtctccag ggaggtcgag gctggggctc ccacccggat ttggagcagg gtc          113

<210> SEQ ID NO 83
<211> LENGTH: 157
<212> TYPE: DNA
<213> ORGANISM: Homo sapiens
<220> FEATURE:
<221> NAME/KEY: Transcript Start Site
<222> LOCATION: (1)..(57)

<400> SEQUENCE: 83
ggctcagctc ccagcgcgcc cctcccgtct ccgcagcaaa aaagtttgag tcgccgctgc    60
cgggttgcca gcggagtcgc gcgtcgggag ctacgtaggg cagagaagtc atggcttctc   120
cgtccaaagg caatgacttg ttttcgcccg acgagga                            157

<210> SEQ ID NO 84
<211> LENGTH: 183
<212> TYPE: DNA
<213> ORGANISM: Homo sapiens
<220> FEATURE:
<221> NAME/KEY: Transcript Start Site
<222> LOCATION: (1)..(83)

<400> SEQUENCE: 84
ggctgggaca cacctactcc aactttctca gcagcctctc cggctgcggg ctgcgcgcct    60
tcctgctccg agtctctgca cctccctcag gagcctgtca gcctggccct cgtgagaggg   120
gcgccagccc agcagcctgc tctggggcac cctcccctac ctgaagggca caggtaagaa   180
ttg                                                                 183

<210> SEQ ID NO 85
<211> LENGTH: 129
<212> TYPE: DNA
<213> ORGANISM: Homo sapiens
<220> FEATURE:
<221> NAME/KEY: Transcript Start Site
<222> LOCATION: (1)..(29)

<400> SEQUENCE: 85
gcgcagctct ttgctttgac agagctggcc ggcggaggcg tgcagagcgg cgagccggcg    60
```

```
agccaggctg agaaactcga gccgggaaca agaggggtc ggactgagtg tgtgtgtcgg      120
ctcgagctc                                                             129
```

<210> SEQ ID NO 86
<211> LENGTH: 122
<212> TYPE: DNA
<213> ORGANISM: Homo sapiens
<220> FEATURE:
<221> NAME/KEY: Transcript Start Site
<222> LOCATION: (1)..(22)

<400> SEQUENCE: 86

```
ctcctctcag tcttggagtc tcttcgccca ggtggctgtg gatccggtac gggagttgcc      60
gccgcggtcc aactccccgc tgccgcccag cgcatccgct cgcaggtacc gccagcacct     120
gg                                                                    122
```

<210> SEQ ID NO 87
<211> LENGTH: 119
<212> TYPE: DNA
<213> ORGANISM: Homo sapiens
<220> FEATURE:
<221> NAME/KEY: Transcript Start Site
<222> LOCATION: (1)..(19)

<400> SEQUENCE: 87

```
ccctgcagct ctgggagagg agctccagcc ttgggattcc cagctgtctc cactcggtga      60
tcggcactga atacaggaga ctcaccatgg agtttgggct gagctgggtt ttccttgtt      119
```

<210> SEQ ID NO 88
<211> LENGTH: 121
<212> TYPE: DNA
<213> ORGANISM: Homo sapiens
<220> FEATURE:
<221> NAME/KEY: Transcript Start Site
<222> LOCATION: (1)..(21)

<400> SEQUENCE: 88

```
gctgaggtgt aaagggtctt ctgagctgca gtggcaatta gaccagaaga tccccgctcc      60
tgtctctaaa gaggggaaag ggcaaggatg gtggaggctt tctgtgctac ctggaagctg     120
a                                                                    121
```

<210> SEQ ID NO 89
<211> LENGTH: 168
<212> TYPE: DNA
<213> ORGANISM: Homo sapiens
<220> FEATURE:
<221> NAME/KEY: Transcript Start Site
<222> LOCATION: (1)..(68)

<400> SEQUENCE: 89

```
cgctaagcgg ggaggagcga ccgctacaat ggatcctccc gcaggctttg tgcgcgctgg      60
gaatccagct gtcgccgccc cgcagagccc cctgtccccg gagggcgctc atttccgggc     120
cgcccaccac ccgcgtagca ccggcagccg ctgtcccggc agtctcca                 168
```

<210> SEQ ID NO 90
<211> LENGTH: 171
<212> TYPE: DNA
<213> ORGANISM: Homo sapiens
<220> FEATURE:
<221> NAME/KEY: Transcript Start Site
<222> LOCATION: (1)..(71)

-continued

<400> SEQUENCE: 90
ccctcccccg cgcccggctc ctttgaattt ggcccggcgc ggtgtgcgcg cggctcgggc    60
ggacgcggcg gctgctgccg gggagcgagc cggcggcgcg ggcgagccga gcgcggtaag   120
tgcggcgccg ccgccggcgc gccctccttc ctttatgggg tcctagtgcc g            171

<210> SEQ ID NO 91
<211> LENGTH: 115
<212> TYPE: DNA
<213> ORGANISM: Homo sapiens
<220> FEATURE:
<221> NAME/KEY: Transcript Start Site
<222> LOCATION: (1)..(15)

<400> SEQUENCE: 91
cgagccggaa tcagcctccc tccgcggacc tgacgctggg caggtaactc ccctcccctc    60
cctgcccgcg cccaggcgct tgctgcttcc tgggaggcaa accttcggcg gccgg        115

<210> SEQ ID NO 92
<211> LENGTH: 119
<212> TYPE: DNA
<213> ORGANISM: Homo sapiens
<220> FEATURE:
<221> NAME/KEY: Transcript Start Site
<222> LOCATION: (1)..(19)

<400> SEQUENCE: 92
gcctgggcgt cactgaggca gtagccggcc gggtgaggag ggcggttgcc ggcgcggcgc    60
ggcgcggcgc gggtggggcg ggggttccgc cggcttccag tcccctttcc cgccgccgc   119

<210> SEQ ID NO 93
<211> LENGTH: 113
<212> TYPE: DNA
<213> ORGANISM: Homo sapiens
<220> FEATURE:
<221> NAME/KEY: Transcript Start Site
<222> LOCATION: (1)..(13)

<400> SEQUENCE: 93
gggctgagct cgccgggccg gccccctccgt ggggccgcgc tgggacgcac gcgggtggac    60
gaggggaccg atcccgggcg cccatggccg gggccgccat ggccgagcgg ggc          113

<210> SEQ ID NO 94
<211> LENGTH: 117
<212> TYPE: DNA
<213> ORGANISM: Homo sapiens
<220> FEATURE:
<221> NAME/KEY: Transcript Start Site
<222> LOCATION: (1)..(17)

<400> SEQUENCE: 94
tcagccagca gtcagccggc cggagacaga gacttcacga ctcccagtct cctcctcgcc    60
gcggccgccg cctcctccttt ctctcctcct cctcttcctc ctcctccctc gctccca    117

<210> SEQ ID NO 95
<211> LENGTH: 177
<212> TYPE: DNA
<213> ORGANISM: Homo sapiens
<220> FEATURE:
<221> NAME/KEY: Transcript Start Site
<222> LOCATION: (1)..(77)

<400> SEQUENCE: 95

```
tgagtatggg tctaggaagt gagagcaatg taaaacaata gaaagcaaca gttcagagca      60
ctgcatcaag tgtactgtgc tggaaaggtc cgccatagga aatatggtcc tccatactcc     120
tcagacaaca gccttccgaa agcaaacctg tccctacctg cagatgatta accatct       177

<210> SEQ ID NO 96
<211> LENGTH: 118
<212> TYPE: DNA
<213> ORGANISM: Homo sapiens
<220> FEATURE:
<221> NAME/KEY: Transcript Start Site
<222> LOCATION: (1)..(18)

<400> SEQUENCE: 96
ggccggtgtc cgcgccagcc cgggacgcgc ttggccttgc ccgcgcccgc tcgcctcgtc      60
tcgcccggcc tccccgcgtc gcctcgtcgc ctgttccgcg ccaggcatgg cccccagc      118

<210> SEQ ID NO 97
<211> LENGTH: 120
<212> TYPE: DNA
<213> ORGANISM: Homo sapiens
<220> FEATURE:
<221> NAME/KEY: Transcript Start Site
<222> LOCATION: (1)..(20)

<400> SEQUENCE: 97
ctgattgaga aatccgcgcg cagcctccgc cgctgcacac tgcagcctct gctgaacccc      60
tgccgcgccg ccgccttcgc cagcccggac cggaccggcc cgccttccct tcctccgctc     120

<210> SEQ ID NO 98
<211> LENGTH: 130
<212> TYPE: DNA
<213> ORGANISM: Homo sapiens
<220> FEATURE:
<221> NAME/KEY: Transcript Start Site
<222> LOCATION: (1)..(30)

<400> SEQUENCE: 98
tgaccgtgcc ctccagcagc ttgggcacga agacctacac ctgcaacgta gatcacaagc      60
ccagcaacac caaggtggac aagagagttg gtgagaggcc agcacaggga gggagggtgt     120
ctgctggaag                                                            130

<210> SEQ ID NO 99
<211> LENGTH: 134
<212> TYPE: DNA
<213> ORGANISM: Homo sapiens
<220> FEATURE:
<221> NAME/KEY: Transcript Start Site
<222> LOCATION: (1)..(34)

<400> SEQUENCE: 99
aaatcccttt ccaatgagcc tccctcagaa accatggagg aaatagagca cacatgccca      60
cagcctcgac tggtaagtaa agacaaagga tggaaatgta tgcgtggcta tggcataaaa     120
gagttcctta tgcg                                                       134

<210> SEQ ID NO 100
<211> LENGTH: 122
<212> TYPE: DNA
<213> ORGANISM: Homo sapiens
<220> FEATURE:
<221> NAME/KEY: Transcript Start Site
<222> LOCATION: (1)..(22)
```

```
<400> SEQUENCE: 100
ccacccacgc actcatttgg cagctatcaa cggagtattc acagtacgct gctcacagtt    60
ctaaccgcgg aggatagagt tgaggcccac acgacagccc ctgctctcac agaactgatg   120
tc                                                                  122

<210> SEQ ID NO 101
<211> LENGTH: 120
<212> TYPE: DNA
<213> ORGANISM: Homo sapiens
<220> FEATURE:
<221> NAME/KEY: Transcript Start Site
<222> LOCATION: (1)..(20)

<400> SEQUENCE: 101
tctcgcccaa ctcccagaca cctcgcgggc tctgcagcac cggcaccgtt tccaggaggc    60
ctggcggggt gtgcgtccag ccgttgggcg cttttctttttt ggacctcggg gccatccaca  120

<210> SEQ ID NO 102
<211> LENGTH: 158
<212> TYPE: DNA
<213> ORGANISM: Homo sapiens
<220> FEATURE:
<221> NAME/KEY: Transcript Start Site
<222> LOCATION: (1)..(58)

<400> SEQUENCE: 102
cccgccccgc cccgccacag ccgctgctgc cgcagcatcg gcatcgcaga cgcgctcggg    60
cggcgggtcc gaggccggcg tgcgcggagg ctgggcgggc agcccgagcg gtggccgcag   120
cgcaggtaag gcgggctggc ctccccgtgc gacccggg                           158

<210> SEQ ID NO 103
<211> LENGTH: 113
<212> TYPE: DNA
<213> ORGANISM: Homo sapiens
<220> FEATURE:
<221> NAME/KEY: Transcript Start Site
<222> LOCATION: (1)..(13)

<400> SEQUENCE: 103
ctgctccgag cccggacgcc gccgcccacc agtcagccgg cgtccccatg gcccggtccg    60
cgacactggc ggccgccgcc ctggcgctgt gcctgctgct ggcgccgcct ggc          113

<210> SEQ ID NO 104
<211> LENGTH: 123
<212> TYPE: DNA
<213> ORGANISM: Homo sapiens
<220> FEATURE:
<221> NAME/KEY: Transcript Start Site
<222> LOCATION: (1)..(23)

<400> SEQUENCE: 104
ggcctgggct gtggctgtga ctggcgctgc cgtgggcgcc gcagccctcg cgggagccgg    60
acgcggtaat gccccagcgg cgcagcgggc ggctgcgtcc ctgagccgct atataagcgc   120
ggc                                                                 123

<210> SEQ ID NO 105
<211> LENGTH: 119
<212> TYPE: DNA
<213> ORGANISM: Homo sapiens
<220> FEATURE:
<221> NAME/KEY: Transcript Start Site
```

<222> LOCATION: (1)..(19)

<400> SEQUENCE: 105
gaacctatca tttgaattag ccgagtcagg caggaggggg cggggaatcc ttccgccctt    60
cttaggaggg gctgcattgc aggggagag tgaactgaca gactcagtca ctgaagagg    119

<210> SEQ ID NO 106
<211> LENGTH: 142
<212> TYPE: DNA
<213> ORGANISM: Homo sapiens
<220> FEATURE:
<221> NAME/KEY: Transcript Start Site
<222> LOCATION: (1)..(42)

<400> SEQUENCE: 106
gcgctcattt ccgggccgcc caccacccgc gtagcaccgg cagccgctgt cccggcagtc    60
tccagccgtc ccgcccgctt gtggccaact ggctccagtc actccccgaa atgccagtcg    120
acttcactgg gtactggaag at    142

<210> SEQ ID NO 107
<211> LENGTH: 115
<212> TYPE: DNA
<213> ORGANISM: Homo sapiens
<220> FEATURE:
<221> NAME/KEY: Transcript Start Site
<222> LOCATION: (1)..(15)

<400> SEQUENCE: 107
cacaaagtct acgcctgcga agtcacccat cagggcctga gctcgcccgt cacaaagagc    60
ttcaacaggg gagagtgtta gagggagaag tgcccccacc tgctcctcag ttcca    115

<210> SEQ ID NO 108
<211> LENGTH: 160
<212> TYPE: DNA
<213> ORGANISM: Homo sapiens
<220> FEATURE:
<221> NAME/KEY: Transcript Start Site
<222> LOCATION: (1)..(60)

<400> SEQUENCE: 108
gagctaacga gacatctagt acggggctca caggtaacag aactctgatc agatccgccc    60
cggctcccac acagctataa ggttgcctgc ctgcctgcac agaaatgacg aaggacaaaa    120
acagcccagg gtaggtggga tctatcagcc tccatctgtt    160

<210> SEQ ID NO 109
<211> LENGTH: 135
<212> TYPE: DNA
<213> ORGANISM: Homo sapiens
<220> FEATURE:
<221> NAME/KEY: Transcript Start Site
<222> LOCATION: (1)..(35)

<400> SEQUENCE: 109
ctgcggtggc ggtggcggcc actgcagctc agagcggcgc acgcggcggc cggggcggga    60
cgcggggccg ggcgcggaga agtcggggcg ggcggcagag aggccgggac gcggaccggg    120
ccggggcgcc cacag    135

<210> SEQ ID NO 110
<211> LENGTH: 113
<212> TYPE: DNA
<213> ORGANISM: Homo sapiens

```
<220> FEATURE:
<221> NAME/KEY: Transcript Start Site
<222> LOCATION: (1)..(13)

<400> SEQUENCE: 110
cctagccagt cggcctccgg cggaggcaac gggggaggcc cgagggcggg cggtggagcg      60
cggcgcgcgg cggcggtgcc ccaagtgggt gcctcctccc ggccccgcac ggc            113

<210> SEQ ID NO 111
<211> LENGTH: 115
<212> TYPE: DNA
<213> ORGANISM: Homo sapiens
<220> FEATURE:
<221> NAME/KEY: Transcript Start Site
<222> LOCATION: (1)..(15)

<400> SEQUENCE: 111
ggccggaagc cgcgaggagc gcggacggct gggctgctgc tgggcggccg cggggcagcg      60
gagggcgccg gcactccggt ccccgccgct ccccgtcccc gctgctccta gcccc         115

<210> SEQ ID NO 112
<211> LENGTH: 150
<212> TYPE: DNA
<213> ORGANISM: Homo sapiens
<220> FEATURE:
<221> NAME/KEY: Transcript Start Site
<222> LOCATION: (1)..(50)

<400> SEQUENCE: 112
ttaagctctg tcagtaattt ctccoctagc aagaatgagg aagatgaaga gctcgggtat      60
ctgagggctg gtgtgtctgc atgcgtgtgt gttttggggg ccgactgaag gaagagaagg    120
ctggagagag ggaacatggg tctgagggca                                    150

<210> SEQ ID NO 113
<211> LENGTH: 145
<212> TYPE: DNA
<213> ORGANISM: Homo sapiens
<220> FEATURE:
<221> NAME/KEY: Transcript Start Site
<222> LOCATION: (1)..(45)

<400> SEQUENCE: 113
ctcgggagcc cgagcggtgg cggagcggcg agcagcgagc agcgcctgcg ggagcggccg      60
gtcggtcggg tccccgcgcc ccgcacgccc gcacgcccag cggggcccgc attgagcatg    120
ggcgcggcgg ccgtgcgctg gcact                                          145

<210> SEQ ID NO 114
<211> LENGTH: 135
<212> TYPE: DNA
<213> ORGANISM: Homo sapiens
<220> FEATURE:
<221> NAME/KEY: Transcript Start Site
<222> LOCATION: (1)..(35)

<400> SEQUENCE: 114
accacgcccg tcaagctcag ctgcatcctg actctgggtt ggaaacttcg tggtggatga      60
tgcctgtaac tacccagatg aaatcaagac gcaacagccc tcatcgaggg atgctcaggt    120
gagagatcct cagca                                                    135

<210> SEQ ID NO 115
<211> LENGTH: 135
```

<212> TYPE: DNA
<213> ORGANISM: Homo sapiens
<220> FEATURE:
<221> NAME/KEY: Transcript Start Site
<222> LOCATION: (1)..(35)

<400> SEQUENCE: 115
tcagccaggc agcactcgtt gctctttta aactccacgg caccagggat gaagtcacct   60
ttcttctttt aaaacgaaca catttgctct gtgagtccct gtcacttctg ttagaactta  120 gtatttttc cactg                                                    135

<210> SEQ ID NO 116
<211> LENGTH: 120
<212> TYPE: DNA
<213> ORGANISM: Homo sapiens
<220> FEATURE:
<221> NAME/KEY: Transcript Start Site
<222> LOCATION: (1)..(20)

<400> SEQUENCE: 116
caaggtctcc aacaaaggcc tcccgtcctc catcgagaaa accatctcca aagccaaagg   60
tgggacccac ggggtgcgag ggccacatgg acagaggtca gctcggccca ccctctgccc  120

<210> SEQ ID NO 117
<211> LENGTH: 113
<212> TYPE: DNA
<213> ORGANISM: Homo sapiens
<220> FEATURE:
<221> NAME/KEY: Transcript Start Site
<222> LOCATION: (1)..(13)

<400> SEQUENCE: 117
ccgcggtagg gccggagcc ggcgagtgct cccgggaact ctgcctgcgc ggcggcagcg    60
accggaggcc aggcccagca cgccggagct ggcctgctgg ggaggggcgg gag         113

<210> SEQ ID NO 118
<211> LENGTH: 115
<212> TYPE: DNA
<213> ORGANISM: Homo sapiens
<220> FEATURE:
<221> NAME/KEY: Transcript Start Site
<222> LOCATION: (1)..(15)

<400> SEQUENCE: 118
tacatcattg aagggtaaaa tttttcacca gagtaaactt gagaaaccaa ctggaccttg   60
agtattgtac attttgcctc gtggacccaa aggtaacatt aattgaccat gtttc       115

<210> SEQ ID NO 119
<211> LENGTH: 115
<212> TYPE: DNA
<213> ORGANISM: Homo sapiens
<220> FEATURE:
<221> NAME/KEY: Transcript Start Site
<222> LOCATION: (1)..(15)

<400> SEQUENCE: 119
ccagcaaagc caccaccaaa gccaccaccc aagccagcac caaggccacc accatatcct   60
cccccaaagc cactaccaaa gctgctgctg ctgctgctga agccaccgcc atagc        115

<210> SEQ ID NO 120
<211> LENGTH: 124
<212> TYPE: DNA
<213> ORGANISM: Homo sapiens

```
<220> FEATURE:
<221> NAME/KEY: Transcript Start Site
<222> LOCATION: (1)..(24)

<400> SEQUENCE: 120
caggtacccc ctaagcctgc actctgggcg ctcctgctgg cgctgctggg gaccgcgcca      60
agccgcgcct attccccggc ctgcagcgtc cccgacgtgc tccgccacta tcgcgccatc     120
atct                                                                  124

<210> SEQ ID NO 121
<211> LENGTH: 126
<212> TYPE: DNA
<213> ORGANISM: Homo sapiens
<220> FEATURE:
<221> NAME/KEY: Transcript Start Site
<222> LOCATION: (1)..(26)

<400> SEQUENCE: 121
cttggggagt tatgttttgt taccgagatc cgcgctacca gattgcaccg gggctgattt      60
gggggctggg aatttgccat tctgctgtac agacactgat ttttttttct tctttttaaa    120
aagcaa                                                                126

<210> SEQ ID NO 122
<211> LENGTH: 121
<212> TYPE: DNA
<213> ORGANISM: Homo sapiens
<220> FEATURE:
<221> NAME/KEY: Transcript Start Site
<222> LOCATION: (1)..(21)

<400> SEQUENCE: 122
ccgggttgcc agcggagtcg cgcgtcggga gctacgtagg gcagagaagt catggcttct      60
ccgtccaaag gcaatgactt gttttcgccc gacgaggagg gcccagcagt ggtggccgga    120
c                                                                     121

<210> SEQ ID NO 123
<211> LENGTH: 141
<212> TYPE: DNA
<213> ORGANISM: Homo sapiens
<220> FEATURE:
<221> NAME/KEY: Transcript Start Site
<222> LOCATION: (1)..(41)

<400> SEQUENCE: 123
ggctgcgcgc gccgccgact caccgagcga agcctgcacc gtctcggccg cggagaaggc      60
gagcagcgag ccctctttgg ccaggaagcc tttgccgtcc tccgcgtcag cctgcagcgc    120
ctccgccttg tcgaagttac c                                               141

<210> SEQ ID NO 124
<211> LENGTH: 120
<212> TYPE: DNA
<213> ORGANISM: Homo sapiens
<220> FEATURE:
<221> NAME/KEY: Transcript Start Site
<222> LOCATION: (1)..(20)

<400> SEQUENCE: 124
cgcccgctcc ctctccgcga gcctcgcgcc gcgcgggttg cctggcccag accgccgctg      60
ctgtctgcgg ggtctggtgc cggggcctga gtctctgctg gctaagccga cgcctcagcc    120
```

<210> SEQ ID NO 125
<211> LENGTH: 143
<212> TYPE: DNA
<213> ORGANISM: Homo sapiens
<220> FEATURE:
<221> NAME/KEY: Transcript Start Site
<222> LOCATION: (1)..(43)

<400> SEQUENCE: 125

```
tcgaatcagg aagatgttga caaagccagt tcttctaact cagcatgcga gaccgggtcc     60
gtttctgcgt tgtttcagaa gatcaaaggc atactccctg ttaaaatgga aagtgcagaa    120
tgtttggaaa tgacctatgt tcc                                            143
```

<210> SEQ ID NO 126
<211> LENGTH: 115
<212> TYPE: DNA
<213> ORGANISM: Homo sapiens
<220> FEATURE:
<221> NAME/KEY: Transcript Start Site
<222> LOCATION: (1)..(15)

<400> SEQUENCE: 126

```
ctgggtaaca gagccacctt ctgcgtcctg ctgagctctg ttctctccag cacctcccaa     60
cccactagtg cctggttctc ttgctccacc aggaacaagc caccatgtct cgcca         115
```

<210> SEQ ID NO 127
<211> LENGTH: 113
<212> TYPE: DNA
<213> ORGANISM: Homo sapiens
<220> FEATURE:
<221> NAME/KEY: Transcript Start Site
<222> LOCATION: (1)..(13)

<400> SEQUENCE: 127

```
cccgaggcag atccaggcgg cggcggaggc ggcgggcgca ggagagcggc tcccagggct     60
gaagtggccg ccaccaccgc cgcctgcgcc tggagcccgg tggccgccgg acg           113
```

<210> SEQ ID NO 128
<211> LENGTH: 128
<212> TYPE: DNA
<213> ORGANISM: Homo sapiens
<220> FEATURE:
<221> NAME/KEY: Transcript Start Site
<222> LOCATION: (1)..(28)

<400> SEQUENCE: 128

```
ccggggcctc ccgcctcctc ccccatcccc ctgcctcccc tgggcactgt ggcttcctcc     60
tgcgcctggt tgattcagcc cacctctctg catcccgctt cccgcgtctc ttctctgcac    120
tcctgccg                                                             128
```

<210> SEQ ID NO 129
<211> LENGTH: 150
<212> TYPE: DNA
<213> ORGANISM: Homo sapiens
<220> FEATURE:
<221> NAME/KEY: Transcript Start Site
<222> LOCATION: (1)..(50)

<400> SEQUENCE: 129

```
cccactcccc cttccttcca gtcccgctca gcccgggcac atcctccggc tgcccgcgca     60
cctctccacg ccggccccgt tccgcggctc gcctcggct gcgctcggct cccgcgggcg    120
ctcggccccg agcccctcct cccccctaccc                                    150
```

```
<210> SEQ ID NO 130
<211> LENGTH: 129
<212> TYPE: DNA
<213> ORGANISM: Homo sapiens
<220> FEATURE:
<221> NAME/KEY: Transcript Start Site
<222> LOCATION: (1)..(29)

<400> SEQUENCE: 130
ccctacagta gaacaagttt gcccattcat ccttgtgata gatatgcatg caaaaccaaa      60
atgaaatcaa atccccacag atggctcgta agtcaaaaac actgtttaat tctttcactg     120
catcccttt                                                             129

<210> SEQ ID NO 131
<211> LENGTH: 119
<212> TYPE: DNA
<213> ORGANISM: Homo sapiens
<220> FEATURE:
<221> NAME/KEY: Transcript Start Site
<222> LOCATION: (1)..(19)

<400> SEQUENCE: 131
gcggcagagg aggcggcggg cgctgggaga caccggacgc ccgctcggct gcgctgcggc      60
tcaggccccc gctcgggccc gacccgctcg gtcaccgccg gctcgggcgc gcacctgcc      119

<210> SEQ ID NO 132
<211> LENGTH: 114
<212> TYPE: DNA
<213> ORGANISM: Homo sapiens
<220> FEATURE:
<221> NAME/KEY: Transcript Start Site
<222> LOCATION: (1)..(14)

<400> SEQUENCE: 132
acctcacact ctccttgggc aggacctgct gcagctgctc tcggggttgg aggggaggtt      60
cctaggtcaa tggagttgtg tacctaggag gattatggct gcctctgctg agtc           114

<210> SEQ ID NO 133
<211> LENGTH: 164
<212> TYPE: DNA
<213> ORGANISM: Homo sapiens
<220> FEATURE:
<221> NAME/KEY: Transcript Start Site
<222> LOCATION: (1)..(64)

<400> SEQUENCE: 133
cgcacccgcg cgcctgtatc ccgtgctgtt tccctggcag acacacaggc gctcacgagt      60
ctctccttgc cagcctgcag ggcggcgacc cccaaaaccc agctccgggt cccaacctag     120
gcaagaagct gcttctctgc caacagctcc tcttcggcct ccgt                      164

<210> SEQ ID NO 134
<211> LENGTH: 149
<212> TYPE: DNA
<213> ORGANISM: Homo sapiens
<220> FEATURE:
<221> NAME/KEY: Transcript Start Site
<222> LOCATION: (1)..(49)

<400> SEQUENCE: 134
tccgtctcgc cccagtttg taatctgaca cagtacactg cagttgtctc cgaggtgaac       60
ctccggagcc ttggcacagc tcgcttctaa aggtaggctg agatttattt ttttctccta     120
```

```
aaaatagctt cccgtctccc ctcgccttt                                    149
```

<210> SEQ ID NO 135
<211> LENGTH: 127
<212> TYPE: DNA
<213> ORGANISM: Homo sapiens
<220> FEATURE:
<221> NAME/KEY: Transcript Start Site
<222> LOCATION: (1)..(27)

<400> SEQUENCE: 135

```
gggagggcgg gcctgtcgca gccgcgctgg tcgccaggcg tccgggagga gcggggtccg    60
cgcggcggac gaggcggggg cggaggcgca ggcagagcga gcgcgggagg tcgccgcagc   120
cagggac                                                             127
```

<210> SEQ ID NO 136
<211> LENGTH: 152
<212> TYPE: DNA
<213> ORGANISM: Homo sapiens
<220> FEATURE:
<221> NAME/KEY: Transcript Start Site
<222> LOCATION: (1)..(52)

<400> SEQUENCE: 136

```
gctggtgaat cacgtcacgg tggagcacgt gggaggcccc gagcagagca gccacgtctg    60
cttctgggag gactgtccgc gcgagggcaa gcccttcaag gccaaataca agctcatcaa   120
ccacatccgc gtgcacaccg gcgagaagcc ct                                 152
```

<210> SEQ ID NO 137
<211> LENGTH: 119
<212> TYPE: DNA
<213> ORGANISM: Homo sapiens
<220> FEATURE:
<221> NAME/KEY: Transcript Start Site
<222> LOCATION: (1)..(19)

<400> SEQUENCE: 137

```
cgcgcggaga ggcagacgcg aggagggagg cggctgagca gcgcgggcgg ctctgcggcg    60
ggcgcggtgg gcgcgggcgg cggggccccg ggatccccgc gcgcctcctc cgcgcggcg    119
```

<210> SEQ ID NO 138
<211> LENGTH: 116
<212> TYPE: DNA
<213> ORGANISM: Homo sapiens
<220> FEATURE:
<221> NAME/KEY: Transcript Start Site
<222> LOCATION: (1)..(16)

<400> SEQUENCE: 138

```
aatattcagc tgccactttt caccgttaga agtagagctt tttccagacc tcctaccttt    60
tagtctactt tgaaaggtga aagaaagaac atcgtttcag gaataaaaat gcacag       116
```

<210> SEQ ID NO 139
<211> LENGTH: 122
<212> TYPE: DNA
<213> ORGANISM: Homo sapiens
<220> FEATURE:
<221> NAME/KEY: Transcript Start Site
<222> LOCATION: (1)..(22)

<400> SEQUENCE: 139

```
tccacaaagc cttgcttgcc tgcaaacctt tacttctgaa atgacttcca cggctgggac    60
```

```
gggaaccttc cacccacagc tatgcctctg attggtgaat ggtgaaggtg cctgtctaac    120
tt                                                                  122

<210> SEQ ID NO 140
<211> LENGTH: 127
<212> TYPE: DNA
<213> ORGANISM: Homo sapiens
<220> FEATURE:
<221> NAME/KEY: Transcript Start Site
<222> LOCATION: (1)..(27)

<400> SEQUENCE: 140
cccctccctc cagctccctg cactgcgccc tgggtgggtg ggtgaatgtg aagaggcggc    60
gttgggctag gccctgcag cccgctcgga gcgtcctagg cccggggctg cgctgtgaaa    120
gacccag                                                             127

<210> SEQ ID NO 141
<211> LENGTH: 127
<212> TYPE: DNA
<213> ORGANISM: Homo sapiens
<220> FEATURE:
<221> NAME/KEY: Transcript Start Site
<222> LOCATION: (1)..(27)

<400> SEQUENCE: 141
tgcagcatca gacttagcag catcttcctg tcccaagaga agaggggatg ggaggatggc    60
atggttcagg gcttagggga ggataggga gaaaaagtgg aagcaaaggg agaggcccag    120
gaaggat                                                             127

<210> SEQ ID NO 142
<211> LENGTH: 124
<212> TYPE: DNA
<213> ORGANISM: Homo sapiens
<220> FEATURE:
<221> NAME/KEY: Transcript Start Site
<222> LOCATION: (1)..(24)

<400> SEQUENCE: 142
tcctaactca tttactttgc agatgaacta tggcgcgtac taagcagacg gctcgtaaat    60
ccacaggcgg taaagcaccg cgcaaacagc tggccactaa ggcagctcgc aagagcgctc    120
cggc                                                                124

<210> SEQ ID NO 143
<211> LENGTH: 129
<212> TYPE: DNA
<213> ORGANISM: Homo sapiens
<220> FEATURE:
<221> NAME/KEY: Transcript Start Site
<222> LOCATION: (1)..(29)

<400> SEQUENCE: 143
ctaaacctca caaatcagac tacccagctc tgctccgcag gggaagggag actgagccct    60
gggccaggct tggcagagag ggaagcggga ggacgacc ccagggcatt gtgggaacac     120
tggccaggc                                                           129

<210> SEQ ID NO 144
<211> LENGTH: 147
<212> TYPE: DNA
<213> ORGANISM: Homo sapiens
<220> FEATURE:
```

<221> NAME/KEY: Transcript Start Site
<222> LOCATION: (1)..(47)

<400> SEQUENCE: 144

```
gtccccgcgc cgctcgctcc cgcgcgccgc ctcagcatcc tcaggcccgg cggcagcccc      60
cgcagtcgct gaagcggccg cgcccgccgg gggagggagt agccgctggg gaggctccaa     120
gttggcggag cggcgaggac ccctgga                                         147
```

<210> SEQ ID NO 145
<211> LENGTH: 130
<212> TYPE: DNA
<213> ORGANISM: Homo sapiens
<220> FEATURE:
<221> NAME/KEY: Transcript Start Site
<222> LOCATION: (1)..(30)

<400> SEQUENCE: 145

```
tggctcatcc tgacttccgc tttggaggcg aggacccgag cgagtgtagg gggtgcggcg      60
tctggtcagc caggggtgaa ttctcaggac tggtcggcag tcaaggtgag gaccctgagt     120
gtaaactgaa                                                            130
```

<210> SEQ ID NO 146
<211> LENGTH: 118
<212> TYPE: DNA
<213> ORGANISM: Homo sapiens
<220> FEATURE:
<221> NAME/KEY: Transcript Start Site
<222> LOCATION: (1)..(18)

<400> SEQUENCE: 146

```
ccgcggccag tagtttgcgg catccggagg agcagcagca gcagtagcgg cggcggctgg      60
cgcagcgcgg agacggacga gcgggcacag acggcagcac agctcccgtg caccatgc      118
```

<210> SEQ ID NO 147
<211> LENGTH: 126
<212> TYPE: DNA
<213> ORGANISM: Homo sapiens
<220> FEATURE:
<221> NAME/KEY: Transcript Start Site
<222> LOCATION: (1)..(26)

<400> SEQUENCE: 147

```
catcgtgggg gaacggggcc gcctggactc agagctgaga acatgcagg acctggtgga       60
agacttcaag aacaagtgag ttggggtgga gggtggacac aggggagggt ggtgtcttct    120
tggtac                                                               126
```

<210> SEQ ID NO 148
<211> LENGTH: 116
<212> TYPE: DNA
<213> ORGANISM: Homo sapiens
<220> FEATURE:
<221> NAME/KEY: Transcript Start Site
<222> LOCATION: (1)..(16)

<400> SEQUENCE: 148

```
aagccccggg acggcgaggc aggcgctcag agccccgcag cctggcccgt gaccccgcag      60
agacgctgag gaccgcgacg gtgaggccct acgtccgcca gcacacccgg gcccgc        116
```

<210> SEQ ID NO 149
<211> LENGTH: 113
<212> TYPE: DNA

```
<213> ORGANISM: Homo sapiens
<220> FEATURE:
<221> NAME/KEY: Transcript Start Site
<222> LOCATION: (1)..(13)

<400> SEQUENCE: 149
aaagtaataa acagggcagc ttggaagagg tacctgcttt ctaataattg cctttagtgg    60
gaacagaagt ctcctttcaa gaagctttta attcatttta agatttaatt tta          113

<210> SEQ ID NO 150
<211> LENGTH: 124
<212> TYPE: DNA
<213> ORGANISM: Homo sapiens
<220> FEATURE:
<221> NAME/KEY: Transcript Start Site
<222> LOCATION: (1)..(24)

<400> SEQUENCE: 150
ctttggagac aaaccattcg actcgtggcg tctgcatcaa gtctgaaagc agacgcgcaa    60
ctttcgcaga atccacctta aaatctctgc cttaaactgc accagccccc aaaaaatcca   120
aggg                                                                124

<210> SEQ ID NO 151
<211> LENGTH: 216
<212> TYPE: DNA
<213> ORGANISM: Homo sapiens
<220> FEATURE:
<221> NAME/KEY: Transcript Start Site
<222> LOCATION: (1)..(116)

<400> SEQUENCE: 151
ccccagcgcc gctcggccgc ctcctccgag gaacaatgcg gcgcctccgg gcgtagcgtc    60
gcgcggggcc ggacgccgga caccagagcg cgggcggcgg agccagcggg cgagagagcg   120
cgcggcgggc gcgggttgcc ctcgtcgaga gccatgggcg cggcgcggcg cggggctgag   180
gatcggcgcg gcccggaggc gctggggacc ggggcg                             216

<210> SEQ ID NO 152
<211> LENGTH: 119
<212> TYPE: DNA
<213> ORGANISM: Homo sapiens
<220> FEATURE:
<221> NAME/KEY: Transcript Start Site
<222> LOCATION: (1)..(19)

<400> SEQUENCE: 152
acctccattg gcttccgcct ctgggatctg agagaagcga aagcgtcttt ctgaggggtg    60
tcttgagagt ggcagagggc agcgggtcca ggctccatga ggaggcaagg tgagagctg    119

<210> SEQ ID NO 153
<211> LENGTH: 115
<212> TYPE: DNA
<213> ORGANISM: Homo sapiens
<220> FEATURE:
<221> NAME/KEY: Transcript Start Site
<222> LOCATION: (1)..(15)

<400> SEQUENCE: 153
gaaggctgga gacggcaacg tggacaggaa gaagcggagg gcgaggagga gcagaggagc    60
acacagatga agcaggtgat gaaggcttta caagcgggga ggcgtgggct ggtga        115

<210> SEQ ID NO 154
```

<211> LENGTH: 126
<212> TYPE: DNA
<213> ORGANISM: Homo sapiens
<220> FEATURE:
<221> NAME/KEY: Transcript Start Site
<222> LOCATION: (1)..(26)

<400> SEQUENCE: 154
accctgcaga aagaaatca tcagctttct gcagcatcag acttagcagc atcttcctgt     60
cccaagagaa gagggatgg gaggatggca tggttcaggg cttaggggag atagggag      120
aaaaag                                                             126

<210> SEQ ID NO 155
<211> LENGTH: 126
<212> TYPE: DNA
<213> ORGANISM: Homo sapiens
<220> FEATURE:
<221> NAME/KEY: Transcript Start Site
<222> LOCATION: (1)..(26)

<400> SEQUENCE: 155
tcgtcctttc aattcattta tctgcaggaa tgattgctgc tatcagtctc gcgctcaccg    60
cccggctgag gaggtgaaag tttctcccca ggaagataaa ccgcaaaaga caatattgtg   120
catgat                                                             126

<210> SEQ ID NO 156
<211> LENGTH: 113
<212> TYPE: DNA
<213> ORGANISM: Homo sapiens
<220> FEATURE:
<221> NAME/KEY: Transcript Start Site
<222> LOCATION: (1)..(13)

<400> SEQUENCE: 156
acagctgcgc agtgtgagct tagtcacctg gaaagaggca gacagagggg cggggctgg    60
cccagactgt ttccaaggac agtaagggcc tcctggaagc agacccagcc ttt         113

<210> SEQ ID NO 157
<211> LENGTH: 129
<212> TYPE: DNA
<213> ORGANISM: Homo sapiens
<220> FEATURE:
<221> NAME/KEY: Transcript Start Site
<222> LOCATION: (1)..(29)

<400> SEQUENCE: 157
acttctgagc ctttctttt ctggagcagc tttggggatg aggcttgccc tccgttgagt    60
cacggtgaca gctctgcact gtgctgggct gagagagccc cgccgtggag ggccatctgg  120
gaaagtagg                                                          129

<210> SEQ ID NO 158
<211> LENGTH: 133
<212> TYPE: DNA
<213> ORGANISM: Homo sapiens
<220> FEATURE:
<221> NAME/KEY: Transcript Start Site
<222> LOCATION: (1)..(33)

<400> SEQUENCE: 158
aactggagaa agagggcttt cctccttgaa ggaagggtgt tgggtgaact aacactattt    60
tctcctgccc tttcccccaa tctcaatccc tttctctcca acattcttc cttgagcacc   120 ccactctggc act 133

<210> SEQ ID NO 159
<211> LENGTH: 154
<212> TYPE: DNA
<213> ORGANISM: Homo sapiens
<220> FEATURE:
<221> NAME/KEY: Transcript Start Site
<222> LOCATION: (1)..(54)

<400> SEQUENCE: 159
cctcagtcct cgcgctccct gagctgctgc cggctcaggc agccgccgaa cgtgcccgtg 60
ggcccggcct gccatcctgc cgcgcttctc ccgagacctc ggcgccgcgg cttctagtcc 120
tggccgaccg cggcgctccc gggagccggg cgtc 154

<210> SEQ ID NO 160
<211> LENGTH: 127
<212> TYPE: DNA
<213> ORGANISM: Homo sapiens
<220> FEATURE:
<221> NAME/KEY: Transcript Start Site
<222> LOCATION: (1)..(27)

<400> SEQUENCE: 160
ggcgtcacat ccggccccgt gacttccctg ggttcacagc aggggtggaa ctggattctt 60
cctggatggg gatccagatg gaggtggagg taagcatgaa gatggtgttg ggggtagggg 120
tagggat 127

<210> SEQ ID NO 161
<211> LENGTH: 111
<212> TYPE: DNA
<213> ORGANISM: Homo sapiens
<220> FEATURE:
<221> NAME/KEY: Transcript Start Site
<222> LOCATION: (1)..(11)

<400> SEQUENCE: 161
gagagagagg gacttgagtt ctgttatctt cttaagtaga ttcatattgt aagggtctcg 60
gggtgggggg gttggcaaaa tcctggagcc agaagaaagg acagcagcat t 111

<210> SEQ ID NO 162
<211> LENGTH: 116
<212> TYPE: DNA
<213> ORGANISM: Homo sapiens
<220> FEATURE:
<221> NAME/KEY: Transcript Start Site
<222> LOCATION: (1)..(16)

<400> SEQUENCE: 162
gccagggcga gacagcccgc cggccgcccg gatctccacc tgccacccca gagctgggac 60
agcagccggg ctgcggcact gggagggaga ccccacagtg gcctcttctg ccaccc 116

<210> SEQ ID NO 163
<211> LENGTH: 114
<212> TYPE: DNA
<213> ORGANISM: Homo sapiens
<220> FEATURE:
<221> NAME/KEY: Transcript Start Site
<222> LOCATION: (1)..(14)

<400> SEQUENCE: 163
acctaagcac tgtagctgtg gaagaaaggg gatctgaagg caggcacctg ggagtgttct 60
aggtcacatt ttactggcga acgcatctct tgatggacgg agcgctgctg aggt    114

<210> SEQ ID NO 164
<211> LENGTH: 122
<212> TYPE: DNA
<213> ORGANISM: Homo sapiens
<220> FEATURE:
<221> NAME/KEY: Transcript Start Site
<222> LOCATION: (1)..(22)

<400> SEQUENCE: 164
cgtctgcatc aagtctgaaa gcagacgcgc aactttcgca gaatccacct taaaatctct    60
gccttaaact gcaccagccc ccaaaaaatc caagggggga aagcaggcgg ggggagagca    120
ga    122

<210> SEQ ID NO 165
<211> LENGTH: 133
<212> TYPE: DNA
<213> ORGANISM: Homo sapiens
<220> FEATURE:
<221> NAME/KEY: Transcript Start Site
<222> LOCATION: (1)..(33)

<400> SEQUENCE: 165
tgtgcagctc ttcacggcag ctggccccag ccagcggaag gcgcctatga gccctgagcc    60
tgtggtcctc agcttgggcg gccagcggcc tctagcaggc ccccccctcg accccacccc    120
cgtcaggaag tgc    133

<210> SEQ ID NO 166
<211> LENGTH: 151
<212> TYPE: DNA
<213> ORGANISM: Homo sapiens
<220> FEATURE:
<221> NAME/KEY: Transcript Start Site
<222> LOCATION: (1)..(51)

<400> SEQUENCE: 166
gcgaaggagc agccaaccta accctacctg ctgtgaccag gtggaggtgt gtggtggaag    60
gggaaagccg gccggctggc aaagcgctgc ggagaaagac acgaggctcc tgagcaggga    120
aagccgaggt tgccaccgca ggcctggcac g    151

<210> SEQ ID NO 167
<211> LENGTH: 111
<212> TYPE: DNA
<213> ORGANISM: Homo sapiens
<220> FEATURE:
<221> NAME/KEY: Transcript Start Site
<222> LOCATION: (1)..(11)

<400> SEQUENCE: 167
ctccagtcac tccccgaaat gccagtcgac ttcactgggt actggaagat gttggtcaac    60
gagaatttcg aggagtacct gcgcgccctc ggtaagcgct gcccgctgcg c    111

<210> SEQ ID NO 168
<211> LENGTH: 147
<212> TYPE: DNA
<213> ORGANISM: Homo sapiens
<220> FEATURE:
<221> NAME/KEY: Transcript Start Site
<222> LOCATION: (1)..(47)

<400> SEQUENCE: 168

```
ccctggcagg gggcctgagc gcgcgcgagg agcagccgct gccgccgctc ggggtcgcct    60
ggagccccag attcccgagc gctcggctcg catggcagcc gcttcggcgc ccggccccgc   120
ggccagctag gggcggcccc gcgctcc                                       147

<210> SEQ ID NO 169
<211> LENGTH: 139
<212> TYPE: DNA
<213> ORGANISM: Homo sapiens
<220> FEATURE:
<221> NAME/KEY: Transcript Start Site
<222> LOCATION: (1)..(39)

<400> SEQUENCE: 169 actggggtt agagacaagc gagcttctgc gtctgactcg cagcttgaga ctggcggagg    60
gaagcccgcc caggctctat aaggagacaa ggtgagatgc tgagggagga ctcaggagga   120
cccccacccc acatagacg                                               139

<210> SEQ ID NO 170
<211> LENGTH: 155
<212> TYPE: DNA
<213> ORGANISM: Homo sapiens
<220> FEATURE:
<221> NAME/KEY: Transcript Start Site
<222> LOCATION: (1)..(55)

<400> SEQUENCE: 170 gaagggcaa tgtagcaatt atatgagtaa tgcagtggca gatcttctat gagaaattaa    60
aactggagaa agagggcttt cctccttgaa ggaagggtgt tgggtgaact aacactattt   120
tctcctgccc ttttcccccaa tctcaatccc tttct                            155

<210> SEQ ID NO 171
<211> LENGTH: 150
<212> TYPE: DNA
<213> ORGANISM: Homo sapiens
<220> FEATURE:
<221> NAME/KEY: Transcript Start Site
<222> LOCATION: (1)..(50)

<400> SEQUENCE: 171
gaggagccgc atccacacac cctgcgctgc cctgtcctgc gcgagtggag ctctgaagaa    60
gctctgagcg gagttgtgtt cttccccagg taaccgattt cccccttctg ccgtggcttc   120
gctgcgtccg cattggggca cgggcggctt                                   150

<210> SEQ ID NO 172
<211> LENGTH: 132
<212> TYPE: DNA
<213> ORGANISM: Homo sapiens
<220> FEATURE:
<221> NAME/KEY: Transcript Start Site
<222> LOCATION: (1)..(32)

<400> SEQUENCE: 172
ctttgggatg tgggaagctg gtgagaaggc acactctctc cacagttaga tttgggagga    60
ggcctgactt gggagaggga tccaggctca caccgccctg tcctgtgtcc tgtctgcaga   120
cagaggaact ga                                                     132

<210> SEQ ID NO 173
<211> LENGTH: 114
<212> TYPE: DNA
<213> ORGANISM: Homo sapiens
```

```
<220> FEATURE:
<221> NAME/KEY: Transcript Start Site
<222> LOCATION: (1)..(14)

<400> SEQUENCE: 173
ccggcagtct ccagccgtcc cgcccgcttg tggccaactg gctccagtca ctccccgaaa      60
tgccagtcga cttcactggg tactggaaga tgttggtcaa cgagaatttc gagg          114

<210> SEQ ID NO 174
<211> LENGTH: 116
<212> TYPE: DNA
<213> ORGANISM: Homo sapiens
<220> FEATURE:
<221> NAME/KEY: Transcript Start Site
<222> LOCATION: (1)..(16)

<400> SEQUENCE: 174
ctgagggaga tcgggtgctg agcaggatgc agggccgcgt ggcagggagc tgcgctcctc      60
tgggcctgct cctggtctgt cttcatctcc caggtatgga ggccgtgatg cccttg        116

<210> SEQ ID NO 175
<211> LENGTH: 168
<212> TYPE: DNA
<213> ORGANISM: Homo sapiens
<220> FEATURE:
<221> NAME/KEY: Transcript Start Site
<222> LOCATION: (1)..(68)

<400> SEQUENCE: 175
gagcctgctc tggagcctga ctgctcggtt aggacctcgg agagcgccag gcgccgcgac      60
cagagggccc agagaagcgg ccggagcccg cctacctcgg ccccctcagc ttcccgggct     120
ggcaggcggc tagaggcgtc tgaggaaggt gcctaagtcc tgggtcag                 168

<210> SEQ ID NO 176
<211> LENGTH: 155
<212> TYPE: DNA
<213> ORGANISM: Homo sapiens
<220> FEATURE:
<221> NAME/KEY: Transcript Start Site
<222> LOCATION: (1)..(55)

<400> SEQUENCE: 176
gtgggaacag tttaattgta tccatgagga ttcttagtaa tcaggatgcc agtgtgtgtt      60
ttccagagcc tagagctgac ataaataatg tagcgtacct cgctttgtgc aggcttgctg    120
aggaatgctg atggagaaaa agccaaactg ggatc                                155

<210> SEQ ID NO 177
<211> LENGTH: 113
<212> TYPE: DNA
<213> ORGANISM: Homo sapiens
<220> FEATURE:
<221> NAME/KEY: Transcript Start Site
<222> LOCATION: (1)..(13)

<400> SEQUENCE: 177
tgcgccgcat atatagcagc ggcggcggtg gcggcggcca caccgggcgg cggacacgtg      60
gagggacccg gcccgcgcct tctgccctg ctgccggccg cgccatgcgg tga            113

<210> SEQ ID NO 178
<211> LENGTH: 115
<212> TYPE: DNA
<213> ORGANISM: Homo sapiens
```

```
<220> FEATURE:
<221> NAME/KEY: Transcript Start Site
<222> LOCATION: (1)..(15)

<400> SEQUENCE: 178
aactttcgca gaatccacct taaaatctct gccttaaact gcaccagccc ccaaaaaatc    60
caagggggga aagcaggcgg ggggagagca gattcccccc tcccctctc ctctc          115

<210> SEQ ID NO 179
<211> LENGTH: 147
<212> TYPE: DNA
<213> ORGANISM: Homo sapiens
<220> FEATURE:
<221> NAME/KEY: Transcript Start Site
<222> LOCATION: (1)..(47)

<400> SEQUENCE: 179
cctgggcacc agagcgctgt ccccggccga gcgcacagct ccggcgccgc gaggcagagc    60
cccggcgtcc ccggcggtgc gctgccggct cgcgcagccc agccatcccg ccccgccgcc   120
caccttgaca gccgggagcg ctgagga                                       147

<210> SEQ ID NO 180
<211> LENGTH: 116
<212> TYPE: DNA
<213> ORGANISM: Homo sapiens
<220> FEATURE:
<221> NAME/KEY: Transcript Start Site
<222> LOCATION: (1)..(16)

<400> SEQUENCE: 180
ccaatttacc cgagcacctt ctcttcactc agccaactgc tcgctcgctc acctccctcc    60
tctgcaccat gaccacctgc agccgccagt tcacctcctc cagctccatg aagggc        116

<210> SEQ ID NO 181
<211> LENGTH: 126
<212> TYPE: DNA
<213> ORGANISM: Homo sapiens
<220> FEATURE:
<221> NAME/KEY: Transcript Start Site
<222> LOCATION: (1)..(26)

<400> SEQUENCE: 181
cgctacctgc agcccagtcg ccgccgccag cggagcggcc cgggcgggac gcggcgggag    60
cgcgcgtgtg cgggacgcag cgcggggat gcgcgcgggc cgcggaggcg ccgcaaccaa    120
caggcg                                                              126

<210> SEQ ID NO 182
<211> LENGTH: 117
<212> TYPE: DNA
<213> ORGANISM: Homo sapiens
<220> FEATURE:
<221> NAME/KEY: Transcript Start Site
<222> LOCATION: (1)..(17)

<400> SEQUENCE: 182
ggcggcggcc acaccgggcg gcggacacgt ggagggaccc ggcccgcgcc ttctgcccct    60
gctgccggcc gcgccatgcg gtgagcgccc caggccgcca gcccaccc gacccgg         117

<210> SEQ ID NO 183
<211> LENGTH: 133
<212> TYPE: DNA
<213> ORGANISM: Homo sapiens
```

```
<220> FEATURE:
<221> NAME/KEY: Transcript Start Site
<222> LOCATION: (1)..(33)

<400> SEQUENCE: 183
gggaggatgg gagatgcgcc tctgtcccgg gcagcctcgt gccacctaag cactgtagct    60
gtggaagaaa ggggatctga aggcaggcac ctgggagtgt tctaggtcac attttactgg   120
cgaacgcatc tct                                                      133

<210> SEQ ID NO 184
<211> LENGTH: 115
<212> TYPE: DNA
<213> ORGANISM: Homo sapiens
<220> FEATURE:
<221> NAME/KEY: Transcript Start Site
<222> LOCATION: (1)..(15)

<400> SEQUENCE: 184
cgagccgcac acagccatcc atcctccccc ttccctctct ccctgtcct ctctctccgg    60 gctcccaccg ccgccgcggg ccggggagcc accggccgcc accatgagtt ccttc        115

<210> SEQ ID NO 185
<211> LENGTH: 105
<212> TYPE: DNA
<213> ORGANISM: Homo sapiens
<220> FEATURE:
<221> NAME/KEY: Transcript Start Site
<222> LOCATION: (1)..(5)

<400> SEQUENCE: 185
tctctcttgt ctgctgcccg gcgagacgtg actttgttcc tcctttgcct tctgcgatga   60
tggtgaggcc tccccagcca cgtggaactg tgagtccatt aaacc                   105

<210> SEQ ID NO 186
<211> LENGTH: 105
<212> TYPE: DNA
<213> ORGANISM: Homo sapiens
<220> FEATURE:
<221> NAME/KEY: Transcript Start Site
<222> LOCATION: (1)..(5)

<400> SEQUENCE: 186
cagaagcttc ccagataagt ggaaggcagt gacacattga tggtacggag tggatgatca   60
gggcactgag aatcatccga tggaggacag aggtgttgac cactg                   105

<210> SEQ ID NO 187
<211> LENGTH: 150
<212> TYPE: DNA
<213> ORGANISM: Homo sapiens
<220> FEATURE:
<221> NAME/KEY: Transcript Start Site
<222> LOCATION: (1)..(50)

<400> SEQUENCE: 187
gtgggtgggt gaatgtgaag aggcggcgtt gggctaggcc cctgcagccc gctcggagcg   60
tcctaggccc ggggctgcgc tgtgaaagac ccagattctc atcccagagg cccagcagtc  120
ctgaaaggcc tcctctccga ccctgagccg                                    150

<210> SEQ ID NO 188
<211> LENGTH: 150
<212> TYPE: DNA
<213> ORGANISM: Homo sapiens
```

```
<220> FEATURE:
<221> NAME/KEY: Transcript Start Site
<222> LOCATION: (1)..(50)

<400> SEQUENCE: 188
ctcctcctcc tcctgccctc tcgggctaca ccaccaccaa cagtggcggc ggcggcagca    60
gcggcaaagg ccacagcagg gacttcgtcc tccggaggga cctttccgcc acggcccccg   120
cggcggccat gcacggggcc ccgctcggag                                    150

<210> SEQ ID NO 189
<211> LENGTH: 161
<212> TYPE: DNA
<213> ORGANISM: Homo sapiens
<220> FEATURE:
<221> NAME/KEY: Transcript Start Site
<222> LOCATION: (1)..(61)

<400> SEQUENCE: 189
atcgtattca gcatgttttg cacaagaaat gtcagccaga aagggctatc tgctcccttc    60
gccaaattat cccacaacaa tgtcatgctc ggagagcccc gccgcgaact cttttttggt   120
cgactcgctc atcagctcgg gcagaggcga ggcaggcggc g                       161

<210> SEQ ID NO 190
<211> LENGTH: 123
<212> TYPE: DNA
<213> ORGANISM: Homo sapiens
<220> FEATURE:
<221> NAME/KEY: Transcript Start Site
<222> LOCATION: (1)..(23)

<400> SEQUENCE: 190
gcggctgctg ccttcatctg gggaaattcg tggccactgc aagtttacta cgcgaggcgc    60
agccaatgcc aagcgccgag gccgaggagg gctaaacact gcggccgcgg ctccgaacaa   120
taa                                                                 123

<210> SEQ ID NO 191
<211> LENGTH: 111
<212> TYPE: DNA
<213> ORGANISM: Homo sapiens
<220> FEATURE:
<221> NAME/KEY: Transcript Start Site
<222> LOCATION: (1)..(11)

<400> SEQUENCE: 191
tgccagtcga cttcactggg tactggaaga tgttggtcaa cgagaatttc gaggagtacc    60
tgcgcgccct cggtaagcgc tgcccgctgc gccctgggcg ccccgccgag c             111

<210> SEQ ID NO 192
<211> LENGTH: 114
<212> TYPE: DNA
<213> ORGANISM: Homo sapiens
<220> FEATURE:
<221> NAME/KEY: Transcript Start Site
<222> LOCATION: (1)..(14)

<400> SEQUENCE: 192
gcttcgtctc tcattttctc ttgctgccgc gatgtacgaa gttccttttg cctgccgcga    60
tgattttgag gcctccccag ccatgtgaaa ctgtaagtcc aattaaaccc gttt         114

<210> SEQ ID NO 193
<211> LENGTH: 148
```

```
<212> TYPE: DNA
<213> ORGANISM: Homo sapiens
<220> FEATURE:
<221> NAME/KEY: Transcript Start Site
<222> LOCATION: (1)..(48)

<400> SEQUENCE: 193
gttgagggtc ttgatctgct cgcgctcctc ggtcctcacc ctctggatgc tggggtcgat      60
ttgcaggttg aggggagtca ggagactctg gttgacagtg acctcttgga tacctccagg     120
agggcagaca ggaaagccag ggccaccg                                        148

<210> SEQ ID NO 194
<211> LENGTH: 133
<212> TYPE: DNA
<213> ORGANISM: Homo sapiens
<220> FEATURE:
<221> NAME/KEY: Transcript Start Site
<222> LOCATION: (1)..(33)

<400> SEQUENCE: 194
tatggtggtg gccttggtgc tggcttgggt ggtggctttg gtggtggctt tgctggtggt      60
gatgggcttc tggtgggcag tgagaaggtg accatgcaga acctcaatga ccgcctggcc     120
tcctacctgg aca                                                        133

<210> SEQ ID NO 195
<211> LENGTH: 116
<212> TYPE: DNA
<213> ORGANISM: Homo sapiens
<220> FEATURE:
<221> NAME/KEY: Transcript Start Site
<222> LOCATION: (1)..(16)

<400> SEQUENCE: 195
ccgcctcaga gcaccccaaa cttgacgcca tgaagatccc ggtccttcct gccgtggtgc      60
tcctctccct cctggtgctc cactctgccc agggagccac cctgggtggt cctgag         116

<210> SEQ ID NO 196
<211> LENGTH: 126
<212> TYPE: DNA
<213> ORGANISM: Homo sapiens
<220> FEATURE:
<221> NAME/KEY: Transcript Start Site
<222> LOCATION: (1)..(26)

<400> SEQUENCE: 196
agcggctttt gtacccagtt gcttcctggc tgctttacgg tcgatttgca ggcagtccgc      60
tttgtacaag ccatggtata gaggcttcct tatttacctc ccttatcctt cagctggagc     120
tctgcg                                                                126

<210> SEQ ID NO 197
<211> LENGTH: 137
<212> TYPE: DNA
<213> ORGANISM: Homo sapiens
<220> FEATURE:
<221> NAME/KEY: Transcript Start Site
<222> LOCATION: (1)..(37)

<400> SEQUENCE: 197
gcccacctct gcctgaaact tctcttttgg gctcctgtgc tgtgacatac tagcagtatt      60
tgtttgcccc tcttaagacc atcccttcag tttcattcct gcctcagttt ctcctcctca     120
catttctgct gttccac                                                    137
```

<210> SEQ ID NO 198
<211> LENGTH: 159
<212> TYPE: DNA
<213> ORGANISM: Homo sapiens
<220> FEATURE:
<221> NAME/KEY: Transcript Start Site
<222> LOCATION: (1)..(59)

<400> SEQUENCE: 198
tgggggtggg ctttggcagt ggcggggta gcagctccag cgtcaaattt gtctccacca      60
cctcctcctc ccggaagagc ttcaagagct aagaacctgc tgcaagtcac tgccttccaa    120
gtgcagcaac ccagcccatg gagattgcct cttctaggc                            159

<210> SEQ ID NO 199
<211> LENGTH: 117
<212> TYPE: DNA
<213> ORGANISM: Homo sapiens
<220> FEATURE:
<221> NAME/KEY: Transcript Start Site
<222> LOCATION: (1)..(17)

<400> SEQUENCE: 199
gactgctgtg ctagcaatca aggagactcc atgggcgtag gaccgtccga gccaggtgcg      60
gaatataatc tcatggtgca ccattttta agcctgtcag aaaagcgccg tattcag         117

<210> SEQ ID NO 200
<211> LENGTH: 129
<212> TYPE: DNA
<213> ORGANISM: Homo sapiens
<220> FEATURE:
<221> NAME/KEY: Transcript Start Site
<222> LOCATION: (1)..(29)

<400> SEQUENCE: 200
ggcagacagg aaagccaggg ccaccgaagc cacctccaaa gccagctccg ccaccgagcc      60
caaagccacc accagctcca ccgccgaaac caaatccact accggcacca cctccaaagc    120
catagccgc                                                             129

<210> SEQ ID NO 201
<211> LENGTH: 111
<212> TYPE: DNA
<213> ORGANISM: Homo sapiens
<220> FEATURE:
<221> NAME/KEY: Transcript Start Site
<222> LOCATION: (1)..(11)

<400> SEQUENCE: 201
tgaatcacca gatgttagca ggaggcgaga tgaaaagcca cagtcctctc gcagcagctg      60
ctggaggtgg ctgtgtcctt gctgatggac ctggaggtgg ctgtgtcctt g              111

<210> SEQ ID NO 202
<211> LENGTH: 114
<212> TYPE: DNA
<213> ORGANISM: Homo sapiens
<220> FEATURE:
<221> NAME/KEY: Transcript Start Site
<222> LOCATION: (1)..(14)

<400> SEQUENCE: 202
tggctttgga ctcttctcct cctccacctc ctcctcctcc tcccgcgccg ccgcctcctc      60
ctcctcttcc tctccgcgcc ttcgctacgc gcccggccgc ccgaggcaga tcca           114

<210> SEQ ID NO 203
<211> LENGTH: 112
<212> TYPE: DNA
<213> ORGANISM: Homo sapiens
<220> FEATURE:
<221> NAME/KEY: Transcript Start Site
<222> LOCATION: (1)..(12)

<400> SEQUENCE: 203
tgactaagct cttccctggg tggggctttt agtgtggtaa tgaggagagc ttgccaaagt    60
tcatcttcaa ttcaggcatc tttggatcca actagttttt attttattta tt           112

<210> SEQ ID NO 204
<211> LENGTH: 138
<212> TYPE: DNA
<213> ORGANISM: Homo sapiens
<220> FEATURE:
<221> NAME/KEY: Transcript Start Site
<222> LOCATION: (1)..(38)

<400> SEQUENCE: 204
gccacagcag ggttcaattg ccagtgcttt tatctgcaga aatgtgctgg gatgggcact    60
ttgtttaaaa tttccctttg ctactgggag gaaatggaaa gcagtaagat aacttcattt   120
gtaaggtaat atctgtgc                                                 138

<210> SEQ ID NO 205
<211> LENGTH: 121
<212> TYPE: DNA
<213> ORGANISM: Homo sapiens
<220> FEATURE:
<221> NAME/KEY: Transcript Start Site
<222> LOCATION: (1)..(21)

<400> SEQUENCE: 205
tggggtcgct ccgcagctgc gagttcatgg cgtcccggtg ctccgagccc tacccggagg    60
tctccagaat ccctaccgtc agggatgca agtgaggaat gggctggcg gccaaggggt    120 t                                                                   121

<210> SEQ ID NO 206
<211> LENGTH: 135
<212> TYPE: DNA
<213> ORGANISM: Homo sapiens
<220> FEATURE:
<221> NAME/KEY: Transcript Start Site
<222> LOCATION: (1)..(35)

<400> SEQUENCE: 206
cgccactaac ttacgcctcg gggatcagag agaagcgagg ttctcgttct gagggacagg    60
cttgagatcg gctgaagaga gcgggcccag gctctgtgag gaggcaaggt gagaggctga   120
gggaggactg aggac                                                    135

<210> SEQ ID NO 207
<211> LENGTH: 145
<212> TYPE: DNA
<213> ORGANISM: Homo sapiens
<220> FEATURE:
<221> NAME/KEY: Transcript Start Site
<222> LOCATION: (1)..(45)

<400> SEQUENCE: 207
tgtgacatcc ctgacttgcg cattggtctg accagcaact cgagatccac ggagggaagc    60
aggcgcaggc tctgtgagga ggcaaggtgg gggcaggctg tgccaggcgt caaagtcagg    120
accctaagag agagctgagg gttcc    145

<210> SEQ ID NO 208
<211> LENGTH: 109
<212> TYPE: DNA
<213> ORGANISM: Homo sapiens
<220> FEATURE:
<221> NAME/KEY: Transcript Start Site
<222> LOCATION: (1)..(9)

<400> SEQUENCE: 208
atgccactga cttgcgcact gggggttaga dacaagcgag cttctgcgtc tgactcgcag    60
cttgagactg gcggagggaa gcccgcccag gctctataag gagacaagg    109

<210> SEQ ID NO 209
<211> LENGTH: 106
<212> TYPE: DNA
<213> ORGANISM: Homo sapiens
<220> FEATURE:
<221> NAME/KEY: Transcript Start Site
<222> LOCATION: (1)..(6)

<400> SEQUENCE: 209
ggcaacctgc ttgggaaccc tgttacactg tggaagcttt gttcttttgc tctttgcagt    60
aaatcttgct gctgctcact ctttgggtcc acactgcttt tatgag    106

<210> SEQ ID NO 210
<211> LENGTH: 109
<212> TYPE: DNA
<213> ORGANISM: Homo sapiens
<220> FEATURE:
<221> NAME/KEY: Transcript Start Site
<222> LOCATION: (1)..(9)

<400> SEQUENCE: 210
cactctcttg cctgcagcca tgtaagttgt gcctttgctt ctccttcacc ttccaccatg    60
attgtgaggc ctccccagcc atgtggaatt gtgagtcaat taaacgtct    109

<210> SEQ ID NO 211
<211> LENGTH: 115
<212> TYPE: DNA
<213> ORGANISM: Homo sapiens
<220> FEATURE:
<221> NAME/KEY: Transcript Start Site
<222> LOCATION: (1)..(15)

<400> SEQUENCE: 211
gaaaagccac agtcctctcg cagcagctgc tggaggtggc tgtgtccttg ctgatggacc    60
tggaggtggc tgtgtccttg ctgatggacc tggaggtggc tgtatccttg ctgat    115

<210> SEQ ID NO 212
<211> LENGTH: 162
<212> TYPE: DNA
<213> ORGANISM: Homo sapiens
<220> FEATURE:
<221> NAME/KEY: Transcript Start Site
<222> LOCATION: (1)..(62)

<400> SEQUENCE: 212
gggagagagc agatattgcc tattatgctt ttccttccca gctggagaag gcctcagctg    60
tgtcagactg ggactgctgg tgattttct gtagttagag ggaaacacaa aacgaagagc    120

```
ggcccactcc cagcttacgc cgatggtgag cccacctctc ct                162

<210> SEQ ID NO 213
<211> LENGTH: 111
<212> TYPE: DNA
<213> ORGANISM: Homo sapiens
<220> FEATURE:
<221> NAME/KEY: Transcript Start Site
<222> LOCATION: (1)..(11)

<400> SEQUENCE: 213
gggcagtgca agaacaggac tttcaagtgt gaaggctgat tctgagcccc agtgagctct    60
gtgacaatgg tgctagaagg tactggtgtt cgtatcttct tccagaggaa a            111
```